United States Patent
Janssen et al.

(10) Patent No.: US 11,426,468 B2
(45) Date of Patent: Aug. 30, 2022

(54) CYSTEINE LINKED NANOBODY DIMERS

(71) Applicant: Ablynx N.V., Ghent-Zwijnaarde (BE)

(72) Inventors: Daniel Janssen, Puurs (BE); Peter Schotte, De Pinte (BE); Francis Descamps, Roeselare (BE); Carlo Boutton, Wielsbeke (BE); Peter Casteels, Erpe-Mere (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 27 days.

(21) Appl. No.: 15/536,751

(22) PCT Filed: Dec. 18, 2015

(86) PCT No.: PCT/EP2015/080536
§ 371 (c)(1),
(2) Date: Jun. 16, 2017

(87) PCT Pub. No.: WO2016/097313
PCT Pub. Date: Jun. 23, 2016

(65) Prior Publication Data
US 2017/0360955 A1    Dec. 21, 2017

Related U.S. Application Data

(60) Provisional application No. 62/140,611, filed on Mar. 31, 2015, provisional application No. 62/094,179, filed on Dec. 19, 2014.

(51) Int. Cl.
| | | |
|---|---|---|
| *A61K 47/68* | (2017.01) | |
| *C07K 16/18* | (2006.01) | |
| *C07K 16/28* | (2006.01) | |
| *A61K 51/10* | (2006.01) | |
| *C07K 16/30* | (2006.01) | |
| *C07K 16/46* | (2006.01) | |
| *A61K 39/00* | (2006.01) | |
| *C07K 1/16* | (2006.01) | |

(52) U.S. Cl.
CPC ...... *A61K 47/6879* (2017.08); *A61K 47/6803* (2017.08); *A61K 47/6817* (2017.08); *A61K 47/6843* (2017.08); *A61K 47/6849* (2017.08); *A61K 47/6851* (2017.08); *A61K 47/6855* (2017.08); *A61K 51/109* (2013.01); *A61K 51/1018* (2013.01); *A61K 51/1036* (2013.01); *A61K 51/1045* (2013.01); *A61K 51/1051* (2013.01); *A61K 51/1096* (2013.01); *C07K 1/16* (2013.01); *C07K 16/18* (2013.01); *C07K 16/2863* (2013.01); *C07K 16/30* (2013.01); *C07K 16/3015* (2013.01); *C07K 16/468* (2013.01); *A61K 2039/505* (2013.01); *C07K 2317/22* (2013.01); *C07K 2317/31* (2013.01); *C07K 2317/569* (2013.01); *C07K 2317/73* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 6,511,665 | B1 * | 1/2003 | Dower | C07K 14/7155 424/130.1 |
| 8,703,135 | B2 * | 4/2014 | Beste | C07K 16/18 424/136.1 |
| 8,975,382 | B2 * | 3/2015 | Revets | A61P 43/00 530/388.8 |
| 11,021,544 | B2 * | 6/2021 | Boutton | A61K 38/07 |
| 2007/0065440 | A1 * | 3/2007 | Tomlinson | C07K 16/2875 424/145.1 |
| 2008/0008713 | A1 * | 1/2008 | Brewis | C07K 16/18 424/143.1 |
| 2009/0252681 | A1 * | 10/2009 | Laeremans | C07K 16/00 424/9.1 |
| 2011/0282033 | A1 * | 11/2011 | Gonzalez Pajuelo | A61P 37/00 530/387.3 |

(Continued)

FOREIGN PATENT DOCUMENTS

| | | |
|---|---|---|
| CN | 103333253 A | 10/2013 |
| CN | 104114579 A | 10/2014 |
| JP | 2006-523090 A | 10/2006 |

(Continued)

OTHER PUBLICATIONS

Massa et al., Bioconjugate Chem., 25:979-988, Apr. 24, 2014.*
Tomas et al., Trends Cell Biol; 24(1): 26-34, Jan. 2014.*
Maruyama et al., Peptides, 20:882-884, 1999.*
Segaliny et al., Journal of Bone Oncology 4 (2015): 1-12.*
Pincheira et al., J Immunol 2008; 181:1288-1298.*
Ji et al., Covalently dimerized Camelidae antihuman TNFa single-domain antibodies expressed in yeast *Pichia pastoris* show superior neutralizing activity. Applied Microbiology and Biotechnology. Jan. 17, 2013; 97(19): 8547-8558.

(Continued)

*Primary Examiner* — Marianne P Allen
(74) *Attorney, Agent, or Firm* — Wolf, Greenfield & Sacks, P.C.

(57) ABSTRACT

The present invention relates to dimers comprising a first polypeptide and a second polypeptide, wherein each of said first and second polypeptide comprises at least one immunoglobulin single variable domain (1ISVD) and a C-terminal extension comprising a cysteine moiety (preferably at the C-terminus), wherein said first polypeptide and said second polypeptide are covalently linked via a disulfide bond between the cysteine moiety of said first polypeptide and the cysteine moiety of said second polypeptide, in which the dimer outperformed the benchmark constructs, e.g. cognate multivalent and multispecific constructs, in various assays. The present invention provides methods for making the dimers of the invention.

Figure 3:
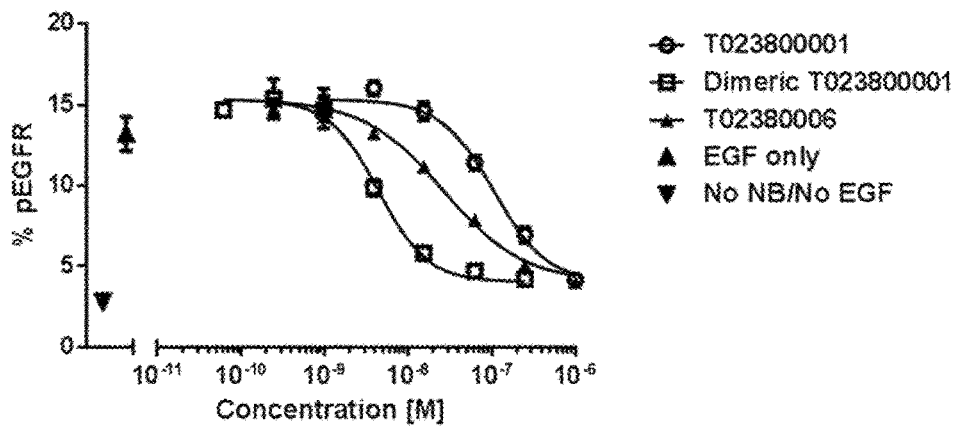

6 Claims, 8 Drawing Sheets
Specification includes a Sequence Listing.

(56) References Cited

U.S. PATENT DOCUMENTS

2012/0141460 A1      6/2012    Stals et al.

FOREIGN PATENT DOCUMENTS

| WO | WO 2004/003019 A2 | | 1/2004 |
|---|---|---|---|
| WO | WO 2004/003019 A3 | * | 1/2004 |
| WO | WO 2007/042289 A2 | | 4/2007 |
| WO | WO 2010/125187 A2 | | 11/2010 |
| WO | WO 2013/060867 A2 | | 5/2013 |
| WO | WO 2014/124316 | * | 8/2014 |

OTHER PUBLICATIONS

Leahy, Magic bullets from llamas. Structure. Jul. 2, 2013;21(7):1072-3. doi: 10.1016/j.str.2013.06.008.

Liu et al., Enhanced production of a single domain antibody with an engineered stabilizing extra disulfide bond. Microb Cell Fact. Oct. 9, 2015;14:158. doi:10.1186/s12934-015-0340-3.

Nagahara, Intermolecular disulfide bond to modulate protein function as a redox-sensing switch. Amino Acids. Jun. 2011;41(1):59-72. doi:10.1007/s00726-010-0508-4. Epub Feb. 24, 2010.

Schmitz et al., Structural evaluation of EGFR inhibition mechanisms for nanobodies/VHH domains. Structure. Jul. 2, 2013;21(7):1214-24. doi: 10.1016/j.str.2013.05.008. Epub Jun. 20, 2013.

Simmons et al., Dimerisation strategies for shark IgNAR single domain antibody fragments. J Immunol Methods. Aug. 31, 2006;315(1-2):171-84. Epub Aug. 28, 2006.

Wu et al., Influence of specific growth rate on specific productivity and intermolecular disulphide bond of recombinant protein produced by a *Pichia pastoris* Mut strain. J Biotechnol. Nov. 1, 2010; 150:S540. Abstract.

PCT/EP2015/080536, Jun. 29, 2017, International Preliminary Report on Patentability.

Decanniere et al., A single-domain antibody fragment in complex with RNase A: non-canonical loop structures and nanomolar affinity using two CDR loops. Structure. Apr. 15, 1999;7(4):361-70. doi: 10.1016/s0969-2126(99)80049-5.

Desmyter et al., Crystal structure of a camel single-domain VH antibody fragment in complex with lysozyme. Nat Struct Biol. Sep. 1996;3(9):803-11. doi: 10.1038/nsb0996-803.

Spinelli et al., The crystal structure of a llama heavy chain variable domain. Nat Struct Biol. Sep. 1996;3(9):752-7. doi: 10.1038/nsb0996-752.

Wang, Antibody Technology. Military Medical Science Press. Mar. 2009:134-7. 4 pages.

* cited by examiner

Figure 1: Constructs
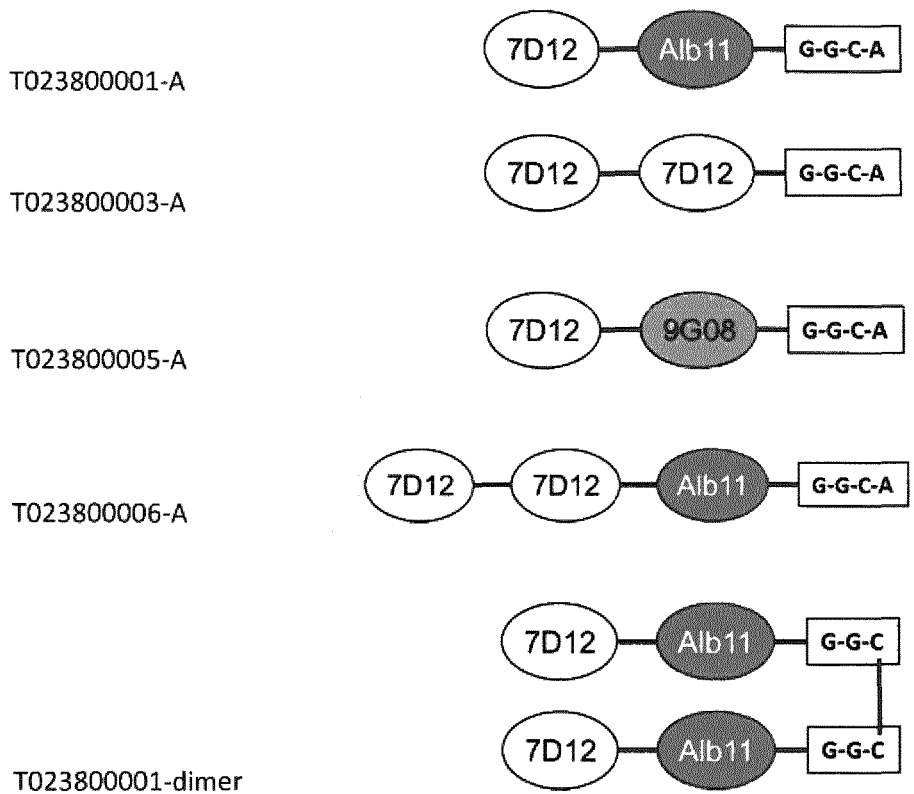
Figure 2
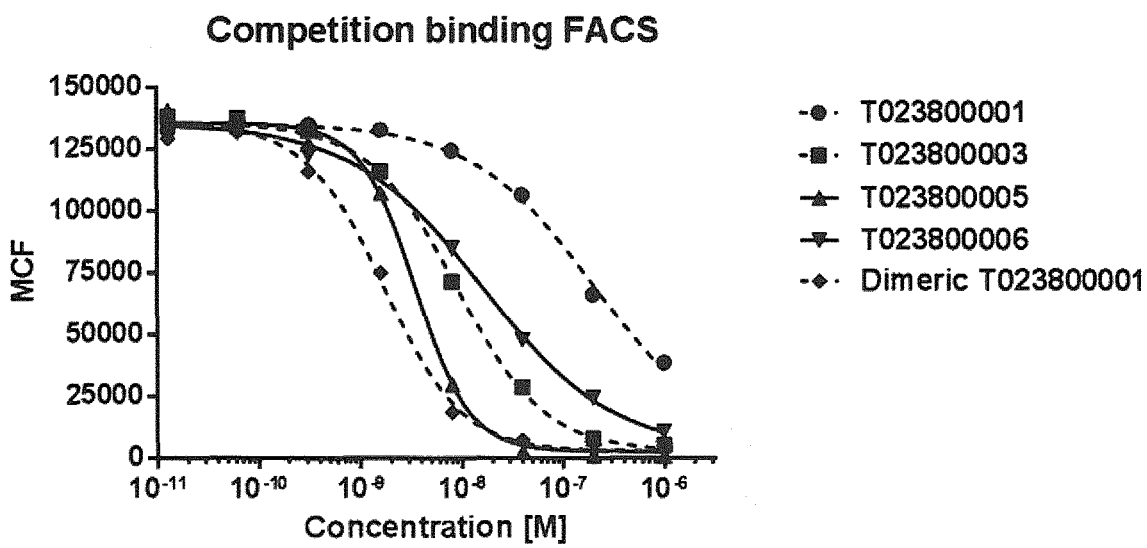

Scheme of dimer reduction

SEC profile of reduced Cysteine extended polypeptides maleimide-val-cit-MMAE

SDS-PAGE Analysis of T0238-00001-mc-val-cit-PAB-MMAE (ABL100-NC003-1)

Overlaid hydrophobic interaction chromatograms in vitro cell killing of Polypeptide-MMAE conjugates Figure 10 : Dose-dependent effect of the non-conjugated and MMAE-conjugated polypeptides
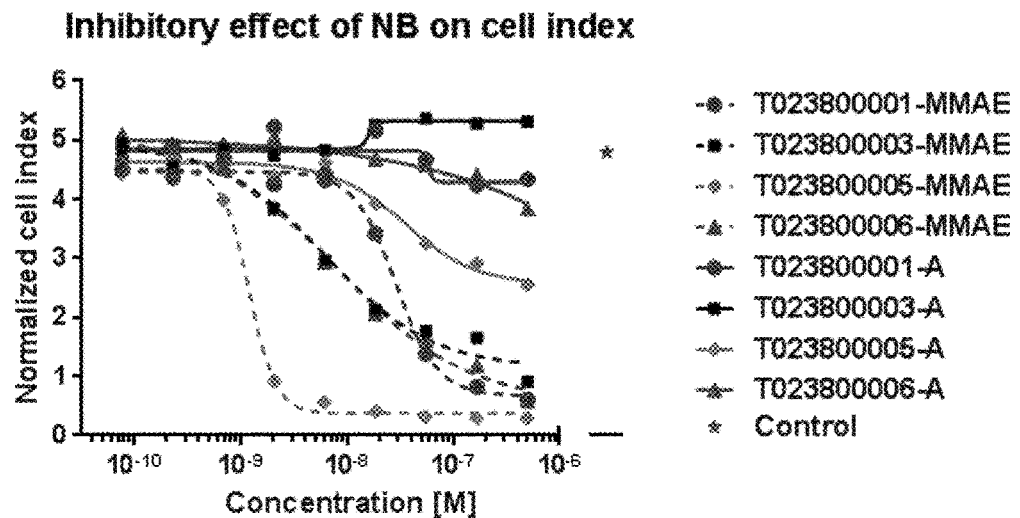
Figure 11:
in vivo efficacy of polypeptide-MMAE conjugates
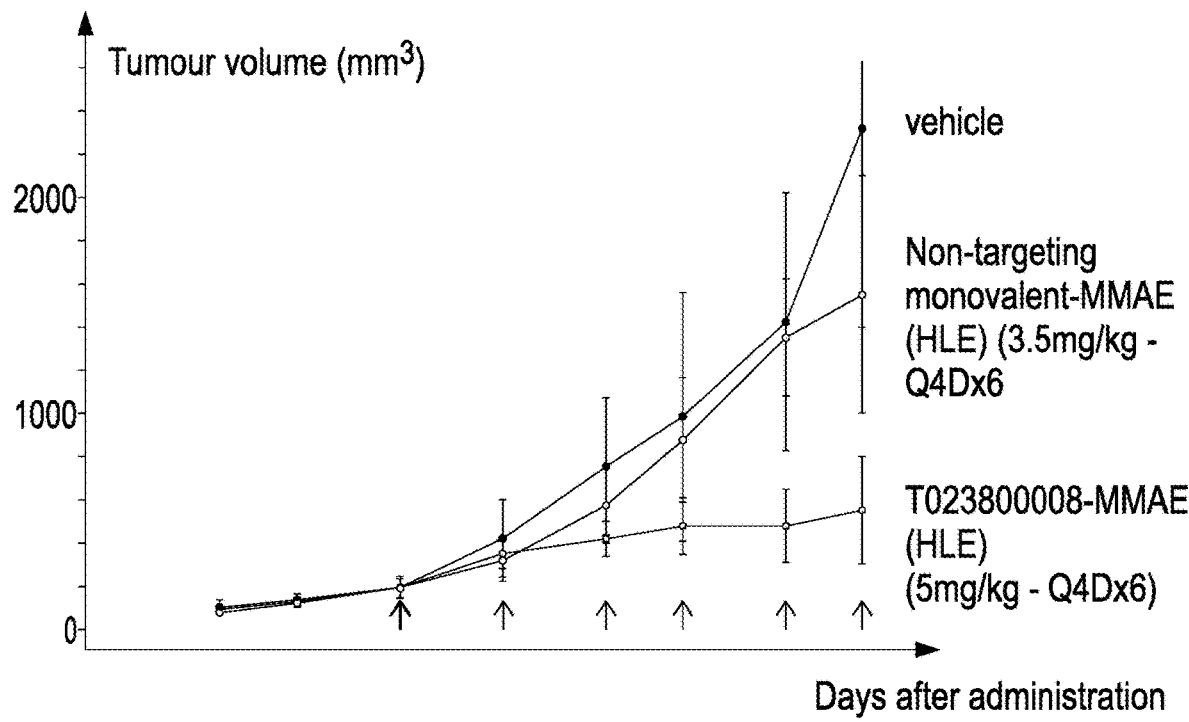

Figure 12 Modification and radiolabeling of Nbs using NCS-Bz-Df and $^{89}$Zr
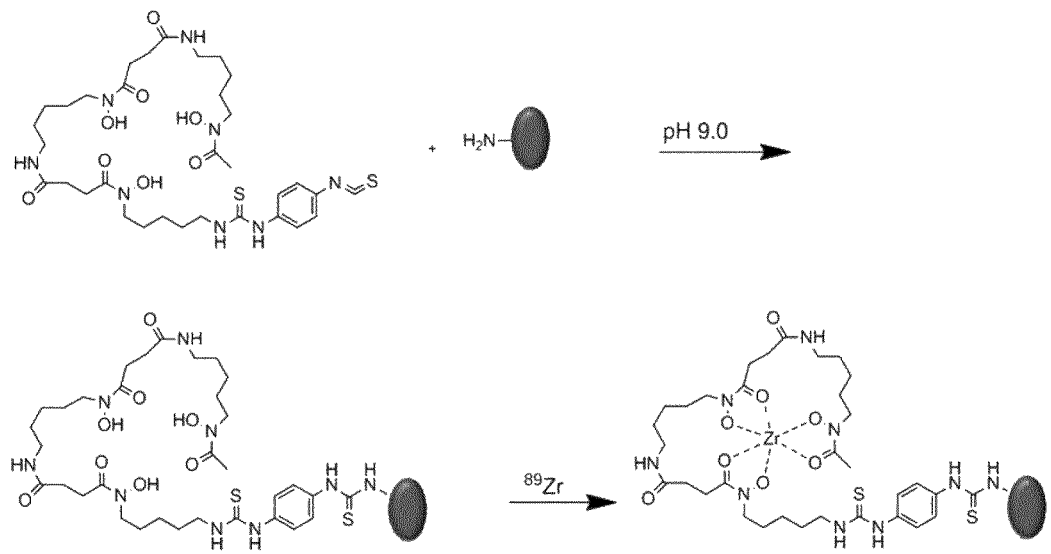
Figure 13:
Averaged %ID/g for 3 polypeptides
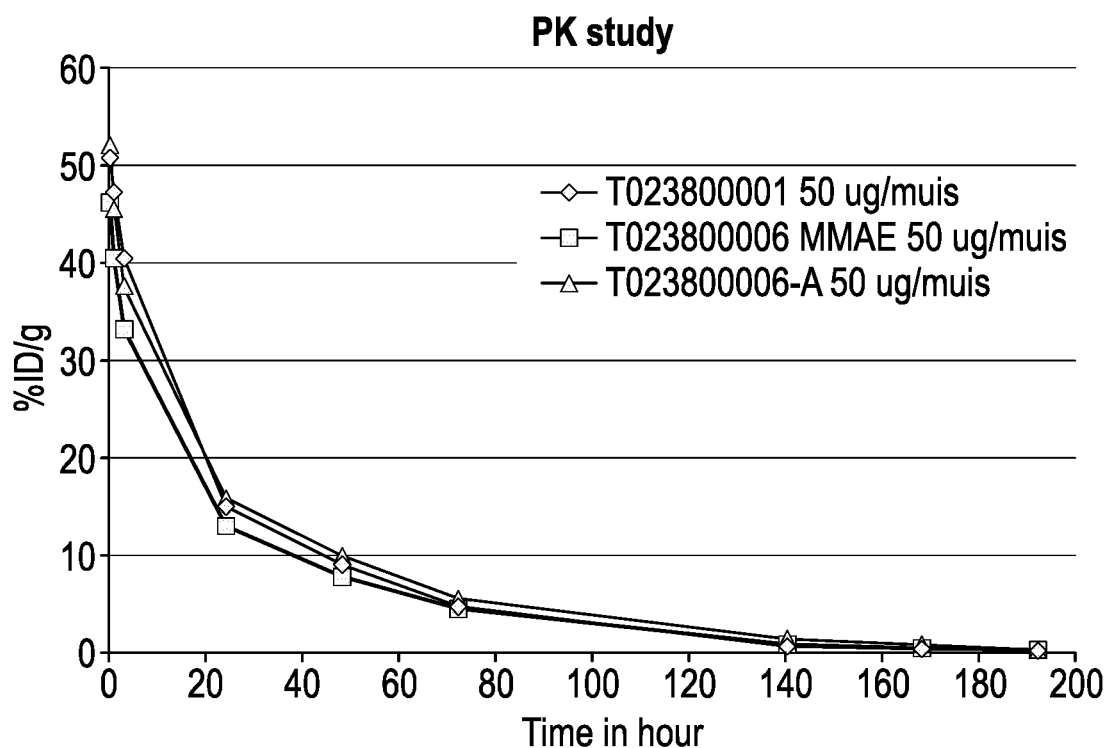

Figure 14 Dose-response curve of internalized polypeptides and constructs
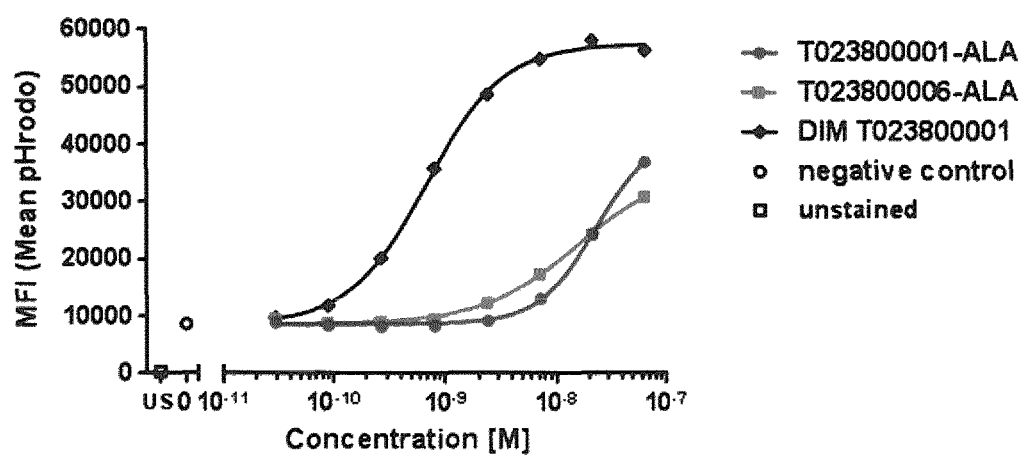

SEQUENCE LISTING

```
<160> NUMBER OF SEQ ID NOS: 44

<210> SEQ ID NO 1
<211> LENGTH: 1
<212> TYPE: PRT
<213> ORGANISM: Artificial Sequence
<220> FEATURE:
<223> OTHER INFORMATION: cysteine comprising

<400> SEQUENCE: 1

Cys
1
```

```
<210> SEQ ID NO 2
<211> LENGTH: 2
<212> TYPE: PRT
<213> ORGANISM: Artificial Sequence
<220> FEATURE:
<223> OTHER INFORMATION: cysteine comprising

<400> SEQUENCE: 2

Gly Cys
1

<210> SEQ ID NO 3
<211> LENGTH: 3
<212> TYPE: PRT
<213> ORGANISM: Artificial Sequence
<220> FEATURE:
<223> OTHER INFORMATION: cysteine comprising

<400> SEQUENCE: 3

Gly Gly Cys
1

<210> SEQ ID NO 4
<211> LENGTH: 4
<212> TYPE: PRT
<213> ORGANISM: Artificial Sequence
<220> FEATURE:
<223> OTHER INFORMATION: cysteine comprising

<400> SEQUENCE: 4

Gly Gly Gly Cys
1

<210> SEQ ID NO 5
<211> LENGTH: 5
<212> TYPE: PRT
<213> ORGANISM: Artificial Sequence
<220> FEATURE:
<223> OTHER INFORMATION: cysteine comprising

<400> SEQUENCE: 5

Gly Gly Gly Gly Cys
1               5

<210> SEQ ID NO 6
<211> LENGTH: 2
<212> TYPE: PRT
<213> ORGANISM: Artificial Sequence
<220> FEATURE:
<223> OTHER INFORMATION: cysteine comprising

<400> SEQUENCE: 6

Ala Cys
1

<210> SEQ ID NO 7
<211> LENGTH: 3
<212> TYPE: PRT
<213> ORGANISM: Artificial Sequence
<220> FEATURE:
<223> OTHER INFORMATION: cysteine comprising

<400> SEQUENCE: 7

Ala Ala Cys
1
```

```
<210> SEQ ID NO 8
<211> LENGTH: 4
<212> TYPE: PRT
<213> ORGANISM: Artificial Sequence
<220> FEATURE:
<223> OTHER INFORMATION: cysteine comprising

<400> SEQUENCE: 8

Ala Ala Ala Cys
1

<210> SEQ ID NO 9
<211> LENGTH: 5
<212> TYPE: PRT
<213> ORGANISM: Artificial Sequence
<220> FEATURE:
<223> OTHER INFORMATION: cysteine comprising

<400> SEQUENCE: 9

Ala Ala Ala Ala Cys
1               5

<210> SEQ ID NO 10
<211> LENGTH: 2
<212> TYPE: PRT
<213> ORGANISM: Artificial Sequence
<220> FEATURE:
<223> OTHER INFORMATION: cysteine comprising

<400> SEQUENCE: 10

Cys Gly
1

<210> SEQ ID NO 11
<211> LENGTH: 3
<212> TYPE: PRT
<213> ORGANISM: Artificial Sequence
<220> FEATURE:
<223> OTHER INFORMATION: cysteine comprising

<400> SEQUENCE: 11

Gly Cys Gly
1

<210> SEQ ID NO 12
<211> LENGTH: 4
<212> TYPE: PRT
<213> ORGANISM: Artificial Sequence
<220> FEATURE:
<223> OTHER INFORMATION: cysteine comprising

<400> SEQUENCE: 12

Gly Gly Cys Gly
1

<210> SEQ ID NO 13
<211> LENGTH: 5
<212> TYPE: PRT
<213> ORGANISM: Artificial Sequence
<220> FEATURE:
<223> OTHER INFORMATION: cysteine comprising

<400> SEQUENCE: 13

Gly Gly Gly Cys Gly
1               5
```

```
<210> SEQ ID NO 14
<211> LENGTH: 6
<212> TYPE: PRT
<213> ORGANISM: Artificial Sequence
<220> FEATURE:
<223> OTHER INFORMATION: cysteine comprising

<400> SEQUENCE: 14

Gly Gly Gly Gly Cys Gly
1               5

<210> SEQ ID NO 15
<211> LENGTH: 9
<212> TYPE: PRT
<213> ORGANISM: Artificial Sequence
<220> FEATURE:
<223> OTHER INFORMATION: cysteine comprising

<400> SEQUENCE: 15

Gly Gly Gly Gly Cys Gly Gly Gly Gly
1               5

<210> SEQ ID NO 16
<211> LENGTH: 3
<212> TYPE: PRT
<213> ORGANISM: Artificial Sequence
<220> FEATURE:
<223> OTHER INFORMATION: cysteine comprising

<400> SEQUENCE: 16

Ala Ala Ala
1

<210> SEQ ID NO 17
<211> LENGTH: 5
<212> TYPE: PRT
<213> ORGANISM: Artificial Sequence
<220> FEATURE:
<223> OTHER INFORMATION: cysteine comprising

<400> SEQUENCE: 17

Gly Gly Gly Gly Ser
1               5

<210> SEQ ID NO 18
<211> LENGTH: 7
<212> TYPE: PRT
<213> ORGANISM: Artificial Sequence
<220> FEATURE:
<223> OTHER INFORMATION: cysteine comprising

<400> SEQUENCE: 18

Ser Gly Gly Ser Gly Gly Ser
1               5

<210> SEQ ID NO 19
<211> LENGTH: 9
<212> TYPE: PRT
<213> ORGANISM: Artificial Sequence
<220> FEATURE:
<223> OTHER INFORMATION: cysteine comprising

<400> SEQUENCE: 19

Gly Gly Gly Gly Ser Gly Gly Gly Ser
1               5

<210> SEQ ID NO 20
```

-continued

```
<211> LENGTH: 10
<212> TYPE: PRT
<213> ORGANISM: Artificial Sequence
<220> FEATURE:
<223> OTHER INFORMATION: cysteine comprising

<400> SEQUENCE: 20

Gly Gly Gly Gly Ser Gly Gly Gly Gly Ser
1               5                   10

<210> SEQ ID NO 21
<211> LENGTH: 15
<212> TYPE: PRT
<213> ORGANISM: Artificial Sequence
<220> FEATURE:
<223> OTHER INFORMATION: cysteine comprising

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: cysteine comprising

<400> SEQUENCE: 22

Gly Gly Gly Gly Ser Gly Gly Gly Gly Ser Gly Gly Gly Gly Gly
1               5                   10                  15

Gly Ser

<210> SEQ ID NO 23
<211> LENGTH: 20
<212> TYPE: PRT
<213> ORGANISM: Artificial Sequence
<220> FEATURE:
<223> OTHER INFORMATION: cysteine comprising

<400> SEQUENCE: 23

Gly Gly Gly Gly Ser Gly Gly Gly Gly Ser Gly Gly Gly Gly Ser Gly
1               5                   10                  15

Gly Gly Gly Ser
            20

<210> SEQ ID NO 24
<211> LENGTH: 25
<212> TYPE: PRT
<213> ORGANISM: Artificial Sequence
<220> FEATURE:
<223> OTHER INFORMATION: cysteine comprising

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 25
<211> LENGTH: 30
<212> TYPE: PRT
<213> ORGANISM: Artificial Sequence
<220> FEATURE:
<223> OTHER INFORMATION: cysteine comprising
```

```
<400> SEQUENCE: 25

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25              30

<210> SEQ ID NO 26
<211> LENGTH: 35
<212> TYPE: PRT
<213> ORGANISM: Artificial Sequence
<220> FEATURE:
<223> OTHER INFORMATION: cysteine comprising

<400> SEQUENCE: 26

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 27
<211> LENGTH: 262
<212> TYPE: PRT
<213> ORGANISM: Artificial Sequence
<220> FEATURE:
<223> OTHER INFORMATION: cysteine comprising

<400> SEQUENCE: 27

Glu Val Gln Leu Glu Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
        35                  40                  45

Ser Gly Ile Ser Trp Arg Gly Asp Ser Thr Gly Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Gln Val Thr Val Ser Ser Gly Gly Gly Gly
        115                 120                 125

Ser Gly Gly Gly Ser Gly Gly Gly Ser Gly Gly Gly Ser
    130                 135                 140

Glu Val Gln Leu Val Glu Ser Gly Gly Gly Leu Val Gln Pro Gly Asn
145                 150                 155                 160

Ser Leu Arg Leu Ser Cys Ala Ala Ser Gly Phe Thr Phe Ser Ser Phe
            165                 170                 175

Gly Met Ser Trp Val Arg Gln Ala Pro Gly Lys Gly Leu Glu Trp Val
        180                 185                 190

Ser Ser Ile Ser Gly Ser Gly Ser Asp Thr Leu Tyr Ala Asp Ser Val
    195                 200                 205

Lys Gly Arg Phe Thr Ile Ser Arg Asp Asn Ala Lys Thr Thr Leu Tyr
        210                 215                 220
```

```
Leu Gln Met Asn Ser Leu Arg Pro Glu Asp Thr Ala Val Tyr Tyr Cys
225                 230                 235                 240

Thr Ile Gly Gly Ser Leu Ser Arg Ser Ser Gln Gly Thr Leu Val Thr
                245                 250                 255

Val Ser Ser Gly Gly Cys
            260
```

<210> SEQ ID NO 28
<211> LENGTH: 271
<212> TYPE: PRT
<213> ORGANISM: Artificial Sequence
<220> FEATURE:
<223> OTHER INFORMATION: cysteine comprising

<400> SEQUENCE: 28

```
Glu Val Gln Leu Glu Glu Ser Gly Gly Ser Val Gln Thr Gly Gly
1               5                   10                  15

Ser Leu Arg Leu Thr Cys Ala Ala Ser Gly Arg Thr Ser Arg Ser Tyr
                20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
        50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Glu Val Gln Leu Glu Glu Ser Gly Gly Ser Val Gln Thr Gly Gly
145                 150                 155                 160

Ser Leu Arg Leu Thr Cys Ala Ala Ser Gly Arg Thr Ser Arg Ser Tyr
                165                 170                 175

Gly Met Gly Trp Phe Arg Gln Ala Pro Gly Lys Glu Arg Glu Phe Val
            180                 185                 190

Ser Gly Ile Ser Trp Arg Gly Asp Ser Thr Gly Tyr Ala Asp Ser Val
        195                 200                 205

Lys Gly Arg Phe Thr Ile Ser Arg Asp Asn Ala Lys Asn Thr Val Asp
    210                 215                 220

Leu Gln Met Asn Ser Leu Lys Pro Glu Asp Thr Ala Ile Tyr Tyr Cys
225                 230                 235                 240

Ala Ala Ala Ala Gly Ser Ala Trp Tyr Gly Thr Leu Tyr Glu Tyr Asp
                245                 250                 255

Tyr Trp Gly Gln Gly Thr Gln Val Thr Val Ser Ser Gly Gly Cys
            260                 265                 270
```

<210> SEQ ID NO 29
<211> LENGTH: 274
<212> TYPE: PRT
<213> ORGANISM: Artificial Sequence
<220> FEATURE:
<223> OTHER INFORMATION: cysteine comprising

<400> SEQUENCE: 29

```
Glu Val Gln Leu Glu Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
                20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
        50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Ser Gly Gly Gly Gly Gly Ser
    130                 135                 140

Glu Val Gln Leu Val Glu Ser Gly Gly Leu Val Gln Ala Gly Gly
145                 150                 155                 160

Ser Leu Arg Leu Ser Cys Ala Ala Ser Gly Arg Thr Phe Ser Ser Tyr
                165                 170                 175

Ala Met Gly Trp Phe Arg Gln Ala Pro Gly Lys Glu Arg Glu Phe Val
            180                 185                 190

Val Ala Ile Asn Trp Ser Ser Gly Ser Thr Tyr Tyr Ala Asp Ser Val
        195                 200                 205

Lys Gly Arg Phe Thr Ile Ser Arg Asp Asn Ala Lys Asn Thr Met Tyr
210                 215                 220

Leu Gln Met Asn Ser Leu Lys Pro Glu Asp Thr Ala Val Tyr Tyr Cys
225                 230                 235                 240

Ala Ala Gly Tyr Gln Ile Asn Ser Gly Asn Tyr Asn Phe Lys Asp Tyr
            245                 250                 255

Glu Tyr Asp Tyr Trp Gly Gln Gly Thr Gln Val Thr Val Ser Ser Gly
        260                 265                 270

Gly Cys

<210> SEQ ID NO 30
<211> LENGTH: 406
<212> TYPE: PRT
<213> ORGANISM: Artificial Sequence
<220> FEATURE:
<223> OTHER INFORMATION: cysteine comprising

<400> SEQUENCE: 30

Glu Val Gln Leu Glu Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
                20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
        50                  55                  60

Lys Gly Arg Phe Thr Ile Ser Arg Asp Asn Ala Lys Asn Thr Val Asp
65                  70                  75                  80
```

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Glu Val Gln Leu Glu Glu Ser Gly Gly Ser Val Gln Thr Gly Gly
145                 150                 155                 160

Ser Leu Arg Leu Thr Cys Ala Ala Ser Gly Arg Thr Ser Arg Ser Tyr
                165                 170                 175

Gly Met Gly Trp Phe Arg Gln Ala Pro Gly Lys Glu Arg Glu Phe Val
            180                 185                 190

Ser Gly Ile Ser Trp Arg Gly Asp Ser Thr Gly Tyr Ala Asp Ser Val
        195                 200                 205

Lys Gly Arg Phe Thr Ile Ser Arg Asp Asn Ala Lys Asn Thr Val Asp
    210                 215                 220

Leu Gln Met Asn Ser Leu Lys Pro Glu Asp Thr Ala Ile Tyr Tyr Cys
225                 230                 235                 240

Ala Ala Ala Ala Gly Ser Ala Trp Tyr Gly Thr Leu Tyr Glu Tyr Asp
                245                 250                 255

Tyr Trp Gly Gln Gly Thr Gln Val Thr Val Ser Ser Gly Gly Gly Gly
            260                 265                 270

Ser Gly Gly Gly Gly Ser Gly Gly Gly Ser Gly Gly Gly Gly Ser
        275                 280                 285

Glu Val Gln Leu Val Glu Ser Gly Gly Gly Leu Val Gln Pro Gly Asn
    290                 295                 300

Ser Leu Arg Leu Ser Cys Ala Ala Ser Gly Phe Thr Phe Ser Ser Phe
305                 310                 315                 320

Gly Met Ser Trp Val Arg Gln Ala Pro Gly Lys Gly Leu Glu Trp Val
                325                 330                 335

Ser Ser Ile Ser Gly Ser Gly Ser Asp Thr Leu Tyr Ala Asp Ser Val
            340                 345                 350

Lys Gly Arg Phe Thr Ile Ser Arg Asp Asn Ala Lys Thr Thr Leu Tyr
        355                 360                 365

Leu Gln Met Asn Ser Leu Arg Pro Glu Asp Thr Ala Val Tyr Tyr Cys
    370                 375                 380

Thr Ile Gly Gly Ser Leu Ser Arg Ser Ser Gln Gly Thr Leu Val Thr
385                 390                 395                 400

Val Ser Ser Gly Gly Cys
            405

<210> SEQ ID NO 31
<211> LENGTH: 409
<212> TYPE: PRT
<213> ORGANISM: Artificial Sequence
<220> FEATURE:
<223> OTHER INFORMATION: cysteine comprising

<400> SEQUENCE: 31

Glu Val Gln Leu Glu Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
 50                  55                  60

Lys Gly Arg Phe Thr Ile Ser Arg Asp Asn Ala Lys Asn Thr Val Asp
 65                  70                  75                  80

Leu Gln Met Asn Ser Leu Lys Pro Glu Asp Thr Ala Ile Tyr Tyr Cys
                 85                  90                  95

Ala Ala Ala Ala Gly Ser Ala Trp Tyr Gly Thr Leu Tyr Glu Tyr Asp
            100                 105                 110

Tyr Trp Gly Gln Gly Thr Gln Val Thr Val Ser Ser Gly Gly Gly Gly
            115                 120                 125

Ser Gly Gly Gly Gly Ser Gly Gly Gly Ser Gly Gly Gly Gly Gly Ser
            130                 135                 140

Glu Val Gln Leu Val Glu Ser Gly Gly Gly Leu Val Gln Ala Gly Gly
145                 150                 155                 160

Ser Leu Arg Leu Ser Cys Ala Ala Ser Gly Arg Thr Phe Ser Ser Tyr
                165                 170                 175

Ala Met Gly Trp Phe Arg Gln Ala Pro Gly Lys Glu Arg Glu Phe Val
            180                 185                 190

Val Ala Ile Asn Trp Ser Ser Gly Ser Thr Tyr Tyr Ala Asp Ser Val
            195                 200                 205

Lys Gly Arg Phe Thr Ile Ser Arg Asp Asn Ala Lys Asn Thr Met Tyr
            210                 215                 220

Leu Gln Met Asn Ser Leu Lys Pro Glu Asp Thr Ala Val Tyr Tyr Cys
225                 230                 235                 240

Ala Ala Gly Tyr Gln Ile Asn Ser Gly Asn Tyr Asn Phe Lys Asp Tyr
            245                 250                 255

Glu Tyr Asp Tyr Trp Gly Gln Gly Thr Gln Val Thr Val Ser Ser Gly
            260                 265                 270

Gly Gly Gly Ser Gly Gly Gly Gly Ser Gly Gly Gly Ser Gly Gly Gly
            275                 280                 285

Gly Gly Ser Glu Val Gln Leu Val Glu Ser Gly Gly Gly Leu Val Gln
            290                 295                 300

Pro Gly Asn Ser Leu Arg Leu Ser Cys Ala Ala Ser Gly Phe Thr Phe
305                 310                 315                 320

Ser Ser Phe Gly Met Ser Trp Val Arg Gln Ala Pro Gly Lys Gly Leu
                325                 330                 335

Glu Trp Val Ser Ser Ile Ser Gly Ser Gly Ser Asp Thr Leu Tyr Ala
            340                 345                 350

Asp Ser Val Lys Gly Arg Phe Thr Ile Ser Arg Asp Asn Ala Lys Thr
            355                 360                 365

Thr Leu Tyr Leu Gln Met Asn Ser Leu Arg Pro Glu Asp Thr Ala Val
            370                 375                 380

Tyr Tyr Cys Thr Ile Gly Gly Ser Leu Ser Arg Ser Ser Gln Gly Thr
385                 390                 395                 400

Leu Val Thr Val Ser Ser Gly Gly Cys
                405

<210> SEQ ID NO 32
<211> LENGTH: 115
<212> TYPE: PRT
<213> ORGANISM: Artificial Sequence
<220> FEATURE:
<223> OTHER INFORMATION: cysteine comprising

<400> SEQUENCE: 32

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 33
<211> LENGTH: 115
<212> TYPE: PRT
<213> ORGANISM: Artificial Sequence
<220> FEATURE:
<223> OTHER INFORMATION: cysteine comprising

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 34
<211> LENGTH: 116
<212> TYPE: PRT
<213> ORGANISM: Artificial Sequence
<220> FEATURE:
<223> OTHER INFORMATION: cysteine comprising

<400> SEQUENCE: 34

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45
```

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
                100                 105                 110

Val Ser Ser Ala
        115

<210> SEQ ID NO 35
<211> LENGTH: 116
<212> TYPE: PRT
<213> ORGANISM: Artificial Sequence
<220> FEATURE:
<223> OTHER INFORMATION: cysteine comprising

<400> SEQUENCE: 35

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
                100                 105                 110

Val Ser Ser Ala
        115

<210> SEQ ID NO 36
<211> LENGTH: 115
<212> TYPE: PRT
<213> ORGANISM: Artificial Sequence
<220> FEATURE:
<223> OTHER INFORMATION: cysteine comprising

<400> SEQUENCE: 36

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr

Val Ser Ser
    115

<210> SEQ ID NO 37
<211> LENGTH: 116
<212> TYPE: PRT
<213> ORGANISM: Artificial Sequence
<220> FEATURE:
<223> OTHER INFORMATION: cysteine comprising

<400> SEQUENCE: 37

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
    115

<210> SEQ ID NO 38
<211> LENGTH: 115
<212> TYPE: PRT
<213> ORGANISM: Artificial Sequence
<220> FEATURE:
<223> OTHER INFORMATION: cysteine comprising

<400> SEQUENCE: 38

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
    115

<210> SEQ ID NO 39
<211> LENGTH: 116
<212> TYPE: PRT
<213> ORGANISM: Artificial Sequence
<220> FEATURE:

<223> OTHER INFORMATION: cysteine comprising

<400> SEQUENCE: 39

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 40
<211> LENGTH: 117
<212> TYPE: PRT
<213> ORGANISM: Artificial Sequence
<220> FEATURE:
<223> OTHER INFORMATION: cysteine comprising

<400> SEQUENCE: 40

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 41
<211> LENGTH: 118
<212> TYPE: PRT
<213> ORGANISM: Artificial Sequence
<220> FEATURE:
<223> OTHER INFORMATION: cysteine comprising

<400> SEQUENCE: 41

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val

```
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Gln Gly Thr Leu Val Thr
                100                 105                 110

Val Ser Ser Ala Ala Ala
        115

<210> SEQ ID NO 42
<211> LENGTH: 116
<212> TYPE: PRT
<213> ORGANISM: Artificial Sequence
<220> FEATURE:
<223> OTHER INFORMATION: cysteine comprising

<400> SEQUENCE: 42

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Gln Gly Thr Leu Val Thr
                100                 105                 110

Val Ser Ser Gly
        115

<210> SEQ ID NO 43
<211> LENGTH: 117
<212> TYPE: PRT
<213> ORGANISM: Artificial Sequence
<220> FEATURE:
<223> OTHER INFORMATION: cysteine comprising

<400> SEQUENCE: 43

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95
```

-continued

```
Thr Ile Gly Gly Ser Leu Ser Arg Ser Ser Gln Gly Thr Leu Val Thr
            100                 105                 110

Val Ser Ser Gly Gly
        115

<210> SEQ ID NO 44
<211> LENGTH: 118
<212> TYPE: PRT
<213> ORGANISM: Artificial Sequence
<220> FEATURE:
<223> OTHER INFORMATION: cysteine comprising

<400> SEQUENCE: 44

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115
```

CYSTEINE LINKED NANOBODY DIMERS

RELATED APPLICATIONS

This application is a national stage filing under 35 U.S.C. § 371 of International Application No. PCT/EP2015/080536, filed Dec. 18, 2015, and claims the benefit under 35 U.S.C. § 119(e) of U.S. Provisional Application Ser. No. 62/140,611, filed Mar. 31, 2015 and U.S. Provisional Application Ser. No. 62/094,179, filed Dec. 19, 2014, the entire contents of each of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 26, 2017, is named A084870176US02-SEQ-JRV.txt, and is 34,170 bytes in size.

FIELD OF THE INVENTION

The present invention relates to dimers comprising a first polypeptide and a second polypeptide, wherein each of said first and second polypeptide comprises at least one immunoglobulin single variable domain (ISVD) and a C-terminal extension comprising a cysteine moiety (preferably at the C-terminus), wherein said first polypeptide and said second polypeptide are covalently linked via a disulfide bond between the cysteine moiety of said first polypeptide and the cysteine moiety of said second polypeptide, in which the dimer outperformed the benchmark constructs, e.g. cognate multivalent and multispecific constructs, in various assays. The present invention provides methods for making the dimers of the invention. The present invention further provides variable domains (as defined herein) and polypeptides comprising one or more variable domains (also referred to as "polypeptides of the invention") obtainable by the methods of the present invention, as well as compounds (also referred to as "compounds of the invention") that comprise such variable domains and/or polypeptides coupled to one or more groups, residues or moieties.

The invention also relates to nucleic acids encoding such variable domains and/or polypeptides; to host cells comprising such nucleic acids and/or expressing or capable of expressing such variable domains and/or polypeptides; to compositions, and in particular to pharmaceutical compositions, that comprise such variable domains and/or polypeptides, compounds, nucleic acids and/or host cells; and to uses of such variable domains, polypeptides, nucleic acids, host cells and/or compositions, in particular for prophylactic, therapeutic or diagnostic purposes.

Other aspects, embodiments, advantages and applications of the invention will become clear from the further description herein.

BACKGROUND

With more than 20 monoclonal antibodies (mAbs) approved for therapy, and many more in clinical development, this class of molecules has become an established treatment modality for a variety of diseases (Reichert (2011) MAbs 3:76-99; Nelson et al. (2010) Nat Rev Drug Discov 9:767-74). However, complex diseases such as cancer or inflammatory disorders are usually multifactorial in nature, involving a redundancy of disease-mediating ligands and receptors, as well as crosstalk between signal cascades. Blockade of multiple targets or multiple sites on one target should result in improved therapeutic efficacy. The limited ability of conventional monoclonal antibody therapies to induce significant anti-tumour activity has led to the development of bispecifics; antibodies that can simultaneously bind two different antigens (Kontermann (2012) mAbs 4:182-197). During the past decade, dual targeting with bispecific antibodies has emerged as an alternative to combination therapy or use of mixtures. The concept of dual targeting with bispecific antibodies is based on the targeting of multiple disease-modifying molecules with one drug. From a technological and regulatory perspective, this makes development less complex because manufacturing, preclinical and clinical testing is reduced to a single, bispecific molecule (Kontermann (2012) supra). Therapy with a single dual-targeting drug rather than combinations should also be less complicated for patients.

Bispecific antibodies can be generated via biochemical or genetic means. Recombinant technologies have produced a diverse range of bispecific antibodies, generating 45 formats in the last two decades (Byrne et al (2013) Trends Biotechnol. 31, 621-32). Despite this variety of topologies, the approach is not suited to every protein combination. The fusion of proteins via their N- or C-termini can result in a reduction or loss of bioactivity and variable expression yields can be observed due to complications in folding and processing (Schmidt (2009) Curr. Opin. Drug Discovery Dev. 12, 284-295; Baggio et al. (2004) Diabetes 53, 2492-2500; Chames and Baty (2009) mAbs 1, 539-47).

An alternative approach to generating bispecific therapeutics is chemical conjugation using homo- or hetero-bifunctional coupling reagents (Doppalapudi et al. (2010) Proc Natl Acad Sci USA 107:22611-6). Until now, this has been a less successful method of producing such conjugates. A fundamental flaw in the chemical techniques employed in this area has been their dependency on modifying lysine residues. There is an average of 100 lysine residues per conventional antibody, and their distribution is uniform throughout the surface topology of the antibody or fragments thereof, such as, Fab, Fc and immunoglobulin single variable domain (ISVD) regions. As such, conjugation techniques using lysine residues will randomly cross-link to virtually all areas of the antibody molecule, resulting in a highly heterogeneous mixture of products with unpredictable properties.

A strategy to overcome this issue is provided by insertion of unnatural amino acids, which allow the site-specific introduction of chemical linkers. However, substitution for the unnatural amino acid is often incomplete, and expression yields are generally low due to the cellular toxicity of artificial amino acids at the high concentrations necessary.

Another approach to overcome the problems with random cross-linking is provided by site-directed mutagenesis, in which a single nucleophilic cysteine residue is introduced at a desired site in an antibody. Cysteine residues have a low natural abundance in proteins, but are often found tied up in intramolecular disulfide bonds, providing structure and functional integrity, because of which free cysteine residues are lacking in antibodies and antibody fragments (Fodje and Al-Karadaghi (2002) Protein Eng. Des. Sel. 15, 353-358). However, the control of intra- versus intermolecular cross-linking is very difficult to achieve with these reagents. Some control can be achieved through appropriate choice of reaction parameters such as protein/reagent ratio, pH, ionic strength etc., but the results remain unsatisfactory.

WO2004/03019 hypothesizes that variable domains may be linked together to form multivalent ligands by for example provision of dAbs each with a cysteine at the C-terminus of the domain, the cysteines being disulphide bonded together, using a chemical coupling procedure using 2,2'-dithiodipyridine (2,2'-DTDP) and a reduced monomer. However, 2,2'-DTDP is an irritant limiting its practical use. In addition, its use is further limited since 2,2'-DTDP is also a reactive disulfide that mobilizes $Ca^{2+}$ from cells. Not only is WO2004/03019 silent whether this method is actually feasible, especially without disturbing and rearranging intramolecular thiol-bonds, but in view of the properties of 2,2'-DTDP, laborious measures have to be taken to completely remove this agent.

Baker et al. (2014, Bioconjugate Chem., DOI: 10.1021/bc5002467) describes a bispecific antibody construct through reduction and bridging of antibody fragment disulfide bonds, using a synthesized bis-dibromomaleimide cross linker.

Carlsson et al. (1978 Biochem J. 173:723-737) proposes a thiolation procedure for proteins using n-succinimidyl 3-(2-pyridyldithio)propionate resulting in reversible protein-protein conjugation. The procedure however requires extensive purification. In addition, decreased activity has been reported when following the protocol (Carlsson et al., 1978). Carlsson et al. (1978) is silent whether the procedure can be used for antibodies or fragments thereof.

In general, intermolecular cross-linking via the introduction of cysteine residues is limited, as cysteine mutagenesis commonly leads to reduced expression yields and undesirable properties such as susceptibility to unwanted dimerisation, mixed disulfide formation or disulfide scrambling (Schmiedl et al. (2000) J. Immunol. Methods 242, 101-14; Junutula et al. (2008) Nat. Biotechnol. 26, 925-32; Albrecht et al. (2004) Bioconjugate Chem. 15, 16-26).

Graziano and Guptill discuss methods for creating Fab' x Fab' chemically linked bispecifics via the use of free thiols generated upon reduction of interheavy chain disulfide bonds of the F(ab')2 fragments. However, the conditions must be chosen such that efficient reduction of the inter-heavy chain disulfides is achieved without extensive reduction of heavy-light chain disulfide bonds. It was noted that bispecifics created using the o-phenylenedimaleimide (o-PDM) method may be more stable than those generated by Ellman's reagent (5,5'-dithiobis-(2-nitrobenzoic acid) or DTNB), but it was more difficult to purify o-PDM-generated bispecifics to biochemical homogeneity. Another distinct disadvantage of the o-PDM method is the necessity to have an odd number of inter-heavy chain disulfide bonds in the antibody molecule to be maleimidated (Graziano and Guptill (2004) Chapter 5 Chemical Production of Bispecific Antibodies pages 71-85 From: Methods in Molecular Biology, vol. 283: Bioconjugation Protocols: Strategies and Methods; Edited by: C. M. Niemeyer © Humana Press Inc., Totowa, N.J.) This prevents its application in the construction of human-human bispecifics.

A further strategy to improve treatment, especially cancer treatment, is to use antibody drug conjugates (ADCs). Although there are currently over 50 distinct ADCs in clinical trials, several of which are active, extensive problems remain in developing, purifying and preventing toxicity of ADCs. First of all, there is little control over the physicochemical properties, such as heterogeneity of the ADCs due to the number of drugs conjugated per antibody, the PK/biodistribution, the payload and the delivery vehicle. For instance, many drugs are conjugated via lysines to antibodies. As mentioned above, since lysines are scattered all over an antibody, this gives rise to a difficult to control drug-to-antibody ratio. In addition, this coupling interferes with the bispecific concept making use of lysine coupling as well. Moreover, most drugs used in cancer treatment are very hydrophobic, resulting in an unpredictable and mostly unfavorable aggregation, PK and biodistribution profile of the ADC moiety. This is especially true for small antibody fragments. Conventional antibodies have a size of about 150 kD, while the drugs have on average a size of about 1 kD. Hence, the size ratio of antibody:drug is about 150:1. In vast contrast to a conventional antibody, an antibody fragment, such as an ISVD has a size of only about 15 kD. Consequently, the size ratio of ISVD:drug is only 15:1, i.e. 10 times less than for conventional antibodies. Accordingly, the hydrophobic characteristics of a drug have a disproportionately larger influence on the physic-chemical properties of the conjugated antibody fragment. Indeed, a main problem with conjugated antibody fragments is aggregation (Feng et al. 2014 Biomedicines 2:1-13). Analyses further suggest that IgG-sized macromolecular constructs exhibit a favorable balance between systemic clearance and vascular extravasation, resulting in maximal tumor uptake (Dane Wittrup et al. 2012 Methods Enzym. 503 Chapter 10, pp 255-268). These difficulties effectively limit the use of conjugating drugs to smaller antibody fragments.

Epidermal growth factor receptor (EGFR; also called HER-1) is a member of the HER-kinase family, together with HER-2, HER-3, and HER-4. EGFR is overexpressed in a variety of human tumors including non-small cell lung cancer, breast, head and neck, gastric, colorectal, esophageal, prostate, bladder, renal, pancreatic, and ovarian cancers. Activation of EGFR causes signaling that may lead to cell division, increased motility, angiogenesis and decreased apoptosis. These effects are mediated by a complex series of signaling mechanisms, such as engagement of the mitogen-activated protein kinase (MAPK) and phosphatidylinositol-3 kinase (PI3K) pathways.

EGFR has also been implicated in several other diseases, such as inflammatory arthritis and hypersecretion of mucus in the lungs.

Many of the EGFR targeting antibodies such as IMC-C225 (Erbitux, Imclone), EMD72000 (Merck Darmstadt), ABX-EGF (Abgenix), h-R3 (theraCIM, YM Biosciences) and Humax-EGFR (Genmab) were isolated as antibodies that prevent binding of ligand to the receptor. Yet none of these antibodies or the presently available drugs is completely effective for the treatment of cancer, and most are limited by severe toxicity.

SUMMARY OF THE INVENTION

It is an object of the present invention to overcome or ameliorate at least one of the disadvantages of the prior art, or to provide a useful alternative.

In view of their modularity, immunoglobulin single variable domains (ISVDs) and especially Nanobodies are exceptionally suited for combining into multivalent constructs. A convenient and preferred manner to generate multivalent constructs is by genetic fusion of individual nucleic acids encoding ISVDs via amide bonds, in which a nucleotide sequence encoding an ISVD is coupled via its 3'-terminus nucleic acid to the 5'-terminus nucleic acid of another nucleotide sequence encoding ISVD, if necessary via (nucleic acid) linkers of various lengths. Hence, the ISVDs are coupled via amide bonds, possibly via peptide linkers.

ISVDs comprise intramolecular disulfide bonds between cysteines in order to maintain the integrity and functionality of the moiety. It has been demonstrated extensively that after genetic fusion of nucleotide sequences encoding ISVDs, the intrinsic property to form canonical (also designated as intramolecular) disulfide bonds is not affected in the individual ISVDs upon translation.

In view of the ease and versatility of genetic fusion, chemical conjugation of ISVDs is not a preferred method, especially since it requires arduous methods to selectively couple ISVDs at a predetermined site, not hindering intramolecular disulfide bonds and/or uses non-self, potentially hazardous components.

The present invention provides a convenient method in which intermolecular dimerization via disulfide bonds between two polypeptides is facilitated, without substantially any aberrant disturbance or involvement of intramolecular disulfide bonds of ISVDs. This method uses the introduction of a cysteine in the C-terminal extension of a polypeptide further comprising ISVDs.

The present invention also provides methods for making the dimers of the invention. In particular, the present invention relates to a method for making (polypeptide-)dimers, comprising at least the steps of:
(i) providing a first polypeptide, wherein said first polypeptide comprises
   at least one immunoglobulin single variable domain (ISVD) and
   a C-terminal extension comprising a cysteine moiety, preferably at the C-terminus;
(ii) providing a second polypeptide, wherein said second polypeptide comprises
   at least one immunoglobulin single variable domain (ISVD) and
   a C-terminal extension comprising a cysteine moiety, preferably at the C-terminus; and
(iii) oxidizing the thiol moiety of said cysteine moiety at the C-terminal extension of said first polypeptide and the thiol moiety of said cysteine moiety at the C-terminal extension of said second polypeptide, optionally by adding oxidizing copper ions (Ce), and preferably at pH 6.5 to pH 7.5 to a disulfide derivative cystine; and said cystine is the only intermolecular disulfide bond present in the dimer; thereby making said dimers.

Preferably, the step of reducing said [C-terminal] cystine of said dimer is performed under conditions wherein intramolecular disulfide bonds of said first polypeptide and/or said second polypeptide remain oxidized. In other words, the integrity of the ISVDs is maintained. The method optionally further comprised the step of reducing said (C-terminally located) cystine of said dimer.

It was further surprisingly found that the dimers of the invention outperformed the benchmark constructs, e.g. cognate multivalent and multispecific constructs, in various assays. The benchmark constructs consist of the same polypeptides as the dimers of the present invention, but the benchmark constructs were generated by genetic fusion of nucleic acids encoding these polypeptides, because of which a first polypeptide is coupled to a second polypeptide via amide bonds in an N-terminal to C-terminal direction. In particular, the dimers of the invention can bind to a target with an affinity (suitably measured and/or expressed as a $K_D$-value (actual or apparent), a $K_A$-value (actual or apparent), a $k_{on}$-rate and/or a $k_{off}$-rate better than the benchmark, e.g. cognate bivalent constructs. On the other hand, the dimers of the invention, even when containing two albumin binding ISVDs, showed a similar biodistribution profile as the benchmark which contains only one albumin binding ISVD. Moreover, the dimers of the invention showed unexpectedly an improved internalization compared to the benchmark constructs, especially on cells with low target expression. As internalization is crucial for good efficacy; improved internalization likely will lead to better efficacy. Moreover, an improved internalization can reduce side effects, such as toxicity, since less drug is needed and less drug will disengage from the target. Internalization of the dimers on cells with low target expression can broaden the range of tumors accessible to treatment and decrease the chances of developing drug resistance. On the other hand, the dimers of the invention showed a similar, favorable biodistribution profile as the benchmark constructs.

Accordingly, the present invention relates to a dimer comprising a first polypeptide and a second polypeptide, wherein said first polypeptide comprises at least one immunoglobulin single variable domain (ISVD) and a C-terminal extension comprising a cysteine moiety (preferably at the C-terminus); wherein said second polypeptide comprises at least one immunoglobulin single variable domain (ISVD) and a C-terminal extension comprising a cysteine moiety (preferably at the C-terminus); and wherein said first polypeptide and said second polypeptide are covalently linked via a disulfide bond between the cysteine moiety of said first polypeptide and the cysteine moiety said second polypeptide.

As such, the present invention relates to a (polypeptide) dimer comprising a first polypeptide and a second polypeptide, wherein said first polypeptide and said second polypeptide are covalently linked via a C-terminally located disulfide bond.

The inventors further observed that the dimers of the invention have unexpected favourable binding and functional characteristics. These characteristics were also retained for prolonged periods of time, without any apparent or substantive loss of potency. This makes the dimers useful for storage and transport. Accordingly, the present invention further relates to a method for storing polypeptides comprising reactive cysteine moieties, comprising at least the step of oxidizing the thiol moiety of said reactive cysteine moiety to the disulfide derivative cystine, thereby temporarily inactivating said reactive cysteine moieties, wherein said polypeptides further comprise (internal) cystine bonds.

The present inventors hypothesized that the dimers might be particularly suited as a pool for instantaneous use, such as, for instance, coupling of functional groups using the C-terminal cysteine, e.g. by maleimide chemistry. A protocol with mild reducing conditions was developed, in which the intermolecular disulfide bridge of the dimer was reduced to activate the thiol group of the constituent polypeptides. Optimized conditions resulted in reduction of the disulfide forming the dimer without reducing the internal canonical ISVD disulfide bridges. Accordingly, the present invention relates to a method for generating polypeptides comprising reactive cysteine moieties, comprising at least the steps of:
(i) providing polypeptides dimerized via a cystine bond;
(ii) reducing said cystine bond;

thereby generating polypeptides comprising reactive cysteine moieties. Preferably, said cystine bond is located at the C-terminal end of said polypeptides. Preferably, the reducing conditions of said step (ii) are chosen such that the internal cystine bonds are not reduced.

In addition, the present invention also provides methods for conjugating payloads to the polypeptides of the invention, with a very controlled drug-to-antibody ratio (DAR) and a purity over 95%. Completely unexpectedly, conjugating the polypeptide with a payload (DAR=1) has no effect on the biodistribution profile. Moreover, these conjugated polypeptides demonstrated in vitro cell toxicity and in vivo inhibition of tumor growth. Accordingly, the present invention provides methods for treating subjects using the polypeptides of the invention.

FIGURE LEGENDS

FIG. 1 Schematic depiction of constructs used.

FIG. 2 Competition binding FACS.

FIG. 3 Blocking of EGF mediated EGFR phosphorylation on HER14 cells (0.5 mM EGF).

Figure 4:
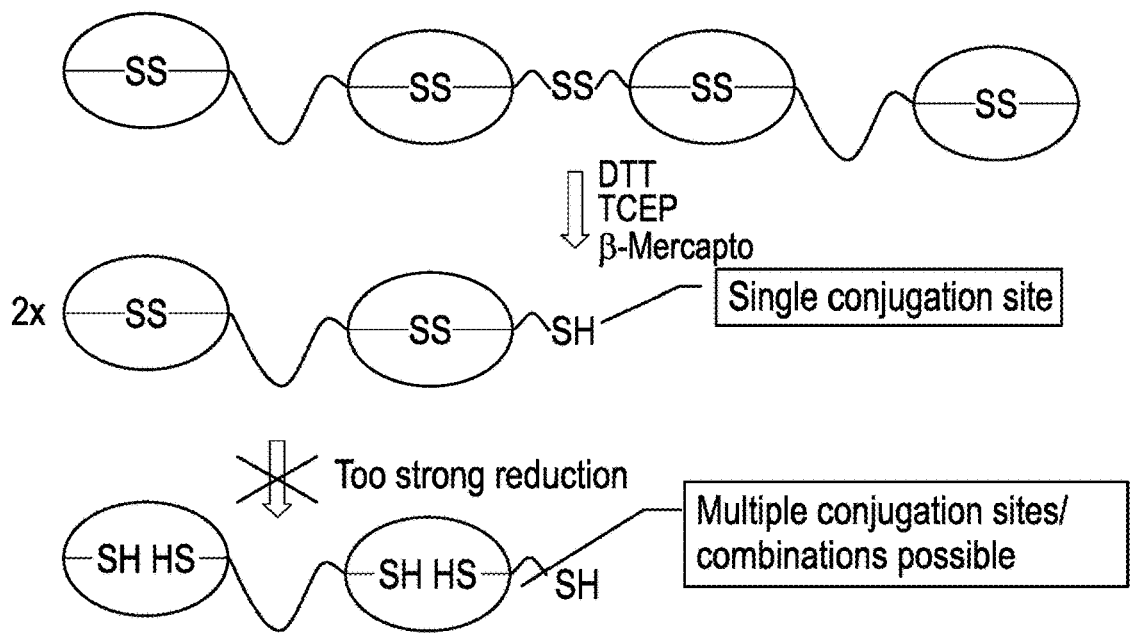

FIG. 4 Schematic representation of the reduction of disulfide dimers of C-terminal GGC-extended polypeptides.

Figure 5:
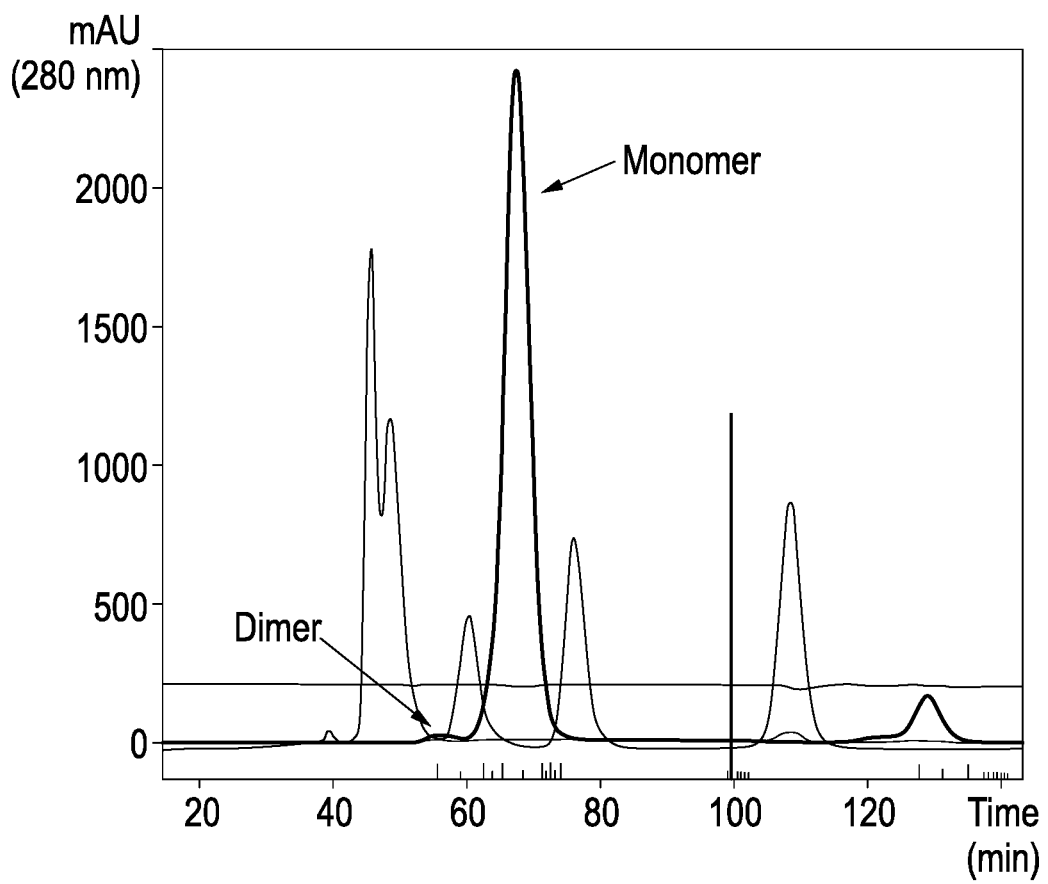

FIG. 5 SEC profile of reduced cysteine extended polypeptides.

Figure 6:
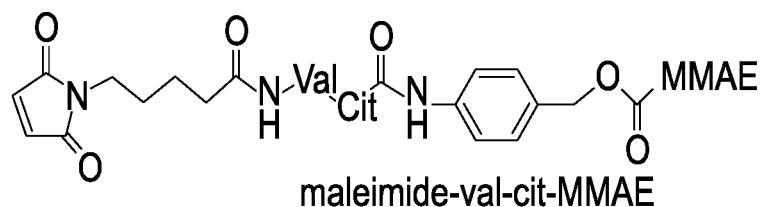

FIG. 6 Maleimide-val-cit-M MAE.

Figure 7:
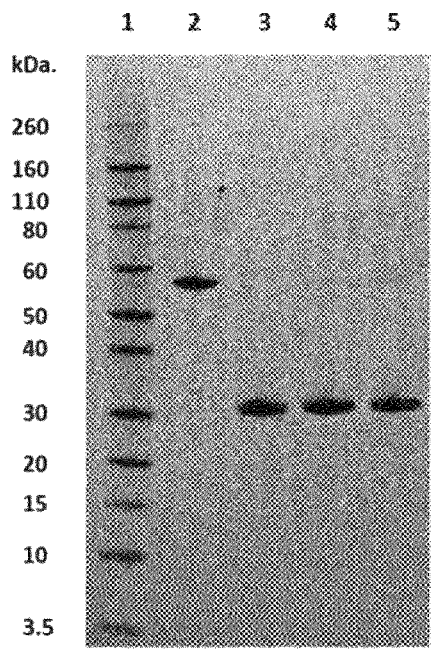

FIG. 7 SDS-PAGE Analysis of T0238-00001-mc-val-cit-PAB-M MAE (ABL100-NC003-1). 1) Novex Markers; 2) T0238-00001 dimer; 3) reduced T0238-00001 (10 mM DTT, 2-8° C., 0/N); 4) ABL100-NC003-1 crude conjugation mixture; 5) ABL100-NC003-1.

Figure 8:
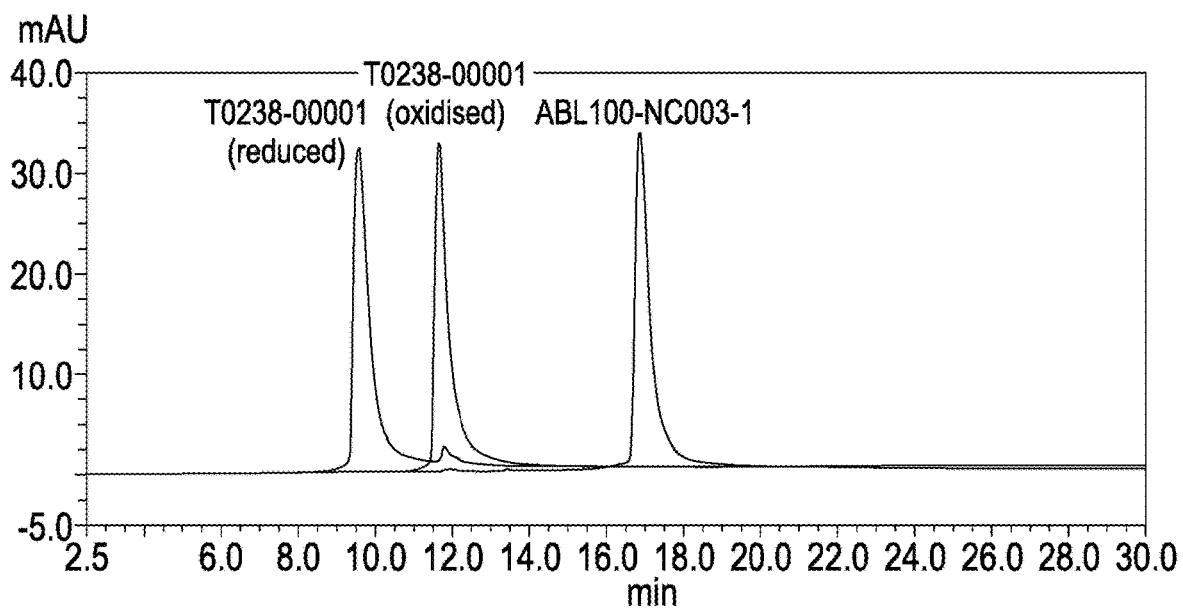

FIG. 8 Overlaid hydrophobic interaction chromatograms for reduced T023800001-A, oxidised T23800001-A and T0238-00001-mc-val-cit-PAB-M MAE.

Figure 9:
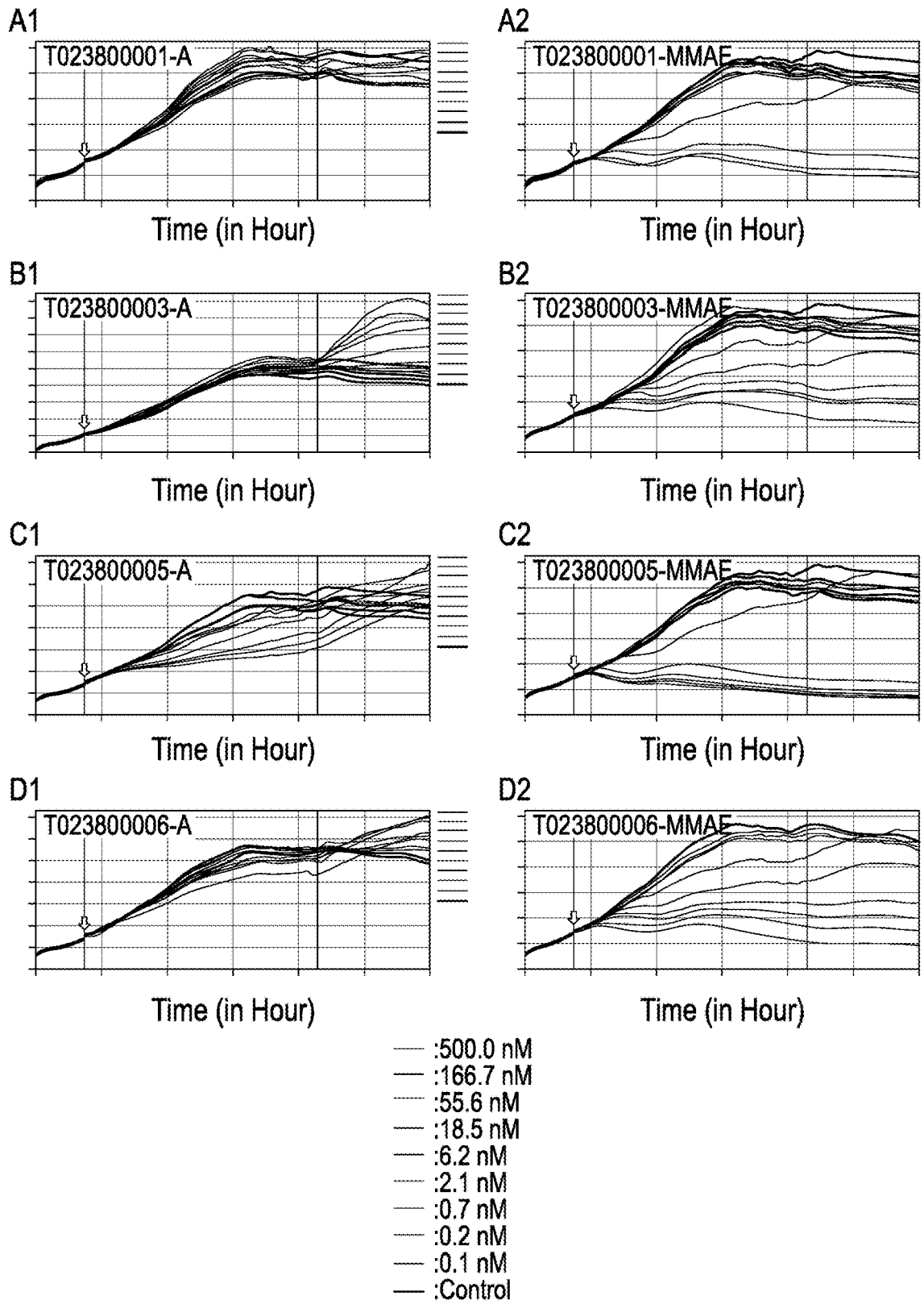

FIG. 9 In vitro cell killing of Polypeptide-MMAE conjugates: impedimetric monitoring of the effect of different concentrations of non-conjugated Nanobodies (panels A1, B1, C1, and D1) and conjugated Nanobodies (panels A2, B2, C2, and D2) on proliferation of MDA-MB-468 cells, measured as fluctuations in normalized cell index (CI). The arrow indicates the time-point of Nanobody administration (i.e. 20 h after seeding) and the dotted line indicates the end-point (i.e. 116 h post seeding) for data analysis. The cell index obtained from the cell growth in absence of Nanobody is taken as control.

FIG. 10 Dose-dependent effect of the non-conjugated and MMAE-conjugated polypeptides.

FIG. 11 In vivo efficacy of polypeptide-M MAE conjugates.

FIG. 12 Modification and radiolabeling of Nbs using NCS-Bz-Df and $^{89}$Zr.

FIG. 13 Averaged % ID/g for 3 polypeptides.

FIG. 14 Dose-response curve of internalized polypeptides and constructs.

DETAILED DESCRIPTION OF THE INVENTION

Any discussion of the prior art throughout the specification should in no way be considered as an admission that such prior art is widely known or forms part of common general knowledge in the field.

Unless indicated or defined otherwise, all terms used have their usual meaning in the art, which will be clear to the skilled person. Reference is for example made to the standard handbooks, such as Sambrook et al. "Molecular Cloning: A Laboratory Manual" (2nd. Ed.), Vols. 1-3, Cold Spring Harbor Laboratory Press (1989); F. Ausubel et al. eds., "Current protocols in molecular biology", Green Publishing and Wiley Interscience, New York (1987); Lewin "Genes II", John Wiley & Sons, New York, N.Y., (1985); Old et al. "Principles of Gene Manipulation: An Introduction to Genetic Engineering", 2nd edition, University of California Press, Berkeley, Calif. (1981); Roitt et al. "Immunology" (6th. Ed.), Mosby/Elsevier, Edinburgh (2001); Roitt et al. Roitt's Essential Immunology, 10$^{th}$ Ed. Blackwell Publishing, U K (2001); and Janeway et al. "Immunobiology" (6th Ed.), Garland Science Publishing/Churchill Livingstone, New York (2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews: Presta 2006 (Adv. Drug Deliv. Rev. 58 (5-6): 640-56), Levin and Weiss 2006 (Mol. Biosyst. 2(1): 49-57), Irving et al. 2001 (J. Immunol. Methods 248(1-2): 31-45), Schmitz et al. 2000 (Placenta 21 Suppl. A: S106-12), Gonzales et al. 2005 (Tumour Biol. 26(1): 31-43), which describe techniques for protein engineering, such as affinity maturation and other techniques for improving the specificity and other desired properties of proteins such as immunoglobulins.

A nucleic acid sequence or amino acid sequence is considered to be "(in) essentially isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatography technique, such as polyacrylamide-gel electrophoresis.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

For instance, when a nucleotide sequence, amino acid sequence or polypeptide is said to "comprise" another nucleotide sequence, amino acid sequence or polypeptide, respectively, or to "essentially consist of" another nucleotide sequence, amino acid sequence or polypeptide, this may mean that the latter nucleotide sequence amino acid sequence or polypeptide has been incorporated into the first mentioned nucleotide sequence, amino acid sequence or polypeptide, respectively, but more usually this generally means that the first mentioned nucleotide sequence, amino acid sequence or polypeptide comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist or" or "consist essentially of" and the like is meant that the polypeptide used herein either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

An amino acid sequence (such as an immunoglobulin single variable domain, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy (DG) of binding by the well-known relation $DG=RT \cdot \ln(K_D)$ (equivalently $DG=-RT \cdot \ln(K_A)$), where R equals the gas constant, T equals the absolute temperature and ln denotes the natural logarithm.

The $K_D$ for biological interactions which are considered meaningful (e.g. specific) are typically in the range of $10^{10}$M (0.1 nM) to $10^5$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation of second). The on-rate $k_{on}$ has units $M^{-1}s^{-1}$. The on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ $s^{-1}$ (near irreversible complex with a $t_{1/2}$ of multiple days) to 1 $s^{-1}$ ($t_{1/2}$=0.69 s).

Specific binding of an antigen-binding protein, such as an ISVD, to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® instruments (Pharmacia Biosensor AB, Uppsala, Sweden). Kinetic Exclusion Assay (KINEXA®) (Drake et al. 2004, Analytical Biochemistry 328: 35-43) measures binding events in solution without labeling of the binding partners and is based upon kinetically excluding the dissociation of a complex.

The GYROLAB® immunoassay system provides a platform for automated bioanalysis and rapid sample turnaround (Fraley et al. 2013, Bioanalysis 5: 1765-74).

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as a dimer or polypeptide of the invention) molecule can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the immunoglobulin single variable domains, and/or polypeptides of the invention) will bind to their antigen with a dissociation constant ($K_0$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{-12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ liter/mol) is generally considered to indicate non-specific binding. Preferably, a monovalent immunoglobulin single variable domain of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

Another approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D,ref}$ the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D,ref})$. Note that if $c_{ref} \ll K_{D,ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

The half maximal inhibitory concentration ($IC_{50}$) is a measure of the effectiveness of a compound in inhibiting a biological or biochemical function, e.g. a pharmacological effect. This quantitative measure indicates how much of the ISV or Nanobody (inhibitor) is needed to inhibit a given biological process (or component of a process, i.e. an enzyme, cell, cell receptor, chemotaxis, anaplasia, metastasis, invasiveness, etc.) by half. In other words, it is the half maximal (50%) inhibitory concentration (IC) of a substance (50% IC, or $IC_{50}$). The $IC_{50}$ of a drug can be determined by constructing a dose-response curve and examining the effect of different concentrations of antagonist such as the ISV or Nanobody of the invention on reversing agonist activity. $IC_{50}$ values can be calculated for a given antagonist such as the ISV or Nanobody of the invention by determining the concentration needed to inhibit half of the maximum biological response of the agonist.

The term half maximal effective concentration ($EC_{50}$) refers to the concentration of a compound which induces a response halfway between the baseline and maximum after a specified exposure time. In the present context it is used as a measure of a polypeptide's, ISV's or Nanobody's potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the examples section, the experiments were designed to reflect the KD as accurate as possible. In other words, the $EC_{50}$ values may then be considered as KD values. The term "average KD" relates to the average KD value obtained in at least 1, but preferably more than 1, such as at least 2 experiments. The term "average" refers to the mathematical term "average" (sums of data divided by the number of items in the data).

It is also related to $IC_{50}$ which is a measure of a compound's inhibition (50% inhibition). For competition binding assays and functional antagonist assays $IC_{50}$ is the most common summary measure of the dose-response curve. For agonist/stimulator assays the most common summary measure is the $EC_{50}$.

The term "genetic fusion" as used herein refers to the coupling of individual nucleic acids encoding ISVDs via amide bonds, in which a nucleotide sequence encoding an ISVD is coupled via its 3'-terminus nucleic acid via a phosphodiester bond to the 5'-terminus nucleic acid of another nucleotide sequence encoding an ISVD, if appropriate via (nucleic acid) linkers of various lengths, e.g. a nucleotide sequence encoding an ISVD is coupled via its 3'-terminus nucleic acid via a phosphodiester bond to the 5'-terminus nucleic acid of a linker sequence, which is coupled via its 3'-terminus nucleic acid via a phosphodiester bond to the 5'-terminus nucleic acid of another nucleotide sequence encoding an ISVD (i.e. the ISVDs and optionally the linkers are genetically fused). Genetic fusion can be performed according to standard recombinant DNA protocols (supra), or as described in the Examples section, e.g. Garaicoechea et al. (2008, J Virol. 82: 9753-9764).

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins and are listed in Table 1 below. Those amino acid sequences containing D-amino acids are not intended to be embraced by this definition. Any amino acid sequence that contains post-translationally modified amino acids may be described as the amino acid sequence that is initially translated using the symbols shown in the Table below with the modified positions; e.g., hydroxylations or glycosylations, but these modifications shall not be shown explicitly in the amino acid sequence. Any peptide or protein that can be expressed as a sequence modified linkages, cross links and end caps, non-peptidyl bonds, etc., is embraced by this definition.

TABLE 1

Common amino acids

| 1-Letter Code | 3-Letter Code | Name |
|---|---|---|
| A | Ala | Alanine |
| B | Asx | Aspartic acid or Asparagine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| J | Xle | Isoleucine or Leucine |
| K | Lys | Lysine |
| L | Leu | Leucine |
| M | Met | Methionine |
| N | Asn | Asparagine |
| O | Pyl | Pyrrolysine |
| P | Pro | Proline |
| Q | Gln | Glutamine |
| R | Arg | Arginine |
| S | Ser | Serine |
| T | Thr | Threonine |
| U | Scy | Selenocysteine |
| V | Val | Valine |
| W | Trp | Tryptophan |
| X | Xxx | Uncommon or Unspecified |
| Y | Tyr | Tyrosine |
| Z | Glx | Glutamic acid or Glutamine |

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptides and a protein; that polypeptides may be made by chemical synthesis or recombinant methods; and that proteins are generally made in vitro or in vivo by recombinant methods as known in the art.

To facilitate an understanding of the invention, a brief discussion of the terminology used in connection with the invention will be provided. By convention, the amide bond in the primary structure of polypeptides is in the order that the amino acids are written, in which the amine end (N-terminus) of a polypeptide is always on the left, while the acid end (C-terminus) is on the right.

The polypeptide of the invention comprises at least one immunoglobulin single variable domain (ISVD) and a C-terminal extension comprising a cysteine moiety, preferably at the C-terminus. In its simplest form, the polypeptide of the invention consists of one ISVD followed by (bonded to or conjugated with) a cysteine.

The C-terminal extension is present C-terminally of the last amino acid residue (usually a serine residue) of the last (most C-terminally located) ISVD, comprising a cysteine residue, preferably the cysteine moiety of the invention is present or positioned at the C-terminus of the C-terminal extension.

In the context of the present invention, the C-terminal extension consists of at least one amino acid, i.e. the cysteine moiety, or an amino acid sequence of at least two amino acid residues to maximal 50 amino acid residues comprising at least one cysteine residue present or positioned at the C-terminus of the C-terminal extension, preferably between 2 and 40 amino acid residues, such as between 2 and 30 amino acid residues, such as for instance, 2, 3, 4, 5, 6, 7, 8, 9, 10, 15 or 20 amino acid residues. For example, the C-terminal extension may consist of 1, 2, 3, 4, 5, 6, 7, 8, 9, 10, 11, 12, 13, 14 or 15 amino acid residues of which the amino acid located at the C-terminus is a cysteine moiety, such as, e.g. the C-terminal extension consists of only a cysteine residue; e.g. the C-terminal extension may consist of 1, 2, 3, 4, 5, 6, 7, 8, 9, 10, 11, 12, 13 or 14 amino acid residues followed by a cysteine moiety; e.g. the C-terminal extension may consist of 1, 2, 3, 4, 5, 6, 7, 8, 9, 10, 11, 12, 13 or 14 glycine residues followed by a cysteine moiety; e.g. the C-terminal extension may consist of 1, 2, 3, 4, 5, 6, 7, 8, 9, 10, 11, 12, 13 or 14 alanine residues followed by a cysteine moiety.

In another aspect, the cysteine residue is present or positioned at a site in the C-terminal extension which is different from the C-terminal end (C-terminus). For instance, the cysteine residue is present or positioned at the amino acid residue in front of (upstream of) the last amino acid residue of the C-terminal extension (i.e. the second last amino acid residue of the polypeptide of the invention) or at the amino acid residue in front of (upstream of) the last two amino acid residue of the C-terminal extension (i.e. the third last amino acid residue of the polypeptide of the invention). For example, the C-terminal extension may consist of 2, 3, 4, 5, 6, 7 or 8 amino acid residues (such as e.g. glycine or alanine) of which respectively the first, second, third, fourth, fifth, sixth or seventh amino acid residue is a cysteine (i.e. the second last amino acid residue of the polypeptide of the invention); or the C-terminal extension may consist of 3, 4, 5, 6, 7 or 8 amino acid residues (such as e.g. glycine or alanine) of which respectively the first, second, third, fourth, fifth or sixth amino acid residue is a cysteine (i.e. the third last amino acid residue of the polypeptide of the invention).

Preferred examples of C-terminal extensions are given in Table 2.

TABLE 2

C-terminal extensions

| SEQ ID NO | Amino acid sequence |
|---|---|
| 1 | C |
| 2 | GC |
| 3 | GGC |
| 4 | GGGC |
| 5 | GGGGC |
| 6 | AC |
| 7 | AAC |
| 8 | AAAC |
| 9 | AAAAC |
| 10 | CG |
| 11 | GCG |
| 12 | GGCG |
| 13 | GGGCG |

TABLE 2-continued

C-terminal extensions

| SEQ ID NO | Amino acid sequence |
|---|---|
| 14 | GGGGCG |
| 15 | GGGGCGGGG |

In an embodiment, the invention relates to a dimer as described herein, wherein said first polypeptide and/or said second polypeptide comprises a C-terminal extension of 50, 40, 30, 20, 10, 9, 8, 7, 6, 5, 4, 3, 2, or 1 amino acid residue(s) comprising a cysteine moiety, preferably at the C-terminus. In an embodiment, the present invention relates to a dimer as described herein, wherein said C-terminal extension consists of GlyGlyGlyCys (SEQ ID NO: 4), GlyGlyCys (SEQ ID NO: 3), GlyCys (SEQ ID NO: 2) or Cys (SEQ ID NO: 1).

In an embodiment, the invention relates to a dimer as described herein, wherein said polypeptide comprises a C-terminal extension chosen from the group consisting of SEQ ID NOs: 1-15.

The C-terminal extension can be coupled to an ISVD via any suitable technique known to the person skilled in the art, such as, for instance, by recombinant DNA techniques described supra for genetic fusion.

A polypeptide of the invention may comprise more than 1 ISVD, such as 2, 3, 4 or even more ISVDs. Accordingly, the present invention relates to a polypeptide of the invention comprising at least two ISVDs. Additionally, the present invention relates to a dimer comprising a first polypeptide and a second polypeptide as described herein, wherein said first polypeptide comprises at least two ISVDs and/or said second polypeptide comprises at least two ISVDs.

The ISVDs comprised in a polypeptide of the invention may be the same or different. In an embodiment, the ISVDs can bind the same the same target, irrespective of the ISVDs being the same or different. Accordingly, the present invention relates to a polypeptide of the invention, comprising identical ISVDs, ISVDs binding the same target, and/or ISVDs comprising the same CDR1, CDR2 and CDR3, respectively. In an embodiment, the ISVDs can bind different targets. In an embodiment, the present invention relates to a dimer comprising a first polypeptide and a second polypeptide as described herein, wherein said at least two ISVDs of said first polypeptide are identical and/or said at least two ISVDs of said second polypeptide are identical.

In a polypeptide of the invention, whether or not comprised in the dimer of the invention, the ISVDs can be directly linked or linked via a linker.

The relative affinities may depend on the location of the ISVDs in the polypeptide. It will be appreciated that the order of the ISVDs in a polypeptide of the invention (orientation) can be chosen according to the needs of the person skilled in the art. The order of the individual ISVDs as well as whether the polypeptide comprises a linker is a matter of design choice. Some orientations, with or without linkers, may provide preferred binding characteristics in comparison to other orientations.

For instance, the order of a first ISVD (e.g. ISVD 1) and a second ISVD (e.g. ISVD 2) in the polypeptide of the invention can be (from N-terminus to C-terminus): (i) ISVD 1 (e.g. Nanobody 1)-[linker]-ISVD 2 (e.g. Nanobody 2); or (ii) ISVD 2 (e.g. Nanobody 2)-[linker]-ISVD 1 (e.g. Nanobody 1); (wherein the linker is optional). All orientations are encompassed by the invention. Polypeptides that contain an orientation of ISVDs that provides desired binding characteristics can be easily identified by routine screening, for instance as exemplified in the examples section.

In the polypeptides of the invention, the two or more ISVDs, such as Nanobodies, may be directly linked to each other (as for example described in WO 99/23221) and/or may be linked to each other via one or more suitable linkers, or any combination thereof. Suitable linkers for use in the polypeptides of the invention will be clear to the skilled person, and may generally be any linker used in the art to link amino acid sequences. Preferably, said linker is suitable for use in constructing proteins or polypeptides that are intended for pharmaceutical use.

Some particularly preferred linkers include the linkers that are used in the art to link antibody fragments or antibody domains. These include the linkers mentioned in the publications cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISVD, such as a Nanobody by itself forms a complete antigen-binding site).

For example, a linker may be a suitable amino acid or amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table 3.

Some other particularly preferred linkers are poly-alanine (such as AAA), as well as the linkers GS30 (SEQ ID NO: 85 in WO 06/122825) and GS9 (SEQ ID NO: 84 in WO 06/122825).

It is encompassed within the scope of the invention that the length, the degree of flexibility and/or other properties of the linker(s) used (although not critical, as it usually is for linkers used in ScFv fragments) may have some influence on the properties of the final polypeptide and/or dimer of the invention, including but not limited to the affinity, specificity or avidity for a chemokine, or for one or more of the other antigens. Based on the disclosure herein, the skilled person will be able to determine the optimal linker(s) for use in a specific polypeptide and/or dimer of the invention, optionally after some limited routine experiments.

When two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

In the polypeptides of the invention, the ISVDs can be preceded by an N-terminal extension. In the context of the present invention, the N-terminal extension consists of an amino acid sequence of at least one amino acid residue to maximal 40 amino acid residues, preferably between 2 and 30 amino acid residues, such as between 2 and 20 amino acid residues, such as for instance, 2, 3, 4, 5, 6, 7, 8, 9 or 10 amino acid residues. The N-terminal extension is present N-terminally of the first (i.e. most N-terminally located, generally designated by amino acid 1 according to the Kabat numbering) amino acid residue of the first (i.e. most N-terminally located) ISVD in the polypeptide of the invention.

Accordingly, the present invention relates to a first polypeptide and/or said second polypeptide comprising an N-terminal extension.

In an embodiment, the present invention relates to the dimer as described herein, wherein said at least two ISVDs of said first polypeptide are identical and/or said at least two ISVDs of said second polypeptide are identical.

In an embodiment the first polypeptide of the invention and the second polypeptide of the invention of the dimer are different.

In an embodiment the first polypeptide of the invention and the second polypeptide of the invention making the dimer are the same. Accordingly, the first polypeptide of the present invention and the second polypeptide of the present invention are identical.

TABLE 3

Some Linker sequences of the invention

| Name of linker | SEQ ID NO: | Amino acid sequences |
|---|---|---|
| A3 | 16 | AAA |
| GS5 (5GS) | 17 | GGGGS |
| GS7 (7GS) | 18 | SGGSGGS |
| GS9 (9GS) | 19 | GGGGSGGGS |
| GS10 (10GS) | 20 | GGGGSGGGGS |
| GS15 (15GS) | 21 | GGGGSGGGGSGGGGS |
| GS18 (18GS) | 22 | GGGGSGGGGSGGGGGGS |
| GS20 (20GS) | 23 | GGGGSGGGGSGGGGSGGGGS |
| GS25 (25GS) | 24 | GGGGSGGGGSGGGGSGGGGSGGGGS |
| GS30 (30GS) | 25 | GGGGSGGGGSGGGGSGGGGSGGGGSGGGGS |
| GS35 (35GS) | 26 | GGGGSGGGGSGGGGSGGGGSGGGGSGGGGSGGGGS |

As further elaborated infra, the ISVDs can be derived from a $V_{HH}$, $V_H$ or a $V_L$ domain, however, the ISVDs are chosen such that they do not form complementary pairs of $V_H$ and $V_L$ domains in the polypeptides of the invention or in the dimers of the invention. The Nanobody, $V_{HH}$, and humanized $V_{HH}$ are unusual in that they are derived from natural camelid antibodies which have no light chains, and indeed these domains are unable to associate with camelid light chains to form complementary $V_{HH}$ and $V_L$ pairs. Thus, the dimers and polypeptides of the present invention do not comprise complementary ISVDs and/or form complementary ISVD pairs, such as, for instance, complementary $V_H/V_L$ pairs.

In an embodiment, the present invention relates to a dimer as described herein, wherein said linker is chosen from the group consisting of SEQ ID NOs: 16-26.

Monovalent polypeptides comprise or essentially consist of only one binding unit (such as e.g., immunoglobulin single variable domains). Polypeptides that comprise two or more binding units (such as e.g., immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprise three immunoglobulin single variable domains, optionally linked via two linker sequences; whereas a "tetravalent" polypeptide may comprise four immunoglobulin single variable domains, optionally linked via three linker sequences, etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., immunoglobulin single variable domains) in which at least one binding unit is directed against a first antigen of a first target and at least one binding unit is directed against an antigen of a second target (e.g. different from the first target) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen of a first target and at least one further immunoglobulin single variable domain directed against a second antigen (i.e., different from the first antigen of said first target), etc.

"Multiparatopic polypeptides", such as e.g., "biparatopic polypeptides" or "triparatopic polypeptides", comprise or essentially consist of two or more binding units that each have a different paratope. In a further aspect, the polypeptide of the invention is a multiparatopic polypeptide (also referred to herein as "multiparatopic polypeptide(s) of the invention"), such as e.g., "(a) biparatopic polypeptide(s) of the invention" or "triparatopic polypeptide(s) of the invention". The term "multiparatopic" (antigen-) binding molecule or "multiparatopic" polypeptide as used herein shall mean a polypeptide comprising at least two (i.e. two or more) immunoglobulin single variable domains, wherein a "first" immunoglobulin single variable domain is directed against a first target and a "second" immunoglobulin single variable domain is directed against the same, first target, wherein said "first" and "second" immunoglobulin single variable domains have a different paratope. Accordingly, a multiparatopic polypeptide comprises or consists of two or more immunoglobulin single variable domains that are directed against a first target, wherein at least one "first" immunoglobulin single variable domain is directed against a first epitope on said first target and at least one "second" immunoglobulin single variable domain is directed against a second epitope on said first target different from the first epitope on said first target.

In an embodiment, the present invention relates to a dimer as described herein, wherein said first polypeptide and/or said second polypeptide is chosen from the group of monovalent, bivalent, multivalent, monospecific, bispecific and multispecific polypeptides.

As used herein, the "target" of the invention is any suitable antigen (e.g. any target of interest) to which an ISVD can bind. The ISVD of the invention may for example bind or be directed against an antigenic determinant, epitope, part, domain, subunit or confirmation (where applicable) of a target, such as, for instance, a Receptor Tyrosine Kinase (RTK) or a G-protein coupled receptor (GPCR), e.g. participating in malignancy. A target of the invention can be any target, preferably on the surface of a cell, such as a cellular receptor, e.g. known to participate in malignancy. For instance, receptor tyrosine kinases (RTK) and RTK-mediated signal transduction pathways are involved in tumour initiation, maintenance, angiogenesis, and vascular proliferation. About 20 different RTK classes have been identified, of which the most extensively studied are: 1. RTK class I (EGF receptor family) (ErbB family), 2. RTK class II (Insulin receptor family), 3. RTK class III (PDGF receptor family), 4. RTK class IV (FGF receptor family), 5. RTK class V (VEGF receptors family), 6. RTK class VI (HGF receptor family), 7. RTK class VII (Trk receptor family), 8. RTK class VIII (Eph receptor family), 9. RTK class IX (AXL receptor family), 10. RTK class X (LTK receptor family), 11. RTK class XI (TIE receptor family), 12. RTK class XII (ROR receptor family), 13. RTK class XIII (DDR receptor family), 14. RTK class XIV (RET receptor family), 15. RTK class XV (KLG receptor family), 16. RTK class XVI (RYK receptor family), 17. RTK class XVII (MuSK receptor family). In particular, targets such as epidermal growth factor receptors (EGFR), platelet-derived growth factor receptors (PDGFR), vascular endothelial growth factor receptors (VEGFR), c-Met, HER3, plexins, integrins, CD44, RON and on receptors involved in pathways such as the Ras/Raf/mitogen-activated protein (MAP)-kinase and phosphatidylinositol-3 kinase (PI3K)/Akt/mammalian target of rapamycin (mTOR) pathways.

Accordingly the present invention relates to a dimer as described herein, wherein said first target and said second target are independently chosen from the group consisting of GPCRs, Receptor Tyrosine Kinases, DDR1, Discoidin I (CD167a antigen), DDR2, ErbB-1, C-erbB-2, FGFR-1, FGFR-3, CD135 antigen, CD 117 antigen, Protein tyrosine kinase-1, c-Met, CD148 antigen, C-ret, ROR1, ROR2, Tie-1, Tie-2, CD202b antigen, Trk-A, Trk-B, Trk-C, VEGFR-1, VEGFR-2, VEGFR-3, Notch receptor 1-4, FAS receptor, DR5, DR4, CD47, CX3CR1, CXCR-3, CXCR-4, CXCR-7, Chemokine binding protein 2, and CCR1, CCR2, CCR3, CCR4, CCR5, CCR6, CCR7, CCR8, CCR9, CCR10 and CCR11; MART-1, carcino-embryonic antigen ("CEA"), gp100, MAGE-1, HER-2, and Lewis$^Y$ antigens, CD123, CD44, CLL-1, CD96, CD47, CD32, CXCR4, Tim-3, CD25, TAG-72, Ep-CAM, PSMA, PSA, GD2, GD3, CD4, CD5, CD19, CD20, CD22, CD33, CD36, CD45, CD52, and CD147; growth factor receptors, including ErbB3 and ErbB4; and Cytokine receptors including Interleukin-2 receptor gamma chain (CD132 antigen); Interleukin-10 receptor alpha chain (IL-10R-A); Interleukin-10 receptor beta chain (IL-10R-B); Interleukin-12 receptor beta-1 chain (IL-12R-beta1); Interleukin-12 receptor beta-2 chain (IL-12 receptor beta-2); Interleukin-13 receptor alpha-1 chain (IL-13R-alpha-1) (CD213 al antigen); Interleukin-13 receptor alpha-2 chain (Interleukin-13 binding protein); Interleukin-17 receptor (IL-17 receptor); Interleukin-17B receptor (IL-17B receptor); Interleukin 21 receptor precursor (IL-21R); Interleukin-1 receptor, type I (IL-1R-1) (CD121a); Interleukin-1 receptor, type II (IL-1R-beta) (CDw121b); Interleukin-1 receptor antagonist protein (IL-1ra); Interleukin-2 receptor alpha chain (CD25 antigen); Interleukin-2 receptor beta chain (CD122 antigen); Interleukin-3 receptor alpha chain (IL-3R-alpha) (CD123 antigen).

Exemplary molecular targets (e.g., antigens) include CD proteins such as CD2, CD3, CD4, CD8, CD11, CD19, CD20, CD22, CD25, CD33, CD34, CD40, CD52; members of the ErbB receptor family such as the EGF receptor (EGFR, HER1, ErbB1), HER2 (ErbB2), HER3 (ErbB3) or HER4 (ErbB4) receptor; macrophage receptors such as CRIg; tumor necrosis factors such as TNFa or TRAIL/Apo-2; cell adhesion molecules such as LFA-1, Mad, p150, p95, VLA-4, ICAM-1, VCAM and αvβ3 integrin including either a or subunits thereof; growth factors and receptors such as EGF, FGFR (e.g., FGFR3) and VEGF; IgE; cytokines such as IL1; cytokine receptors such as IL2 receptor; blood group antigens; flk2/flt3 receptor; obesity (OB) receptor; mpl receptor; CTLA-4; protein C; neutropilins; ephrins and receptors; netrins and receptors; slit and receptors; chemokines and chemokine receptors such as CCL5, CCR4, CCR5; amyloid beta; complement factors, such as complement factor D; lipoproteins, such as oxidized LDL (oxLDL); lymphotoxins, such as lymphotoxin alpha (LTa). Other molecular targets include Tweak, B7RP-1, proprotein convertase subtilisin/kexin type 9 (PCSK9), sclerostin, c-kit, Tie-2, c-fms, and anti-M1.

It is also expected that the immunoglobulin single variable domains, polypeptides and/or dimers of the invention will generally bind to all naturally occurring or synthetic analogs, variants, mutants, alleles, parts and fragments of its targets.

Accordingly, the invention relates to dimer as described herein, wherein said ISVD of said first polypeptide binds a first target and/or said ISVD of said second polypeptide binds a second target.

Accordingly, the invention relates to dimer as described herein, wherein said first polypeptide binds a first target:
with an $IC_{50}$ of at most 100 nM, such as 50 nM, 20 nM, 10 nM, 9 nM, 8 nM, 7 nM, 6 nM, 5 nM, 4 nM, 3 nM, preferably even at most 2 nM, such as 1 nM, as determined by a competition FACS;
with a dissociation constant ($K_D$) of $10^{-5}$ to $10^{-12}$ moles/litre or less, and preferably $10^{-7}$ to $10^{-12}$ moles/litre or less and more preferably $10^{-8}$ to $10^{-12}$ moles/litre;
with a rate of association ($k_{on}$-rate) of between $10^2$ M$^{-1}$s$^{-1}$ to about $10^7$ M$^{-1}$s$^{-1}$, preferably between $10^3$ M$^{-1}$s$^{-1}$ and $10^7$ M$^{-1}$s$^{-1}$, more preferably between $10^4$ M$^{-1}$s$^{-1}$ and $10^5$ M$^{-1}$s$^{-1}$, such as between $10^5$ M$^{-1}$s$^{-1}$ and $10^7$ M$^{-1}$s$^{-1}$; and/or
with a rate of dissociation ($k_{off}$ rate) between 1 s$^{-1}$ and $10^{-6}$ s$^{-1}$, preferably between $10^{-2}$ s$^{-1}$ and $10^{-6}$ s$^{-1}$, more preferably between $10^{-3}$ s$^{-1}$ and $10^{-6}$ s$^{-1}$, such as between $10^{-4}$ s$^{-1}$ and $10^{-6}$ s$^{-1}$.

Accordingly, the invention relates to dimer as described herein, wherein said second polypeptide binds a second target:
with an $IC_{50}$ of at most 100 nM, such as 50 nM, 20 nM, 10 nM, 9 nM, 8 nM, 7 nM, 6 nM, 5 nM, 4 nM, 3 nM, preferably even at most 2 nM, such as 1 nM, as determined by a competition FACS;
with a dissociation constant ($K_D$) of $10^{-5}$ to $10^{-12}$ moles/litre or less, and preferably $10^{-7}$ to $10^{-12}$ moles/litre or less and more preferably $10^{-8}$ to $10^{-12}$ moles/litre;
with a rate of association ($k_{on}$-rate) of between $10^2$ M$^{-1}$s$^{-1}$ to about $10^7$ M$^{-1}$s$^{-1}$, preferably between $10^3$ M$^{-1}$s$^{-1}$ and $10^7$ M$^{-1}$s$^{-1}$, more preferably between $10^4$ M$^{-1}$s$^{-1}$ and $1^7$ M$^{-1}$s$^{-1}$, such as between $10^5$ M$^{-1}$s$^{-1}$ and $10^7$ M$^{-1}$s$^{-1}$; and/or with a rate of dissociation ($k_{off}$ rate) between 1 s$^{-1}$ and 10$^{-6}$ s$^{-1}$, preferably between 10$^{-2}$ s$^{-1}$ and 10$^{-6}$ s$^{-1}$, more preferably between 10$^{-3}$ s$^{-1}$ and 10$^{-6}$ s$^{-1}$, such as between 10$^{-4}$s$^{-1}$ and 10$^{-6}$s$^{-1}$.

In an embodiment, the invention relates to dimer as described herein, wherein said first target and said second target are different.

In an embodiment, the invention relates to dimer as described herein, wherein said first target and said second target are identical.

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

An immunoglobulin single variable domains may be used as a "binding unit", "binding domain" or "building block" (these terms are used interchangeable) for the preparation of a polypeptide, which may optionally contain one or more further immunoglobulin single variable domains that can serve as a binding unit (i.e., against the same or a different epitope of the same target and/or against one or more different targets).

The term "immunoglobulin single variable domain" ("ISVD"), interchangeably used with "single variable domain" ("SVD"), defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single $V_H$ or $V_L$ domain. Hence, the antigen binding site of an immunoglobulin single variable domain is formed by no more than three CDRs.

The terms "immunoglobulin single variable domain" and "single variable domain" hence do not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

Generally, single variable domains will be amino acid sequences that essentially consist of 4 framework regions (FR1 to FR4, respectively) and 3 complementarity determining regions (CDR1 to CDR3, respectively). Such single variable domains and fragments are most preferably such that they comprise an immunoglobulin fold or are capable of forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding unit does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In an embodiment of the invention, the immunoglobulin single variable domains are light chain variable domain sequences (e.g. a $V_L$-sequence), or heavy chain variable domain sequences (e.g. a $V_H$-sequence); more specifically, the immunoglobulin single variable domains can be heavy chain variable domain sequences that are derived from a conventional four-chain antibody or heavy chain variable domain sequences that are derived from a heavy chain antibody.

For example, the single variable domain or immunoglobulin single variable domain (or an amino acid that is suitable for use as an immunoglobulin single variable domain) may be a (single) domain antibody (or an amino acid that is suitable for use as a (single) domain antibody), a "dAb" or dAb (or an amino acid that is suitable for use as a dAb) or a Nanobody (as defined herein, and including but not limited to a $V_{HH}$); other single variable domains, or any suitable fragment of any one thereof.

For a general description of (single) domain antibodies, reference is also made to the prior art cited herein, as well as to EP 0368684. For the term "dAb's", reference is for example made to Ward et al. 1989 (Nature 341: 544-546), to Holt et al. 2003 (Trends Biotechnol. 21: 484-490); as well as to for example WO 04/068820, WO 06/030220, WO 06/003388, WO 06/059108, WO 07/049017, WO 07/085815 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the immunoglobulin single variable domain may be a NANOBODY® (as defined herein) or a suitable fragment thereof. [Note: NANOBODY®, NANOBODIES® and NANOCLONE® are registered trademarks of Ablynx N.V.] For a general description of Nanobodies, reference is made to the further description below, as well as to the prior art cited herein, such as e.g. described in WO 08/020079 (page 16).

For a further description of $V_{HH}$'s and Nanobodies, reference is made to the review article by Muyldermans 2001 (Reviews in Molecular Biotechnology 74: 277-302), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g. described in Davies and Riechmann 1994 (FEBS 339: 285-290), 1995 (Biotechnol. 13: 475-479), 1996 (Prot. Eng. 9: 531-537) and Riechmann and Muyldermans 1999 (J. Immunol. Methods 231: 25-38).

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences and humanized camelid immunoglobulin sequences, or camelized immunoglobulin single variable domains, e.g. camelized dAbs as described by Ward et al. 1989 (see for example WO 94/04678 and Davies and Riechmann 1994, 1995 and 1996) and camelized VH.

Again, such immunoglobulin single variable domains may be derived in any suitable manner and from any suitable source, and may for example be naturally occurring $V_{HH}$ sequences (i.e. from a suitable species of Camelid) or synthetic or semi-synthetic amino acid sequences, including but not limited to partially or fully "humanized" $V_{HH}$, "camelized" immunoglobulin sequences (and in particular camelized $V_H$), as well as Nanobodies and/or $V_{HH}$ that have been obtained by techniques such as affinity maturation (for example, starting from synthetic, random or naturally occurring immunoglobulin sequences, such as $V_{HH}$ sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

The amino acid sequence and structure of an immunoglobulin single variable domain can be considered—without however being limited thereto—to be comprised of four framework regions or "FRs", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDRs", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in an immunoglobulin single variable domain can be in the region of 110-120, is preferably 112-115, and is most preferably 113.

As further described in paragraph q) on pages 58 and 59 of WO 08/020079 (incorporated herein by reference), the amino acid residues of an immunoglobulin single variable domain are numbered according to the general numbering for VH domains given by Kabat et al. ("Kabat numbering") ("Sequence of proteins of immunological interest", US Public Health Services, NIH Bethesda, Md., Publication No. 91), as applied to VHH domains from Camelids in the article of Riechmann and Muyldermans 2000 (J. Immunol. Methods 240: 185-195; see for example FIG. 2 of this publication), and accordingly FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

It will be clear, based on the examples of immunoglobulin single variable domain sequences that are given herein as well as in WO 08/020079, in WO 06/040153 and in the further immunoglobulin single variable domain-related references cited therein, that the precise number of amino acid residues will also depend on the length of the specific CDR's that are present in the immunoglobulin single variable domain. With regard to the CDR's, as is well-known in the art, there are multiple conventions to define and describe the CDR's of a VH or VHH fragment, such as the Kabat definition (which is based on sequence variability and is the most commonly used) and the Chothia definition (which is based on the location of the structural loop regions). Reference is for example made to the website http://www.bioinf.org.uk/abs/. For the purposes of the present specification and claims, even though the CDR's according to Kabat may also be mentioned, the CDRs are most preferably defined on the basis of the Abm definition (which is based on Oxford Molecular's AbM antibody modelling software), as this is considered to be an optimal compromise between the Kabat and Chothia definitions. Reference is again made to the website http://www.bioinf.org.uk/abs/).

In an embodiment, FR4 comprises the C-terminal amino acid sequence VTVSS, i.e. each of positions 109, 110, 111, 112 and 113. The present invention also encompasses ISVDs ending at position 109, 110, 111 or 112. In an aspect of the invention, FR4 ends with the C-terminal amino acid sequence VTVS (positions 109-112), FR4 ends with the C-terminal amino acid sequence VTV (positions 109-111), FR4 ends with the C-terminal amino acid sequence VT (positions 109-110), or FR4 ends with the C-terminal amino acid V (position 109). The C-terminal extension can be present C-terminally of the last amino acid residue of FR4, e.g. V109, T110, V111, S112 or S113, of the last (most C-terminally located) ISVD, in which the cysteine moiety of the invention is preferably present or positioned at the C-terminus of the C-terminal extension. In an embodiment, FR4 comprises the C-terminal amino acid sequence VTVSS and the C-terminal extension is a cysteine (e.g. a polypeptide of the invention ending in VTVSSC). In an embodiment, FR4 comprises the C-terminal amino acid sequence VTVS and the C-terminal extension is a cysteine (e.g. a polypeptide of the invention ending in VTVSC). In an embodiment, FR4 comprises the C-terminal amino acid sequence VTV and the C-terminal extension is a cysteine (e.g. a polypeptide of the invention ending in VTVC). In an embodiment, FR4 comprises the C-terminal amino acid sequence VT and the C-terminal extension is a cysteine (e.g. a polypeptide of the invention ending in VTC). In an embodiment, FR4 comprises the C-terminal amino acid V and the C-terminal extension is a cysteine (e.g. a polypeptide of the invention ending in VC).

In an embodiment, the present invention relates to a dimer as described herein, wherein an ISVD is a light chain variable domain sequence (VL), is a heavy chain variable domain sequence (VH), is derived from a conventional four-chain antibody or is derived from a heavy chain antibody.

In an embodiment, the present invention relates to a dimer as described herein, wherein said ISVD is chosen from the group consisting of single domain antibodies, domain antibodies, amino acid sequences suitable for use as single domain antibody, amino acid sequences suitable for use as domain antibody, dAbs, amino acid sequences suitable for use as dAb, Nanobodies, VHHs, humanized VHHs, and camelized VHs. Preferably, the ISVD comprises between 100 to 140 amino acids, such as between 110-130 amino acids.

In an embodiment, the present invention relates to a dimer as described herein, wherein said ISVD chosen from the group consisting of Nanobodies, VHHs, humanized VHHs, and camelized VHs comprises between 105 to 125 amino acids, such as preferably between 110-120 amino acids, such as 110, 111, such as 110, 111, 112, 113, 114, 115, 116, 117, 118, 119 or 120 amino acids, most preferably 113 amino acids.

The present invention relates to a dimer as described herein, wherein said ISVD chosen from the group consisting of Nanobodies, VHHs, humanized VHHs, and camelized VHs ends at amino acid position 105, 106, 107, 108, 109, 110, 111, 112, 113, 114, 115, 116, 117, 118 119 or 120, preferably at amino acid position 113 according to Kabat numbering.

The present invention relates to a dimer as described herein, wherein said ISVD is chosen from the group consisting of single domain antibodies, domain antibodies, amino acid sequences suitable for use as single domain antibody, amino acid sequences suitable for use as domain antibody, dAbs, amino acid sequences suitable for use as dAb and camelized VHs, wherein said single domain antibodies, domain antibodies, amino acid sequences suitable for use as single domain antibody, amino acid sequences suitable for use as domain antibody, dAbs, amino acid sequences suitable for use as dAb and camelized VHs are derived from a VH.

The present invention relates to a dimer as described herein, wherein said single domain antibodies, domain antibodies, amino acid sequences suitable for use as single domain antibody, amino acid sequences suitable for use as domain antibody, dAbs, amino acid sequences suitable for use as dAb and camelized VHs comprise 110-130 amino acids, preferably 115-127 amino acids, such as 115, 116, 117, 118, 119, 120, 121, 122, 123, 124, 125, 126 or 127 amino acids, most preferably 123 amino acids. Preferably, wherein said single domain antibodies, domain antibodies, amino acid sequences suitable for use as single domain antibody, amino acid sequences suitable for use as domain antibody, dAbs, amino acid sequences suitable for use as dAb and camelized VHs end at amino acid 110, 111, 112, 113, 114, 115, 116, 117, 118, 119, 120, 121, 122, 123, 124, 125, 126, 127, 128, 129 or 130 preferably at amino acid 123, according to Kabat numbering.

Accordingly the present invention relates to a dimer as described herein, wherein said ISVD is chosen from the group consisting of single domain antibodies, domain antibodies, amino acid sequences suitable for use as single domain antibody, amino acid sequences suitable for use as domain antibody, dAbs and amino acid sequences suitable for use as dAb, wherein said single domain antibodies, domain antibodies, amino acid sequences suitable for use as single domain antibody, amino acid sequences suitable for use as domain antibody, dAbs or amino acid sequences suitable for use as dAb are derived from a VL. Preferably, wherein said single domain antibodies, domain antibodies, amino acid sequences suitable for use as single domain antibody, amino acid sequences suitable for use as domain antibody, dAbs and amino acid sequences suitable for use as dAb comprise 100-120 amino acids, preferably 105-115 amino acids, such as 100, 101, 102, 103, 104, 105, 106, 107, 108, 109, 110, 111, 112, 113, 114, 115, 116, 117, 118, 119 or 120 amino acids, most preferably 108 amino acids. Preferably, wherein said single domain antibodies, domain antibodies, amino acid sequences suitable for use as single domain antibody, amino acid sequences suitable for use as domain antibody, dAbs and amino acid sequences suitable for use as dAb, end at amino acid 101, 102, 103, 104, 105, 106, 107, 108, 109, 110, 111, 112, 113, 114, 115, 116, 117, 118, 119 or 120, preferably at amino acid 108, according to Kabat numbering.

In a specific aspect of the invention, a polypeptide or dimer of the invention may have an increased half-life, compared to the corresponding polypeptide or dimer of the invention. Some preferred, but non-limiting examples of such polypeptides or dimers will become clear to the skilled person based on the further disclosure herein, and for example comprise polypeptides of the invention that have been chemically modified to increase the half-life thereof (for example, by means of pegylation);

polypeptides of the invention that comprise at least one additional binding site for binding to a serum protein (such as serum albumin); or polypeptides of the invention that comprise at least one polypeptide of the invention that is linked to at least one moiety that increases the half-life of the polypeptide of the invention.

According to a specific, preferred but non-limiting aspect of the invention, the polypeptides of the invention may contain, besides the one or more immunoglobulin single variable domains directed against an epitope on a target cell, at least one immunoglobulin single variable domain against human serum albumin. These immunoglobulin single variable domains against human serum albumin may be as generally described in the applications by Ablynx N.V. cited herein (see for example WO 04/062551). Some particularly preferred ISVDs, such as Nanobodies that provide for increased half-life and that can be used in the polypeptides of the invention include the ISVDs, e.g. Nanobodies ALB-1 to ALB-10 disclosed in WO 06/122787 (see Tables II and III) of which ALB-8 (SEQ ID NO: 62 in WO 06/122787) is particularly preferred, as well as the ISVDs, e.g. Nanobodies disclosed in WO 2012/175400 (SEQ ID NOs: 1-11 of WO 2012/175400) and the ISVD, e.g. Nanobody with SEQ ID NO: 109 disclosed in the U.S. provisional application No. 62/047,560 entitled "Improved immunoglobulin single variable domains" (date of filing: Sep. 8, 2014; assignee: Ablynx N.V.).

In a further aspect, the invention relates to a dimer as described herein, wherein said first polypeptide and/or said second polypeptide further comprises one or more other groups, residues, moieties or binding units (as further defined herein), wherein said one or more other groups, residues, moieties or binding units increase the half-life of the dimer (compared to the dimer lacking said one or more other groups, residues, moieties or binding units). Preferably, the said one or more other groups, residues, moieties or binding units that increase the half-life of the dimer is an ISVD that increases the half-life of the dimer.

In an embodiment the invention relates to a dimer as described herein, wherein said ISVD that increases the half-life of the dimer binds serum albumin, preferably human serum albumin, or serum immunoglobulin, preferably, human IgG.

In an embodiment the invention relates to a dimer as described herein, which has a serum half-life that is at least 1.5 times, preferably at least 2 times, such as at least 5 times, for example at least 10 times or more than 20 times, larger than the half-life of the corresponding dimer without said ISVD that increases the half-life of the dimer.

In an embodiment the invention relates to a dimer as described herein, which has a serum half-life that is increased with more than 1 hours, preferably more than 2 hours, more preferably more than 6 hours, such as more than 12 hours, or even more than 24, 48 or 72 hours, compared to the corresponding said ISVD that increases the half-life of the dimer.

In an embodiment the invention relates to a dimer as described herein, which has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred but non-limiting aspect of the invention, the invention provides a polypeptide of the invention comprising at least one immunoglobulin single variable domain (ISVD);

and further comprising one or more (preferably one) serum albumin binding immunoglobulin single variable domain as described herein, e.g. the serum albumin binding immunoglobulin single variable domain of Alb11, Alb23, Alb129, Alb132, Alb8, Alb11 (S112K)-A, Alb82, Alb82-A, Alb82-AA, Alb82-AAA, Alb82-G, Alb82-GG, Alb82-GGG (see Table 10), e.g. chosen from SEQ ID NO:s 32-44.

TABLE 10

Serum albumin binding ISVD sequences ("ID" refers to the SEQ ID NO as used herein)

| Name | ID | Amino acid sequence |
|---|---|---|
| Alb8 | 32 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVTVSS |
| Alb23 | 33 | EVQLLESGGGLVQPGGSLRLSCAASGFTFRSFGMSWVRQAPGKGPEWVSSISGSGSDTLYADS VKGRFTISRDNSKNTLYLQMNSLRPEDTAVYYCTIGGSLSRSSQGTLVTVSS |
| Alb129 | 34 | EVQLVESGGGVVQPGNSLRLSCAASGFTFSSFGMSWVRQAPGKGLEWVSSISGSGSDTLYADS VKGRFTISRDNAKTTLYLQMNSLRPEDTATYYCTIGGSLSRSSQGTLVTVSSA |
| Alb132 | 35 | EVQLVESGGGVVQPGGSLRLSCAASGFTFRSFGMSWVRQAPGKGPEWVSSISGSGSDTLYAD SVKGRFTISRDNSKNTLYLQMNSLRPEDTATYYCTIGGSLSRSSQGTLVTVSSA |
| Alb11 | 36 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVTVSS |
| Alb11 (S112K)-A | 37 | EVQLVESGGGLVQPGNSLRLSCAASGFTFSSFGMSWVRQAPGKGLEWVSSISGSGSDTLYADS VKGRFTISRDNAKTTLYLQMNSLRPEDTAVYYCTIGGSLSRSSQGTLVKVSSA |
| Alb82 | 38 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSS |
| Alb82-A | 39 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSA |
| Alb82-AA | 40 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSAA |
| Alb82-AAA | 41 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSAAA |
| Alb82-G | 42 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSG |
| Alb82-GG | 43 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSGG |

TABLE 10-continued

Serum albumin binding ISVD sequences ("ID" refers to the SEQ ID NO as used herein)

| Name | ID | Amino acid sequence |
|---|---|---|
| Alb82-GGG | 44 | EVQLVESGGGVVQPGNSLRLSCAASGFTFSSFGMSWVRQAPGKGLEWVSSISGSGSDTLYADS VKGRFTISRDNAKTTLYLQMNSLRPEDTALYYCTIGGSLSRSSQGTLVTVSSGGG |

ISVDs, such as Nanobodies, comprise internal (also known as canonical or intramolecular) disulfide bridges, which are highly conserved. Removing these specific internal disulfide bridges compromises the activity of the ISVDs.

The present inventors surprisingly observed that oxidizing the thiol moiety (—SH) of an unpaired cysteine residue (abbreviated as Cys, cys or C; 2-Amino-3-sulfhydrylpropanoic acid; which is an α-amino acid with the chemical formula $HO_2CCH(NH_2)CH_2SH$) located in the C-terminal extension, preferably at the C-terminus, of a first polypeptide of the invention and the thiol moiety of an unpaired cysteine moiety located in the C-terminal extension, preferably at the C-terminus, of a second polypeptide of the invention resulted in a disulfide derivative cystine thereby making dimers, but in which intramolecular thiol moieties were not reacted. In other words, the thiol-groups of the C-terminally located cysteines were specifically oxidized to form intermolecular bonds, without aberrant or re-oxidizing the intramolecular thiol-groups, thereby maintaining the integrity of the ISVD, as demonstrated in the examples section. The coupling of the polypeptides into a dimer was performed by chemical conjugation, in which the thiol moieties of the cysteine in the C-terminal extension in each of two polypeptides were oxidized to the disulfide derivative cystine. Preferably, said cystine (e.g. disulfide bridge) is the only inter-chain disulfide bond present in the dimer, e.g.

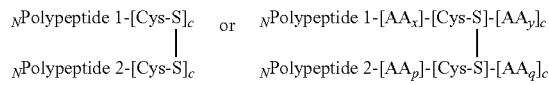

in which

denotes disulfide derivative cystine;

-[Cys-S] and -[AA$_x$]-[Cys-S]-[AA$_y$] denote the C-terminal extension comprising a cysteine of said polypeptide;

"AA" represents any amino acid as defined herein;

the prefix "N" represents the N-terminus of a polypeptide;

the suffix "C" represents the C-terminus of a polypeptide;

the subscripts "x", "y", "p" and "q" represent a number, independently chosen from the integers ranging from 0-50, such as ranging from 1-40, or ranging from 2-30, such as, for instance, 0, 1, 2, 3, 4, 5, 6, 7, 8, 9, 10, 11, 12, 13, 14, 15, 16, 17, 18, 19 or 20. For instance, if all of "x", "y", "p" and "q" are 0, the C-terminal extension is only the cysteine; and if both of "y" and "q" are 0, but "x" and "p" are not 0, the C-terminus of the C-terminal extension is cysteine.

The present invention relates to a method for making (polypeptide-)dimers, comprising at least the steps of: (i) providing a first polypeptide, wherein said first polypeptide comprises at least one immunoglobulin single variable domain (ISVD) and a C-terminal extension comprising a cysteine moiety, preferably at the C-terminus; (ii) providing a second polypeptide, wherein said second polypeptide comprises at least one immunoglobulin single variable domain (ISVD) and a C-terminal extension comprising a cysteine moiety, preferably at the C-terminus; and (iii) oxidizing the thiol moiety of said cysteine moiety at the C-terminal extension, preferably at the C-terminus, of said first polypeptide and the thiol moiety of said cysteine moiety at the C-terminal extension, preferably at the C-terminus, of said second polypeptide to a disulfide derivative cystine; thereby making said dimers; and said disulfide derivative cystine is the only intermolecular disulfide bond present in the dimer.

The invention further relates to a method as described herein, wherein said first polypeptide comprises at least two ISVDs and/or said second polypeptide comprises at least two ISVDs.

The invention further relates to a method as described herein, wherein said at least two ISVDs of said first polypeptide are identical and/or said at least two ISVDs of said second polypeptide are identical.

The invention further relates to a method as described herein, wherein said first polypeptide and said second polypeptide are identical or are different.

As used herein, the term "bispecific dimer" relates to a dimer in which the first polypeptide of the dimer is different from the second polypeptide of the dimer, independent of the valence (e.g. monovalent, bivalent or multivalent) or specificity (e.g. monospecific, bispecific or multispecific) of the first and second polypeptide. It will be appreciated that a dimer can comprise two identical, but bispecific polypeptides.

Methods are provided for the generation of bispecific dimers, e.g. the first polypeptide is different from the second polypeptide of the dimer. In a first embodiment, the host strain e.g. the *Pichia* strain is transformed with two different vectors, in which the first vector encodes the first polypeptide and the second vector encodes the second polypeptide. Alternatively, one vector is used, but the vector comprises a first gene encoding the first polypeptide and a second gene encoding the second polypeptide. Alternatively, two host cells are used each expressing the one or other polypeptide, such as, for instance, a first vector encoding the first polypeptide is expressed in a first host cell, e.g. a *Pichia*, and a second vector encoding the second polypeptide is expressed in a second host cell, e.g. also a *Pichia*. Coupling of the polypeptides into a bispecific dimer is performed by chemical conjugation, e.g. in the *Pichia* spent media, in which the cysteines (preferably C-terminally located) in the C-terminal extension in each of said two polypeptides are oxidized to a disulfide derivative cystine via their thiol moieties at near neutral pH, such as, for instance, between pH 6.5 and pH 7.5, e.g. pH 6.5, pH 6.6, pH 6.7, pH 6.8, pH 6.9, pH 7.0, pH 7.1 pH 7.2, pH 7.3, pH 7.4, and pH 7.5.

Accordingly, the present invention relates to method for making bispecific dimers, comprising at least the steps of:
(i) providing a first polypeptide, wherein said first polypeptide comprises
at least one immunoglobulin single variable domain (ISVD) and
a C-terminal extension comprising a cysteine moiety, preferably at the C-terminus;
(ii) providing a second polypeptide, wherein said second polypeptide comprises
at least one immunoglobulin single variable domain (ISVD) and
a C-terminal extension comprising a cysteine moiety, preferably at the C-terminus;
wherein said first polypeptide is different from said second polypeptide; and
(iii) oxidizing the thiol moiety of said cysteine moiety at the C-terminus of said first polypeptide and the thiol moiety of said cysteine moiety at the C-terminus of said second polypeptide, optionally by adding oxidizing copper ions ($Cu^{2+}$), and preferably at pH 6.5 to pH 7.5 to a disulfide derivative cystine; thereby making said dimers.

Preferably, the integrity of the ISVDs is maintained and said cystine is the only intermolecular disulfide bond present in the dimer.

The term "integrity" as used herein refers to the maintenance of the structure, stability and/or function of the ISVDs, such as, for instance, maintaining the proper intramolecular disulfide bonds connecting the two layers of anti-parallel β-sheet structures of the immunoglobulin domain, and binding its cognate antigen.

The present invention relates to method as provided herein, wherein the gene encoding the first polypeptide and the gene encoding the second polypeptide are present on two different vectors. Preferably, said vectors are present in one host cell, e.g. *Pichia*. Alternatively, said polypeptides are encoded by different genes which are located on one vector.

The vector of the invention can be any suitable vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

The vectors of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism, for example:
a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;
an amphibian cell or cell line, such as *Xenopus* oocytes;
an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
a plant or plant cell, for example in tobacco plants; and/or
a mammalian cell or cell line, for example a cell or cell line derived from a human, a cell or a cell line from mammals including but not limited to CHO-cells (for example CHO-K1 cells), BHK-cells and human cells or cell lines such as HeLa, COS, Caki and HEK293H cells;
as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited herein.

In the present description, a gene is defined as the entire nucleic acid sequence that is necessary for the synthesis of a functional polypeptide. Hence, the gene includes more than the nucleotides encoding the amino acid sequence of the polypeptide (coding region) but also all the DNA sequences required for the synthesis of a particular RNA transcript. Preferably, step (iii) is performed in *Pichia* spent medium.

Methods for manipulating nucleic acids, such as, for instance, adding, inserting, mutating, replacing, or deleting nucleic acids relative to the nucleic acid encoding the ISVD, are well known to the person skilled in the art. Reference is made to the standard handbooks supra.

The present inventors provide a further optimized protocol for making bispecific dimers, in which the efficiency rate was over 50%, such as 60%, 70%, 80% or even more than 90%, such as >95%. This was accomplished by binding a first, reactive polypeptide to a (solid-)carrier and flowing the second, reactive polypeptide over the first polypeptide bound to the carrier. Any non-reacted second polypeptide can be regenerated (reduced) and flown again over the first polypeptide bound to the carrier. This step can be repeated until all first and/or second polypeptides are reacted.

In step 1, the first polypeptide is reduced to obtain monomeric material, preferably 100% monomeric material. Generic conditions for reducing typical polypeptide solutions are set out herein.

In step 2, the first polypeptide in a buffer is bound under reducing conditions to the carrier. A carrier is preferably a chromatography resin. Preferably, the carrier binds only the first polypeptide, but not the second polypeptide. In order to avoid the possible formation of homodimers of the first polypeptide, while being immobilized, the first polypeptide can be immobilized at low density to the carrier. Such a spatial separation of the individual first polypeptides can be achieved by loading the carrier using sub-optimal binding conditions (e.g. a too high flow rate for a typical affinity resin) or via expanding bed chromatography. Methods and conditions for spatially separating the individual polypeptides on the carrier belong to the common general knowledge or can be achieved with routine experimentation by the person skilled in the art. In a preferred embodiment the carrier only binds the first polypeptide but not the second polypeptide. For instance, a carrier such as Protein A can be used if the first polypeptide (and preferably not the second polypeptide) binds to Protein A. Alternatively, in case both the first polypeptide and the second polypeptide bind to the carrier, then the carrier, after immobilizing the first polypeptide, is saturated with a dummy polypeptide, such as a non-cysteine extended Nanobody before applying the second polypeptide.

In step 3, excess of the second polypeptide, also in reduced form (see above), is applied in a buffer and is circulated over the column (optionally under slightly oxidizing conditions). The second polypeptide is passed over the carrier until the immobilized, first polypeptide is fully complexed (conjugated) with the second polypeptide via a disulfide bond. Preferably, this is followed by measuring the concentration drop of the second polypeptide to match a saturated first polypeptide population. If necessary, for this step conditions are optimized to limit the amount of a formation of a monospecific dimer of the second polypeptides, as is well known to the person skilled in the art. The population of the second polypeptide not bound to the carrier can be recovered and used in future coupling reactions, such as for instance reduced again and applied to the column with the first polypeptide until the first polypeptide is saturated.

In step 4 the bispecific dimer is recovered from the carrier by typical elution conditions for the carrier used, as is well known by the person skilled in the art (e.g. acidic conditions for Protein A).

In the present context, the term "immobilization" refers to a molecule whose movement in space has been restricted either completely or to a small limited region by attachment to a solid structure, e.g. the carrier. In general the term immobilization refers to the act of the limiting movement or making incapable of movement, e.g. retard the movement. The dimers of the invention can be immobilized by any suitable method, such as for instance by adsorption, covalent binding, entrapment, encapsulation and (reversible) cross-linking, preferably covalent binding, more preferably by affinity.

Any suitable carrier for immobilization can be used. The person skilled in the art will appreciate that the suitability of a carrier depends on the method of immobilization. For instance, carriers for covalent binding are agarose, cellulose, crosslinked dextran, polystyrene, polyacrylamide gels, and porous silica gels. A preferred carrier is protein A resin.

Suitable buffers may include, but are not limited to, acetate buffers, phosphate buffers, citrate buffers, sulphate buffers, glycine buffers, carboxylate buffers and/or Tris buffers.

Reducing and oxidizing conditions are well known in the art. Reference is made to the examples section, the description and to e.g. standard chemistry handbooks, such as Principles of Modern Chemistry (2011 by Oxtoby, Gillis and Campion, $7^{th}$ edition). Preferred reducing conditions are performed in 1-15 mM, such as 2-12 mM, 4-11 mM, 5-10 mM, preferably 10 mM DTT for minimal 1 h (to maximal 8 h) at room temperature or overnight at 4° C., at a concentration up to 10 mg/ml polypeptide, in order to remain the canonical —S—S— remains oxidized. Preferred oxidizing conditions are performed in 0.1-10 mM, 0.5-5 mM, preferably 1 mM $CuSO_4$ for 1-4 h, preferably 2 h at room temperature, or by using a convenient redox-couple, which can be easily determined by the person skilled in the art.

Accordingly, the present invention relates to method for making bispecific dimers, comprising at least the steps of:
1. providing a first polypeptide, wherein said first polypeptide comprises
    at least one immunoglobulin single variable domain (ISVD) and
    a C-terminal extension comprising a cysteine moiety, preferably at the C-terminus;
2. reducing said first polypeptide;
3. binding the reduced first polypeptide of step 2 under reducing conditions to a carrier;
4. providing a second polypeptide, wherein said second polypeptide comprises
    at least one immunoglobulin single variable domain (ISVD);
    a C-terminal extension comprising a cysteine moiety, preferably at the C-terminus;
    wherein said first polypeptide is different from said second polypeptide;
5. reducing said second polypeptide;
6. applying the reduced second polypeptide of step 5 to the reduced first polypeptide bound to the carrier of step 3, optionally under slightly oxidizing conditions, oxidizing the thiol moiety of said cysteine moiety, preferably at the C-terminus, of said first polypeptide and the thiol moiety of said cysteine moiety, preferably at the C-terminus, of said second polypeptide to a disulfide derivative cystine; thereby making said bispecific dimers; optionally until all of the first polypeptide are fully conjugated to the second polypeptide via a disulfide bond;
7. optionally non-conjugated second polypeptides are recovered, reduced and applied again according to steps 5 and 6;
8. eluting the bispecific dimer from the carrier.

The invention further relates to any method as described herein, wherein said first polypeptide and/or said second polypeptide comprises an N-terminal extension.

The invention further relates to a method as described herein, wherein said first polypeptide and/or said second polypeptide comprises a C-terminal extension of 50, 40, 30, 20, 10, 9, 8, 7, 6, 5, 4, 3, 2, or 1 amino acid residue(s) comprising a cysteine moiety, preferably at the C-terminus.

The invention further relates to a method as described herein, wherein said C-terminal extension is chosen from the group consisting of SEQ ID NOs: 1-15, preferably said C-terminal extension consists of GlyGlyGlyCys (SEQ ID NO: 4), GlyGlyCys (SEQ ID NO: 3), GlyCys (SEQ ID NO: 2) or Cys (SEQ ID NO: 1).

The invention further relates to a method as described herein, wherein said C-terminal extension is genetically fused to the C-terminal end of the most C-terminally located ISVD in said polypeptide.

In an embodiment, the oxidation process is optimized by adding oxidizing copper ions ($Cu^{2+}$), for instance in the form of $CuSO_4$. It was observed that nearly 100% of the C-terminally located thiol moieties were oxidized after copper treatment. Accordingly, the present invention relates to a method as described herein, wherein at least 80%, such as 85%, 90%, 95%, 99% or even more than 99% such as 100% of said first and/or said second polypeptide are dimerized. The degree of oxidation can be determined by any suitable method, but is preferably determined by mass spectrometry.

In a further embodiment, the dimers are purified to homogeneity. Purification can be accomplished by any suitable technique known in the art, such as chromatography, preferably size exclusion chromatography, of which the person skilled in the art is fully acquainted with. Accordingly, the present invention relates to a method as described herein, further comprising the step of purifying said dimers, optionally via size exclusion chromatography. Accordingly, the present invention relates to a method as described herein, wherein said dimers are purified to at least 90% purity or more, e.g. 95% purity or more, such as 97%, 98%, 99% or even 100%. Purity can be determined by any suitable method known in the art, and preferably is determined by mass spectrometry.

In an embodiment, the present invention relates to a dimer, preparable by a method as described above.

The present inventors surprisingly observed that binding and other functional characteristics, such as potency, of the polypeptides in the dimer were not only retained, but were even ameliorated compared to the corresponding benchmark.

Without being bound to any theory, it was hypothesized that the paratope of the ISVDs can be in a more "favourable" position for antigen recognition in this dimer assemblation than in the corresponding benchmark assemblation.

As used herein, a "benchmark" is used as a point of reference for evaluating performance, such as one or more functional characteristics of a molecule, such as, for instance, affinity, efficacy, and potency as described herein. The particular dimer will determine the appropriateness of a certain benchmark, which can readily be assessed by a person skilled in the art. Preferably the benchmark will consist of the same number and/or the same ISVDs as the number and/or identity of ISVDs of the dimer. Preferably, the benchmarks comprise the same polypeptides making up the dimer, but in the benchmark these polypeptides are formed by genetic fusion instead of chemical conjugation as described herein (see e.g. the examples section). A comparison between a dimer and one or both polypeptides individually making up the dimer already provides significant information on the performance of the dimer.

The dimers of the invention comprise a first polypeptide comprising at least one ISVD and a second polypeptide comprising at least one ISVD. The affinity of the dimer can be determined as a whole, e.g. of both polypeptides together, or the affinity of the dimer can be determined by determining the affinity of each polypeptide constituting the dimer individually. In other words, in the latter case the affinity is determined for a polypeptide, independent of avidity effects due to the other polypeptide.

As used herein, the term "potency" is a measure of an agent, such as a dimer, benchmark, polypeptide, ISVD or Nanobody, its biological activity. Potency of an agent can be determined by any suitable method known in the art, such as for instance as described in the examples section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, reporter gene assays, cell surface receptor binding assays and assays to measure induction/inhibition of functionally essential protein or other signal molecule (such as phosphorylated proteins, enzymes, cytokines, cAMP and the like), all well known in the art. Results from cell based potency assays can be expressed as "relative potency" as determined by comparison of the dimer of the invention to the response obtained for the corresponding benchmark (cf. examples section).

A compound, e.g. the dimer of the invention, is said to be more potent than a benchmark, e.g. the reference compound, such as a construct comprising the corresponding polypeptides, when the response obtained for the compound, e.g. the dimer of the invention, is at least 1.5 times, such as 2 times, but preferably at least 3 times, such as at least 4 times, at least 5 times, at least 6 times, at least 7 times, at least 8 times, at least 9 times, at least 10 times, at least 15 times, at least 20 times, at least 25 times, at least 50 times, at least 75 times, and even more preferably even at least 100 times, or more better (e.g. functionally better) than the response by the reference compound, e.g. the corresponding benchmark in a given assay.

The efficacy or potency of the dimers, immunoglobulin single variable domains and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include ligand displacement assays (e.g. Burgess et al., Cancer Res 2006 66:1721-9), dimerization assays (e.g. WO2009/007427A2, Goetsch, 2009), signaling assays (e.g. Burgess et al., Mol Cancer Ther 9:400-9), proliferation/survival assays (e.g. Pacchiana et al., J Biol Chem 2010 September M110.134031), cell adhesion assays (e.g. Holt et al., Haematologica 2005 90:479-88) and migration assays (e.g. Kong-Beltran et al., Cancer Cell 6:75-84), endothelial cell sprouting assays (e.g. Wang et al., J Immunol. 2009; 183:3204-11), and in vivo xenograft models (e.g. Jin et al., Cancer Res. 2008 68:4360-8), as well as the assays and animal models used in the experimental part below and in the prior art cited herein. A means to express the inhibition of said first target in vitro is by $IC_{50}$.

In particular, the dimers of the invention bind to a target with an affinity (suitably measured and/or expressed as a $K_D$-value (actual or apparent), a $K_A$-value (actual or apparent), a $k_{on}$-rate and/or a $k_{off}$-rate better than the benchmark.

In an embodiment, the present invention relates to a dimer comprising polypeptides as described herein, wherein said dimer binds to a target with an $IC_{50}$ which is at least 10%, such as 20%, 30%, 50%, 80%, 90%, or even 100% better or more than the $IC_{50}$ of a benchmark, for instance as determined in a ligand competition assay, competition FACS, a functional cellular assay, such as inhibition of ligand-induced chemotaxis, an ALPHASCREEN® assay, etc., preferably by a competition FACS.

In an embodiment, the present invention relates to a dimer comprising polypeptides as described herein, wherein said dimer binds to a target with an $IC_{50}$ which is at least 1.5 times, such as 2 times, 3 times or 4 times, and even 5 times or 10 times better than the $IC_{50}$ of a benchmark, for instance as determined in a ligand competition assay, competition FACS, a functional cellular assay, such as inhibition of ligand-induced chemotaxis, an ALPHASCREEN® assay, etc., preferably by a competition FACS.

In an embodiment, the present invention relates to a dimer comprising polypeptides as described herein, having an $IC_{50}$ of between 200 nM and 0.01 nM, such as 0.01, 0.05, 0.1, 0.15, 2, 3, 4, 5, 6, 7, 8, 9, 10, 15, 20, 30, 40, 50, 60, 70, 80, 90, 100, 110, 120, 130, 140, 150, 160, 170, 180, 190 or 200 nM, for instance determined in a ligand competition assay, competition FACS, a functional cellular assay, such as inhibition of ligand-induced chemotaxis, an ALPHASCREEN® assay, etc.

Transport, manufacture, storage and delivery processes can exert manifold stresses on polypeptides, such as chemical and physical stresses. During storage chemical modifications can occur such as, for instance, deamidation, racemization, hydrolysis, oxidation, isomerization, beta-elimination or disulfide exchange. Physical stresses can cause denaturation and unfolding, aggregation, particulate formation, precipitation, opalescence or adsorption. It is known that these stresses can affect the physicochemical integrity of protein therapeutics, e.g. antibody therapeutics.

As noted supra, the inventors observed that the dimers of the invention have unexpected favourable binding and functional characteristics. These characteristics were also retained for prolonged periods of time, without any apparent or substantive loss of potency. This makes the dimers useful for storage and transport. The invention provides stable dimers of the invention. "Stable" generally means that the dimers do not suffer from significant physical or chemical changes, in particular oxidation, upon storage for prolonged periods of time, e.g. 1 month to 36 months, even if exposed to one or more chemical or physical stresses such as elevated temperatures (equal to or higher than +25° C.), or physical stress such as shaking or stirring. More in particular, "stable" means that upon storage for prolonged periods (as defined) under conditions (as defined) there is only a limited formation of one or more of degradation products, e.g. low molecular weight (LMW) derivatives (e.g. polypeptides) of the dimers of the invention; and/or high molecular weight (HMW) derivatives (oligomers or polymers) formed e.g. by aggregation of the dimers.

Accordingly, the present invention relates to a dimer as described herein, wherein said dimer is stable for at least 2 months, such as 4 months, 6 months, 12 months or even longer, such as 18 months, 24 months or 36 months at −20° C., +4° C., room temperature, e.g. +20° C. or even at +25° C., wherein said stability is characterized by a limited formation or no formation of LMW and/or HMW, e.g. less than 10%, such as less than 5%, less than 2% or even no detectable LMW and/or HMW.

General techniques that can be used to assess stability of a protein include static light scattering, tangential flow filtration, Fourier transform infrared spectroscopy, circular dichroism, urea induced protein unfolding, intrinsic tryptophan fluorescence and/or 1-anilin-β8-naphtalenesulfonic acid protein binding. These techniques are applicable to the dimers of the invention as well. In addition, the dimers of the invention show little or no loss of potency/biological activity in the course of storage and/or under influence of one or more stresses as defined herein.

Accordingly the present invention relates to a method for storing polypeptides comprising reactive cysteine moieties, comprising at least the step of oxidizing the thiol moiety of said reactive cysteine moiety to the disulfide derivative cystine, thereby temporarily inactivating said reactive cysteine moieties, wherein said polypeptides further comprise (internal) cystine bonds.

Notwithstanding the favourable functional properties of the dimers of the invention, the present inventors hypothesized that the dimers might be particularly suited as a pool for instantaneous use, such as, for instance, coupling of functional groups using the C-terminal cysteine, e.g. by maleimide chemistry. A protocol with mild reducing conditions was developed, in which the intermolecular disulfide bridge of the dimer was reduced to activate the thiol group of the constituent polypeptides.

Optimized conditions resulted in reduction of the disulfide forming the dimer without reducing the internal canonical ISVD disulfide bridges.

Preferred reductants are acid based reductants, such as Oxalic acid ($C_2H_2O_4$), Formic acid (HCOOH), Ascorbic acid ($C_6H_8O_6$), phosphorous acid, or β-mercaptoethanol, Lithium aluminum hydride ($LiAlH_4$), Nascent (atomic) hydrogen, Sodium amalgam, Diborane, Sodium borohydride ($NaBH_4$), Compounds containing the $Sn^{2+}$ ion, such as tin(II) chloride, Sulfite compounds, Hydrazine, Zinc-mercury amalgam (Zn(Hg)), Diisobutylaluminum hydride (DIBAL-H), Lindlar catalyst, Phosphites, hypophosphites, compounds containing Fe', such as iron(II) sulfate, Carbon monoxide (CO), Carbon (C), Dithiothreitol (DTT) and Tris (2-carboxyethyl)phosphine HCl (TCEP), preferably DTT and TCEP.

Preferred final concentrations of the reductants are between 50 mM and 1 mM, such as between 40 mM and 2 mM, between 30 mM and 5 mM, and 20 mM and 7.5 mM, preferably 10 mM.

It was determined that an overnight treatment with 10 mM DTT at 4° C. (or during at least 2 h at room temperature) was very suitable for reducing the intermolecular disulfide bond of ISVDs at concentrations up to 10 mg/ml, but without affecting the internal canonical disulfide bonds. Reduction can be carried out preferably using DTT or TCEP. Unlike TCEP, DTT is preferably removed to create optimal coupling conditions. Via Size Exclusion Chromatography (SEC) monomeric polypeptides can be separated from the non-reduced dimer and DTT.

The extent of reduction can be monitored via any means known in the art, such as for instance via SEC or SDS-PAGE in non-reducing conditions.

Accordingly the present invention relates to a method as described herein, further comprising the step of reducing said (C-terminal) cystine of said dimer, preferably under conditions wherein internal disulfide bonds of said first polypeptide and/or said second polypeptide remain oxidized.

Accordingly the present invention relates to a method for generating polypeptides comprising reactive cysteine moieties, comprising at least the steps of:

(i) providing polypeptides according to the invention, which are dimerized via a cystine (disulfide bond; SS-bond or disulfide bridge between two cysteines);

(ii) reducing said cystine;

thereby generating polypeptides comprising reactive cysteine moieties; preferably said cystine bond is located at the C-terminal end of said polypeptides. Preferably, the reducing conditions of said step (ii) are chosen such that the internal cystine bonds are not reduced.

After reduction of the dimers, the reduced monomeric polypeptides are preferably used immediately, e.g. within 0.5 h but preferably within 10 minutes, for conjugation or are frozen to prevent re-oxidation, although re-oxidation is not prevented completely by freezing. Experimental evidence suggest that the reduced monomeric polypeptides of the invention are stable up to 24 h at 4° C. in D-PBS.

In an embodiment, the dimers and the constituent polypeptides of the invention comprise one or more functional groups, residues or moieties. In an embodiment the present invention relates to a dimer as described herein, which further comprises one or more other groups, residues, moieties or binding units. In an embodiment the present invention relates to a dimer as described herein, wherein said first polypeptide and/or said second polypeptide further comprises one or more other groups, residues, moieties or binding units. For instance, functional groups, residues or moieties can be coupled or linked to the (reactive) thiol moiety of the cysteine residue at the C-terminus of the polypeptide and/or functional groups, residues or moieties can be coupled or linked to the N-terminus of the polypeptide of the invention. In an embodiment, one or both N-termini of the dimer of the invention comprises functional groups, residues or moieties.

Examples of such groups, residues or moieties and methods and techniques that can be used to attach such groups, residues or moieties and the potential uses and advantages of such groups, residues or moieties will be clear to the skilled person. Without being limiting, thiol reactive groups for antibody modification include maleimide, vinylsulphone, haloacetyl or pyridyl disulphide groups. Maleimides react selectively with cysteines at neutral pH, although there is reactivity with amine groups at higher pH values. A stable thioether bond is generated.

One or more functional groups, residues or moieties may be attached to the dimer and/or polypeptide of the invention that confer one or more desired properties or functionalities to the dimer and/or polypeptide of the invention. Example of such functional groups, residues or moieties will be clear to the skilled person. For example, such one or more functional groups, residues or moieties may increase the half-life, the solubility and/or the absorption of the dimer and/or polypeptide of the invention, such one or more functional groups, residues or moieties may reduce the immunogenicity and/or the toxicity of the dimer and/or polypeptide of the invention, such one or more functional groups, residues or moieties may eliminate or attenuate any undesirable side effects of the dimer and/or polypeptide of the invention, and/or such one or more functional groups, residues or moieties may confer other advantageous properties to and/or reduce the undesired properties of the dimer and/or polypeptide of the invention; or any combination of two or more of the foregoing. Examples of such functional groups, residues or moieties and of techniques for introducing them will be clear to the skilled person, and can generally comprise all functional groups, residues or moieties and techniques mentioned in the general background art cited herein as well as the functional groups, residues or moieties and techniques known per se for the modification of pharmaceutical proteins, and in particular for the modification of antibodies or antibody fragments (including ScFv's and single domain antibodies), for which reference is for example made to Remington's Pharmaceutical Sciences, 16$^{th}$ ed., Mack Publishing Co., Easton, Pa. (1980).

In view of the specificity, the dimers and/or polypeptides of the invention are also very suitable for conjugation to imaging agents. Suitable imaging agents for conjugating to antibodies are well known in the art, and similarly useful for conjugating to the dimers and/or polypeptides of the present invention. Suitable imaging agents include but are not limited to molecules preferably selected from the group consisting of organic molecules, enzyme labels, radioactive labels, colored labels, fluorescent labels, chromogenic labels, luminescent labels, haptens, digoxigenin, biotin, metal complexes, metals, colloidal gold, fluorescent label, metallic label, biotin, chemiluminescent, bioluminescent, chromophore and mixtures thereof.

Accordingly, the present invention relates to a dimer and/or polypeptide according to the invention, further comprising an imaging agent, including, but not limited to a molecule preferably selected from the group consisting of organic molecules, enzyme labels, radioactive labels, colored labels, fluorescent labels, chromogenic labels, luminescent labels, haptens, digoxigenin, biotin, metal complexes, metals, colloidal gold, fluorescent label, metallic label, biotin, chemiluminescent, bioluminescent, chromophore and mixtures thereof.

One or more detectable labels or other signal-generating groups, residues or moieties may be coupled to the dimer and/or polypeptide of the invention, depending on the intended use of the labelled polypeptide. Suitable labels and techniques for attaching, using and detecting them will be clear to the skilled person, and for example include, but are not limited to, the fluorescent labels, phosphorescent labels, chemiluminescent labels, bioluminescent labels, radio-isotopes, metals, metal chelates, metallic cations, chromophores and enzymes, such as those mentioned on page 109 of WO 08/020079. Radioisotopes and radionuclides known in the art for their utility as detection agents include, but are not limited to, $^{3}$H $^{14}$C $^{15}$N $^{18}$F $^{35}$S $^{64}$Cu $^{67}$Cu $^{75}$Br $^{76}$Br $^{77}$Br $^{89}$Zr $^{90}$Y $^{97}$Ru $^{99}$Tc $^{105}$Rh $^{109}$Pd $^{111}$In $^{123}$I $^{124}$I $^{125}$I $^{131}$I $^{149}$Pm $^{153}$Sm $^{166}$Ho $^{177}$Lu $^{185}$Re $^{188}$Re $^{198}$Au $^{199}$Au $^{203}$Pb $^{211}$At $^{212}$Pb $^{212}$Bi $^{213}$Bi $^{223}$Ra $^{225}$Ac. Indium$^{111}$ is particularly preferred as the diagnostic radionuclide because: between about 1 to about 10 mCi can be safely administered without detectable toxicity; and the imaging data is generally predictive of subsequent PDC distribution (see infra). See, for example, Murray J. L., 26 J. Nuc. Med. 3328 (1985) and Carraguillo, J. A. et al, 26 J. Nuc. Med. 67 (1985).

Other suitable labels will be clear to the skilled person, and for example include moieties that can be detected using NMR or ESR spectroscopy. For instance, the polypeptides of the invention can be radiolabeled with $^{89}$Zr as exemplified in the Examples section. Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label. In a preferred embodiment, the radiolabeled polypeptides and/or dimers of the invention are detected via microPET imaging. Images can be reconstructed using AMIDE Medical Image Data Examiner software (version 1.0.4, Stanford University).

A functional group, residue or moiety may be attached that is one part of a specific binding pair, such as the biotin-(strept)avidin binding pair. Such a functional group may be used to link the dimer and/or polypeptide of the invention to another protein, polypeptide or chemical compound that is bound to the other half of the binding pair, i.e. through formation of the binding pair. For example, a dimer and/or polypeptide of the invention may be conjugated to biotin, and linked to another protein, polypeptide, compound or carrier conjugated to avidin or streptavidin. For example, such a conjugated dimer and/or polypeptide may be used as a reporter, for example in a diagnostic system where a detectable signal-producing agent is conjugated to avidin or streptavidin. Such binding pairs may for example also be used to bind the dimer and/or polypeptide of the invention to a carrier, including carriers suitable for pharmaceutical purposes. One non-limiting example are the liposomal formulations described by Cao and Suresh 2000 (Journal of Drug Targeting 8 (4): 257). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw 1997 (Biotechnol. Appl. Biochem. 26: 143-151).

In some embodiments, the dimers and/or polypeptides of the invention are conjugated with drugs to form dimer/polypeptide-drug conjugates (collectively abbreviated as "PDCs" herein). Contemporaneous antibody-drug conjugates (ADCs) are used in oncology applications, where the use of antibody-drug conjugates for the local delivery of drugs, such as cytotoxic or cytostatic agents, toxins or toxin moieties, allows for the targeted delivery of the drug moiety to tumors, which can allow higher efficacy, lower toxicity, etc. These ADCs have three components: (1) a monoclonal antibody conjugated through a (2) linker to a (3) drug moiety, such as a toxin moiety or toxin. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety. The PDCs of the present invention also have three components: (1) a dimer or polypeptide conjugated through a (2) linker to a (3) drug, such as a toxin moiety or toxin. As noted above, although the conjugation of linkers and drugs has a greater, and unfavourable effect on the aggregation, biodistribution and PK profile of antibody fragments, such as the polypeptide of the invention, than the larger sized antibody, the person skilled in the art will appreciate that the technology, methods, means, etc. of ADCs are in general equally applicable to PDCs (cf. Feng et al. supra).

The invention provides polypeptides of the invention (whether or not comprised in the dimer of the invention) comprising a drug, such as a toxin or toxin moiety. For the sake of completeness, the invention provides a dimer of the invention comprising a drug, such as a toxin or toxin moiety.

The drug, e.g. toxin moiety or toxin can be linked or conjugated to the dimer and/or polypeptide using any suitable method. Generally, conjugation is done by covalent attachment to the dimer and/or polypeptide, as known in the art, and generally relies on a linker, often a peptide linkage. For example, the drug, such as a toxin moiety or toxin can be covalently bonded to the polypeptide directly or through a suitable linker. Suitable linkers can include non-cleavable or cleavable linkers, for example, pH cleavable linkers that comprise a cleavage site for a cellular enzyme (e.g., cellular esterases, cellular proteases such as cathepsin B, see e.g. examples section). Such cleavable linkers can be used to prepare a ligand that can release a drug, such as a toxin moiety or toxin after the polypeptide is internalized. As will be appreciated by those in the art, the number of drug moieties per dimer and/or polypeptide can change, depending on the conditions of the reaction, and can vary from 1:1 to 20:1 drug:polypeptide (also indicated as drug-antibody ratio or DAR). As will also be appreciated by those in the art, the actual number is an average, when the reaction and/or purification is not tightly controlled. Preferably, the dimer of the invention further comprising a drug, wherein the drug to dimer ratio (DAR) is 1. A variety of methods for linking or conjugating a drug, such as a toxin moiety or toxin, to a dimer and/or polypeptide can be used. The particular method selected will depend on the drug, such as a toxin moiety or toxin, and the dimer and/or polypeptide to be linked or conjugated. If desired, linkers that contain terminal functional groups can be used to link the dimer and/or polypeptide and drug, e.g. a toxin moiety or toxin. Generally, conjugation is accomplished by reacting the drug, e.g. a toxin moiety or toxin, that contains a reactive functional group (or is modified to contain a reactive functional group) with a linker or directly with a dimer and/or polypeptide. Covalent bonds formed by reacting a drug, e.g. a toxin moiety or toxin, that contains (or is modified to contain) a chemical moiety or functional group that can, under appropriate conditions, react with a second chemical group thereby forming a covalent bond. If desired, a suitable reactive chemical group can be added to polypeptide or to a linker using any suitable method (see, e.g., Hermanson, G. T., Bioconjugate Techniques, Academic Press: San Diego, Calif. (1996)). Many suitable reactive chemical group combinations are known in the art, for example an amine group can react with an electrophilic group such as tosylate, mesylate, halo (chloro, bromo, fluoro, iodo), N-hydroxysuccinimidyl ester (NHS), and the like. Thiols can react with maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, supra).

As shown in the examples, it was unexpectedly found that the polypeptides of the present invention comprising a C-terminal extension comprising a cysteine moiety at the C-terminus were remarkably suited for conjugating in a very controlled manner a specific number of drugs per polypeptide, e.g. DAR of 1. This results in a better controlled efficacy and safety profile compared to the prior art molecules. Accordingly, the present invention relates to polypeptides as described herein comprising a single conjugated drug, e.g. DAR=1. The process of the invention thus allows polypeptides and dimers to be produced with improved homogeneity.

As described below, the drug of the PDC can be any number of agents, including but not limited to cytostatic agents, cytotoxic agents such as chemotherapeutic agents, growth inhibitory agents, toxins (for example, an enzymatically active toxin of bacterial, fungal, plant, or animal origin, or fragments thereof), toxin moieties, or a radioactive isotope (that is, a radioconjugate) are provided. In other embodiments, the invention further provides methods of using the PDCs. The present invention also relates to Radioimmunotherapy (RIT), in which a polypeptide or dimer of the invention is labelled with a radioactive isotope to deliver cytotoxic radiation to a target cell.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues, preferably MMAE. Preferably said polypeptide conjugated to a toxin is chosen from the group consisting of ABL 100-NC003-1, ABL 100-NC003-3, ABL 100-NC003-5, ABL 100-NC003-6 and ABL 100-BF012-1, most preferably ABL 100-BF012-1.

Drugs, such as toxins may be used as polypeptides-toxin conjugates and/or dimer-toxin conjugates and include bacterial toxins such as diphtheria toxin, plant toxins such as ricin, small molecule toxins such as geldanamycin (Mandler et al. (2000) J. Nat. Cancer Inst. 92(19):1573-1581; Mandler et al. (2000) Bioorganic & Med. Chem. Letters 10:1025-1028; Mandler et al. (2002) Bioconjugate Chem. 13:786-791), maytansinoids (EP 1391213; Liu et al. (1996) Proc. Natl. Acad. Sci. USA 93:8618-8623), and calicheamicin (Lode et al. (1998) Cancer Res. 58:2928; Hinman et al. (1993) Cancer Res. 53:3336-3342). Toxins may exert their cytotoxic and cytostatic effects by mechanisms including tubulin binding, DNA binding, or topoisomerase inhibition.

Conjugates of a polypeptide and/or dimer of the invention and one or more small molecule toxins, such as a maytansinoids, dolastatins, auristatins, a trichothecene, calicheamicin, and CC1065, and the derivatives of these toxins that have toxin activity, are contemplated.

Other drugs, such as antitumor agents that can be conjugated to the dimers and/or polypeptides of the invention include BCNU, streptozotocin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Drugs, such as enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates a PDC formed between a dimer and/or polypeptide of the invention and a compound with nucleolytic activity (e.g., a ribonuclease or a DNA endonuclease such as a deoxyribonuclease; DNase).

For selective destruction of the tumor, the dimer and/or polypeptide of the invention may comprise a highly radioactive atom. A variety of radioactive isotopes are available for the production of radioconjugated PDCs. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

The radio- or other labels may be incorporated in the conjugate in known ways. For example, the polypeptide may be biosynthesized or may be synthesized by chemical amino acid synthesis using suitable amino acid precursors involving, for example, fluorine-19 in place of hydrogen. Labels such as $Tc^{99m}$ or $I^{123}$, $Re^{186}$, $Re^{188}$ and $In^{111}$ can be attached via a cysteine residue in the peptide. Yttrium-90 can be attached via a lysine residue. The Iodogen method (Fraker et al. (1978) Biochem. Biophys. Res. Commun. 80: 49-57 can be used to incorporate Iodine-123. Iodine-125 can be radiolabeled by the iodobead method as described in Valentine, M. A. et al., (1989) J. Biol. Chem. 264:11282. "Monoclonal Antibodies in Immunoscintigraphy" (Chatal, CRC Press 1989) describes other methods in detail.

The person skilled in the art can establish effective single treatment dosages (e.g. therapeutically effective amounts) of radioconjugated PDCs, which depend inter alia on the specific radiolabel, half-life of the PDC, toxicity, target etc. Preferably, the effective single treatment dosages range preferably from between about 5 and about 75 mCi, more preferably between about 10 and about 40 mCi.

The generation of PDC compounds can be accomplished by any technique known to the skilled artisan in the field of ADCs. Briefly, the PDC compounds can include dimer and/or polypeptide of the invention as the Antibody unit, a drug, and optionally a linker that joins the drug and the binding agent.

Methods of determining whether a drug or an antibody-drug conjugate exerts an effect, e.g. a cytostatic and/or cytotoxic effect on a cell are known. Generally, the effect, e.g. a cytotoxic or cytostatic activity of an Antibody Drug Conjugate can be measured by: exposing mammalian cells expressing a target protein of the Antibody Drug Conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug Conjugate. These methods are equally applicable to PDCs.

Accordingly the invention relates to a polypeptide of the invention (whether or not comprised in the dimer of the invention) further comprising a drug, such as a toxin or toxin moiety. For the sake of clarity, the invention relates to a dimer (comprising polypeptides of the invention) further comprising a drug, such as a toxin or toxin moiety.

Accordingly, the present invention relates to a polypeptide according to the invention (whether or not comprised in the dimer of the invention) conjugated to a drug, such as a toxin or toxin moiety. For the sake of clarity, the invention relates to a dimer (comprising polypeptides of the invention) conjugated to a drug, such as a toxin or toxin moiety.

PDCs combine the selectivity of a highly selective targeting moiety with the killing potency of a drug. For the polypeptide according to the invention (whether or not comprised in the dimer of the invention) to function as a successful component of a PDC, the polypeptide needs to bind to the target antigen on the surface of the target cell, e.g. a tumor cell. For most drugs the PDC is to be internalized by the cell in order to be efficacious (Trail 2013 Antibodies 2:113-129 review). Following internalization, the PDC is transported to the lysosome where subsequent intracellular processing of the PDC will release the biologically active drug to exert its (toxic) effects on the target cell, such as a tumor cell. Not only biologically active drugs should be internalized, but also radioactive isotopes for radio-immunotherapy (RIT) are preferably internalized, in order to highly localize the toxic effects of the radioactive payload. The precise targeting by the radiolabeled polypeptides of the invention (whether or not comprised in the dimer of the invention) causes selective and extremely effective cytotoxicity of target cells (e.g. tumor cells) at relatively low doses of radioactivity, minimizing side-effects.

The inventors demonstrated that the overall internalization of the dimers of the invention appeared to be more potent and efficacious than the corresponding monomers and the bivalent benchmarks, especially in cells with a low number of targets. This difference in internalization is less pronounced yet still significant in cells that express a target in extreme high levels.

Accordingly, the present invention relates to a dimer of the invention for use in the treatment of cancer, wherein said dimer internalizes. Preferably said dimer is conjugated to a (cytotoxic) drug.

Accordingly, the present invention relates to the use of a dimer of the invention for the manufacture of a medicament for the treatment of cancer, wherein said dimer internalizes. Preferably said dimer is conjugated to a (cytotoxic) drug.

In an embodiment, the dimer of the invention can be used to target cells expressing a low number of binding sites for the corresponding ISVDs, such as less than $10*10^5$ binding sites, such as $5*10^5$ binding sites, or even less than $10*10^4$ binding sites, $5*10^4$ binding sites, $1*10^4$ binding sites, or less than 5000 binding sites, e.g. less than 4000, 3000 or even less than 2000 binding sites such as 1000 binding sites or even less.

In an embodiment, the present invention relates to a dimer as described herein for use in the treatment of cancer, wherein said dimer internalizes. Preferably said dimer is conjugated to a (cytotoxic) drug.

In an embodiment, the present invention relates to the use of a dimer as described herein for the manufacture of a medicament for the treatment of cancer, wherein said dimer internalizes. Preferably said dimer is conjugated to a (cytotoxic) drug.

Most drugs used in cancer treatment are hydrophobic. This is advantageous, since these hydrophobic drugs can penetrate the cell membrane. However, these drugs can penetrate any membrane, also from non-cancerous cells. Still these drugs are efficacious since the cancer cells divide more rapidly than "normal" cells. It will be appreciated that the use of these drugs comes with serious side-effects. In order for a more targeted approach, several of these drugs have been coupled to conventional antibodies, which are used as a vehicle to preferably target the cancer cell. These conventional antibodies have a size of about 150 kD, while the drugs have on average a size of about 1 kD. Hence, the size ratio of antibody:drug is about 150:1. This ratio is one of the reasons that the hydrophobicity of the drug is of little influence of the antibody drug conjugate (ADC) in total.

It has been demonstrated that the physicochemical properties of the ISVDs are exceedingly dependent on its surface exposed amino acids that become solvent exposed. This is reflected in the large number of different formulations used for ISVDs. In vast contrast to a conventional antibody, an ISVD has a size of only about 15 kD. Consequently, the size ratio of ISV:drug is only 15:1, i.e. 10 times less than for conventional antibodies. Accordingly, the hydrophobic characteristics of a drug have a disproportionately larger influence on the properties of the PDC. Indeed, a main problem with PDCs is aggregation. Nevertheless, it was surprisingly observed that the PDCs of the invention were stable, were amenable to administration in vivo and were able to reduce tumor growth in vivo.

In an embodiment, the present invention provides a polypeptide conjugated to a toxin as described herein or a dimer conjugated to a toxin for use in treating a subject in need thereof.

The present invention relates to a dimer as described above for use in therapy, preferably for use in the treatment of cancer. Also, the present invention relates to the use of a dimer as described above for the manufacture of a medicament for the treatment of cancer.

The term "cancer" refers to any cancer caused by the proliferation of malignant neoplastic cells, such as tumors, neoplasms, carcinomas, sarcomas, leukemia's, and lymphomas. Cancers of interest for treatment include, but are not limited to, carcinoma, lymphoma, blastoma, sarcoma, leukemia, lymphoid malignancies, cancer of the breast, cancer of the ovary, cancer of the testis, cancer of the lung, cancer of the colon, cancer of the rectum, cancer of the pancreas, cancer of the liver, cancer of the central nervous system, cancer of the head and neck, cancer of the kidney, cancer of the bone, cancer of the blood or cancer of the lymphatic system. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer including, for example, HER2-positive breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain cancer, head and neck cancers, and associated metastases.

A "solid tumor cancer" is a cancer comprising an abnormal mass of tissue. In some embodiments, the cancer is a solid tumor cancer (e.g., carcinomas, and lymphomas breast cancer, non-small cell lung cancer, prostate cancer, pancreatic cancer, head and neck cancer, colon cancer, sarcoma, or adrenocortical carcinoma).

The present invention provides a method for treating and/or preventing and/or alleviating disorders relating to cancer (for instance as defined above).

As used herein, and as well understood in the art, "to treat" a condition or "treatment" of the condition (e.g., the conditions described herein such as cancer) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term an "effective amount" of an agent (e.g., any of the foregoing conjugates), as used herein, is that amount sufficient to effect beneficial or desired results, such as clinical results, and, as such, an "effective amount" depends upon the context in which it is being applied.

By "subject" is meant a human or non-human animal (e.g., a mammal).

The present invention relates to a method of treating cancer which comprises the administration to a patient of a dimer of the invention.

The present invention provides also method for treating and/or preventing and/or alleviating disorders relating to rheumatoid arthritis, psoriasis, or hypersecretion of mucus in the lung, comprising administering to a subject in need of such treatment (an effective amount of) a polypeptide conjugated to a toxin as described herein.

The present invention provides a method for delivering a prophylactic or therapeutic polypeptide or dimer conjugated to a toxin to a specific location, tissue or cell type in the body, the method comprising the steps of administering to a subject a polypeptide conjugated to a toxin as described herein or a dimer conjugated to a toxin as described herein. The present invention provides a method for treating a subject in need thereof comprising administering a polypeptide conjugated to a toxin as described herein.

In an embodiment, the present invention relates to a pharmaceutical composition comprising a polypeptide conjugated to a toxin as described above or a dimer conjugated to a toxin as described herein. The present invention provides a dimer of the invention, together with a pharmaceutically acceptable carrier; optionally together with an additional agent.

Accordingly, the present invention provides a polypeptide of the invention, whether or not comprised in the dimer of the invention, conjugated to a drug, such as a toxin or toxin moiety as described herein. Preferably said polypeptide comprises an ISV directed against EGFR, potentially further comprising an ISVD directed against serum albumin.

In an embodiment, the present invention provides a polypeptide conjugated to a toxin as described herein, wherein at least one ISVD inhibits and/or blocks the interaction between Epidermal Growth Factor (EGF) and EGFR.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

In an embodiment, the present invention relates to a composition comprising the dimer of the invention, preferably, said composition is a pharmaceutical composition, optionally further comprising at least one pharmaceutically acceptable carrier, diluent or excipient and/or adjuvant, and that optionally comprises one or more further pharmaceutically active polypeptides and/or compounds. The compositions containing an effective amount can be administered for radiation treatment planning, diagnostic, or therapeutic treatments. When administered for radiation treatment planning or diagnostic purposes, the conjugate is administered to a subject in a diagnostically effective dose and/or an amount effective to determine the therapeutically effective dose. In therapeutic applications, compositions are administered to a subject (e.g., a human) already suffering from a condition (e.g., cancer) in an amount sufficient to cure or at least partially arrest the symptoms of the disorder and its complications. An amount adequate to accomplish this purpose is defined as a "therapeutically effective amount," an amount of a compound sufficient to substantially improve at least one symptom associated with the disease or a medical condition. For example, in the treatment of cancer, an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual. The dimers of the invention can be used for the treatment of cancer by administering to a subject a first dose of any of the foregoing dimers or compositions in an amount effective for radiation treatment planning, followed by administering a second dose of any of the foregoing dimers or compositions in a therapeutically effective amount.

Amounts effective for these uses may depend on the severity of the disease or condition and the weight and general state of the subject. The therapeutically effective amount of the dimers and compositions of the invention and used in the methods of this invention applied to mammals (e.g., humans) can be determined by the ordinarily-skilled artisan with consideration of individual differences in age, weight, and the condition of the mammal. Because certain PDCs of the invention exhibit an enhanced ability to target cancer cells and residualize, the dosage of the compounds of the invention can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated agent. The agents of the invention are administered to a subject (e.g., a mammal, such as a human) in an effective amount, which is an amount that produces a desirable result in a treated subject. Therapeutically effective amounts can also be determined empirically by those of skill in the art. Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The dimers of the present invention may be used in combination with either conventional methods of treatment or therapy or may be used separately from conventional methods of treatment or therapy.

When the dimers of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

Generally, for pharmaceutical use, the dimers and/or polypeptides of the invention may be formulated as a pharmaceutical preparation or composition comprising at least one dimer and/or polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc, wherein the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one polypeptide of the invention or at least one dimer of the invention and at least one suitable carrier, diluent or excipient (i.e., suitable for pharmaceutical use), and optionally one or more further active substances.

Generally, the polypeptides and/or dimers of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

The polypeptides and/or dimers of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

Thus, the polypeptides and/or dimers of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides and/or dimers of the invention may be combined with one or more excipients and used in the form of ingestible tablets, buccal tablets, troches, capsules, elixirs, suspensions, syrups, wafers, and the like. Such compositions and preparations should contain at least 0.1% of the polypeptide and/or dimer of the invention. Their percentage in the compositions and preparations may, of course, be varied and may conveniently be between about 2 to about 60% of the weight of a given unit dosage form. The amount of the polypeptide and/or dimer of the invention in such therapeutically useful compositions is such that an effective dosage level will be obtained.

The tablets, troches, pills, capsules, and the like may also contain binders, excipients, disintegrating agents, lubricants and sweetening or flavoring agents, for example those mentioned on pages 143-144 of WO 08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides, compounds and/or constructs of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides and/or dimers of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The polypeptides and/or dimers of the invention may also be administered intravenously or intraperitoneally by infusion or injection. Particular examples are as further described on pages 144 and 145 of WO 08/020079 or in PCT/EP2010/062975 (entire document).

For topical administration, the polypeptides and/or dimers of the invention may be applied in pure form, i.e., when they are liquids. However, it will generally be desirable to administer them to the skin as compositions or formulations, in combination with a dermatologic acceptable carrier, which may be a solid or a liquid. Particular examples are as further described on page 145 of WO 08/020079.

Useful dosages of the polypeptides, compounds and/or constructs of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the polypeptides and/or dimers of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the polypeptides and/or dimers of the invention required for use in treatment will vary not only with the particular polypeptide and/or dimer selected but also with the route of administration, the nature of the condition being treated and the age and condition of the patient and will be ultimately at the discretion of the attendant physician or clinician. Also the dosage of the polypeptides and/or dimers of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. The dosage can also be adjusted by the individual physician in the event of any complication.

Examples

1 Generation of Building Blocks

Various constructs were generated in *P. pastoris*, starting from the EGFR binding Nanobodies 7D12 and 9G08, and an albumin binding Nanobody ALB11 as depicted in Table 4.

TABLE 4

Constructs

| Product Name | Building Blocks |
|---|---|
| T023800001-A | 7D12-20GS-ALB11-GGC-A |
| T023800003-A | 7D12-20GS-7D12-GGC-A |
| T023800005-A | 7D12-20GS-9G08-GGC-A |
| T023800006-A | 7D12-20GS-7D12-20GS-ALB11-GGC-A |
| T023800008-A | 7D12-20GS-9G08-20GS-ALB11-GGC-A |
| T023800001-dimer | $_N$[7D12-ALB11-GGC]$_C$-S-S-$_C$[CGG-ALB11-7D12]$_N$ |

1.1 Genetic Fusion

The coupling of the building blocks 7D12 and Alb11 and linkers in various transpositions (order) in T023800001, T023800003, T023800005 and T023800006 was performed by genetic fusion according to standard protocols, for instance as described by Garaicoechea et al. (Garaicoechea et al. (2008) J Virol. 82: 9753-9764). Polypeptides were generated comprising various linker lengths and compositions (order of ISVDs and individual ISVDs). C-terminal extensions, including GGC, were constructed also by genetic fusions. The sequences of T023800001 (SEQ ID NO: 27), T023800003 (SEQ ID NO: 28), T023800005 (SEQ ID NO: 29) and T023800006 (SEQ ID NO: 30) and T023800008 (SEQ ID NO: 31) are provided in Table 6.

The feasibility of constructing different C-terminal extensions comprising a cysteine moiety at the C-terminus was demonstrated by manufacturing various polypeptides with different C-terminal extensions: -C (SEQ ID NO: 1), -GC (SEQ ID NO: 2), -GGC (SEQ ID NO: 3), -GGGC (SEQ ID NO: 4), -CG (SEQ ID NO: 10), -GCG (SEQ ID NO: 11), -GGGCG (SEQ ID NO: 13), -GGGGCGGG (SEQ ID NO: 15) and -AAAC (SEQ ID NO: 8) (data not shown).

1.2 Alanine Extension

An alanine moiety (N-Maleoyl-β-alanine; Sigma-Aldrich) was conjugated via maleimide chemistry to the sulfhydryl group (—SH) of the C-terminally located cysteine at near neutral conditions (pH 6.5-7.5) to form stable thioether linkages according to well established protocols (see below). In short, first the concentration of the polypeptide at issue was determined. A 2-5 molar excess of N-Maleoyl-β-alanine was added to the polypeptide to block all available cysteines. The mixture was incubated for 1 h at RT followed by an overnight incubation at 4° C. The conjugation efficiency was confirmed via LC MS on the next day. The polypeptides comprising the Ala-extension were purified to homogeneity via SEC chromatography to remove excess N-Maleoyl-β-alanine.

The resulting constructs were designated 7023800001-A, T023800003-A, T023800005-A and T023800006-A (FIG. 1; Table 4).

It was further demonstrated that also an Alanine could be conjugated to constructs with C-terminal extensions comprising cysteine that were different from GGC (see also 1.1 above; data not shown).

1.3 Dimerization

The coupling of the polypeptides into a dimer was performed by chemical conjugation in the *Pichia* spent media, in which the C-terminal cysteines in the C-terminal extension in each of said two polypeptides were oxidized to a disulfide derivative cystine via their thiol moieties at near neutral pH. In order to optimize the oxidation process, oxidizing copper ions were added ($Cu^{2+}$ in the form of $CuSO_4$) in essence as set out in WO2010/125187. The dimers were purified to homogeneity and subsequently analyzed via size exclusion chromatography. Samples were also verified by LC-MS. The resulting data demonstrated that nearly 100% of the thiol moieties were oxidized after treatment with 1 mM $CuSO_4$ for 2 h at room temperature. In none of the chromatograms the formation of significant (undesirable) pre-peaks was observed. Moreover, in none of the chromatograms evidence was seen for the formation of significant pre-peaks indicating that the copper treatment does not seem to oxidize methionines in the protein, nor does the total mass analysis detect any +16 Da mass increase which would be consistent with a single oxidation on for example a methionine.

Dimers were prepared from T023800001, 1023800003, T023800005 and T023800006. The dimer of T023800001 (designated T023800001-dimer) is shown in FIG. 1.

1.4 Stability

The different constructs of the invention, e.g. dimers, polypeptides and benchmarks, were tested for stability after storage under stringent stress conditions. These conditions comprised of incubation of the polypeptides of invention for longer period of time (3 weeks and 6 weeks) at different temperatures (25° C. and 40° C.), essentially as set out in WO2014/184352.

It was demonstrated that the polypeptides of the invention, e.g. with a C-terminal extension comprising a cysteine moiety, and dimers had similar properties as the parent molecules they were derived from and were stable for prolonged periods at 4° C., 25° C. as well at 40° C., without significant chemical degradation and modifications (data not shown) In addition, stability after various cycles of freeze-thaw and 4° C. storage for longer period of time (i.e. >4 d) did not changes, as shown in the functional assays (cf. below)

2 Characterization of Polypeptides Binding to MDA-MB-468 Cells

Polypeptides were characterized in a binding competition assay to assess the EGFR binding affinities. MDA-MB-468 breast cell cancer cell line (mammary gland/breast; derived from metastatic site:
pleural effusion; ABL216) was used.

In order to detect binding of the polypeptide to cells expressing EGFR, the FLAG-tagged 7D12 was used as a competitor. To setup the assay, first a titration series of the FLAG-tagged 7D12 was performed on the MDA-MB-468 cells. The $EC_{90}$ (41 nM) of FLAG-tagged 7D12 was chosen in a competition setup in which non-tagged polypeptides were titrated.

In brief, 100 000 cells were transferred to the plate. The plates were washed twice by centrifugation at 200 g for 3 minutes at 4° C. Supernatant was removed and 50 µl of purified polypeptide was added to the well together with 50 µl of FLAG-tagged 7D12 (final concentration 41 nM) in a total of 100 µl per well. After 90 minutes incubation at 4° C., plates were washed three times by centrifugation for 30 min at 4° C. Supernatant was removed and 100 µl per well of 0.5 µg mouse anti-flag mAb (Sigma-Aldrich, cat #F1804) or FACS buffer was added, followed by an 30 minutes incubation at 4° C. Cells were washed three times by centrifugation at 200 g during 3 minutes at 4° C. After removing the supernatant, 110 µl per well of goat anti-mouse PE or goat anti-human IgG PE was added to the cells and incubated for 30 minutes at 4° C. Plates were then centrifuged for 30 minutes at 200 g at 4° C., supernatant removed and 100 µl per well FACS buffer was added and sequentially the plates were washed three times by centrifugation at 200 g for 3 minutes at 4° C. Next, dead cells were stained with 100 µl TOPRO (Molecular Probes, T3605) per well and cells were sequentially measured on the FACS Canto (Becton Dickinson). First a gate was set on the intact cells as determined from the scatter profile. Then, dead cells were gated out by their fluorescence profile from the TOPRO stain (5 nM, Molecular probes, T3605). As controls, conditions were taken along where there was no polypeptide present or a known irrelevant polypeptide (data not shown).

The monovalent T023800001-A (indicated herein also as T023800001), half-life extended (HLE) T023800003-A (indicated herein also as T023800003), T23800005-A (indicated herein also as T023800005), T023800006-A (indicated herein also as T023800006) and the non-reduced T023800001-dimer were evaluated.

The results are depicted in FIG. 2.

From these results it can be concluded that competition of T023800001, T023800003, T023800005 and 1023800006 with $EC_{90}$ 7D12-FLAG 41 nM) results in a $K_i$ of 15 nM, 0.63 nM, 0.25 nM and 1.16 nM for 1023800001, 1023800003, T023800005 and 1023800006, respectively. The absolute inhibition constant $K_i$ was calculated using the Cheng-Prusoff equation.

$$K_i = \frac{IC50}{\frac{[L]}{K_D} + 1}$$

Unexpectedly, the T023800001-dimer showed an $K_i$ of 0.12 nM, which is 2 times better than T023800005-A, the best performing genetically fused construct, and even more than 9 times better than T023800006-A, the direct comparator of the T023800001-dimer.

3 Quantification of EGFR Phosphorylation in HER14 Cell Line

To verify if the gain in potency as observed in the competition FACS (see Example 2 above) also translates into a modulation of the EGFR mediated signal transduction, the inventors set out a blocking experiment of EGF mediated EGFR phosphorylation by Nanobodies in NHI 3T3/HER14 cells. The constructs used were 1023800001-A and 1023800006-A as well as T023800001-dimer. Dose-dependent inhibition of EGFR phosphorylation was assessed on HER14 cells expressing only EGFR.

Briefly, HER14 cells were seeded in duplicate into 0.1% gelatin coated 96-well culture plates and grown in DMEM culture medium containing 10% FBS/BS for 24 h. The next day, cells were serum-starved in medium supplemented with 0.1% FCS for 24 hrs and then incubated with the constructs followed by stimulation for 10 minutes with 0.5 nM of recombinant human EGF (R&D Systems, cat #236-EG). EGF concentrations were based on the EC50 obtained in HER14 cells ($EC_{50}$=3.5 ng/ml). In each plate an irrelevant control polypeptide was included as reference (data not shown). Monolayers were rinsed twice with ice-cold D-PBS, and subsequently lysed in ice cold RIPA buffer substituted with 1 mM PMSF. EGF-dependent receptor activation in cell lysates was measured using a Phospho(Tyr1173)/Total EGFR Whole Cell Lysate Kit (Meso Scale Discovery—K15104D). Plates were loaded with 30 µl of lysate, incubated 1 h at RT with shaking and processed according to the manufacturer's protocol. Plates were read on the Sector Imager 2400 (Meso Scale Discovery). The percentage of phospho-protein over total protein was calculated using the formula: (2×p-protein)/(p-protein+total protein)×100.

The results are depicted in FIG. 3.

A dose-dependent inhibition of EGFR phosphorylation was only observed on Her-14 cells expressing EGFR. Since the functional phosphorylation is only mediated via EGFR signaling, the gain of avidity by multivalent formatting is expected to translate into increased inhibition of EGFR phosphorylation in a cell-specific manner.

Even more pronounced than the results from the competition FACS, T023800001-dimer (4.4 nM) shows a 5-6 fold increase in potency when compared to the established bivalent Nanobody T023800006-A (26.6 nM). The monovalent T023800001-A yielded a potency of 10.5 nM.

4 Preparation of Cysteine Extended Monomeric Nanobodies Via SEC 4.1 Background Information It was realized that the polypeptides of the invention comprising at least one immunoglobulin single variable domain (ISVD) and a C-terminal extension comprising a cysteine moiety at the C-terminus are suitable for maleimide chemistry based coupling reactions (cf. Example 1.2 above).

To convert the dimers to monomeric polypeptides and make the C-terminal cysteine available for coupling, a reduction needed to be carried out. However, care should be taken to design optimized conditions resulting in reduction of the disulfide dimer without reducing the internal canonical ISVD disulfide bridges. Reduction was carried out preferably using DTT or TCEP. Unlike TCEP, DTT needs to be removed to create optimal coupling conditions. Via Size Exclusion Chromatography (SEC) monomeric Nanobody is separated from non-reduced dimeric Nanobody and DTT.

4.2 Reduction Protocol

The reduction protocol consisted of an overnight treatment with 10 mM DTT at 4° C. (or during minimum 2 h at room temperature) in D-PBS. ISVD concentration was between 2 and 10 mg/ml. It was demonstrated that these conditions did not affect the internal canonical disulfide bond (see FIG. 4 below). Similar results were obtained using TCEP, here we used immobilized TCEP (Pierce, Immobilized TCEP Disulfide Reducing Gel, #77712) according to the manufacturers protocol. Alternatively a short exposure to 10 mM TCEP during 30 minutes at 4° C. was used.

4.3 Size Exclusion Chromatography (SEC)

For purification, preferably a Superdex 75 column (GE Healthcare) was used (separation range 5-100 kDa) for polypeptides comprising up to three ISVDs to generate monomeric reduced products. For analytical purpose, HPLC columns were used such as Agilent SEC-3. The equilibration and the running buffer was D-PBS.

An exemplary of a fully reduced pure product after SEC is provided in FIG. 5.

Following SEC, the reduced monomeric polypeptide was immediately used for conjugation or frozen to prevent re-oxidation into dimers. Experimental evidence suggested that the reduced monomeric fraction of GGC extended polypeptides is stable up to 24 h at 4° C. in D-PBS (data not shown).

A polypeptide comprising two ISVDs was reduced with 10 mM DTT during 2 h at ambient temperature and sized on a Superdex 75 XK 16/60 column (GE Healthcare) equilibrated in D-PBS. Only minute amounts of dimer were detected; the remainder of material was reduced to monomer and hence ready for conjugation. The molecular weight of the gel filtration standard (Biorad), dotted line, is shown above the respective peaks.

5 Polypeptides Coupled to MMAE

The hydrophobic antimitotic agent monomethyl auristatin E (MMAE) is a synthetic analog of the natural product dolastatin 10. MMAE is a potent inhibitor of tubulin polymerization in dividing cells.

In this example, we set out to couple MMAE to the freed C-terminal cysteine of the polypeptides of the invention. In short, MMAE was conjugated via a valine-citrulline linker to the polypeptide for drug targeting purposes. The valine-citrulline linker is highly stable in serum but is cleaved by lysosomal enzymes like cathepsin B after internalization of the conjugate by target cells. The following linker abbreviations are used herein and have the indicated definitions: Val Cit is a valine-citrulline, dipeptide site in protease cleavable linker; PAB is p-aminobenzoyl; mc is maleimide conjugated.

Nanobodies were reduced with 10 mM DTT overnight at 4° C. and then buffer exchanged to remove the excess of DTT. The conjugation with mc-val-cit-PAB-MMAE (MW about 0.7 kDa; FIG. 6) was conducted at 22° C. After 1 hour, the reaction was quenched 20 equivalents N-acetyl-cysteine per free drug. The resulting product was purified by centrifugal concentration and buffer exchanged to final buffer. For purification at larger scale, a non-centrifugal diafiltration method is more suited. The product solution is sterile filtered (0.2 mm).

Polypeptides conjugated to MMAE:
T023800001=>T023800001-mc-val-cit-PAB-MMAE (ABL 100-NC003-1)
T023800003=>T023800003-mc-val-cit-PAB-MMAE (ABL 100-NC003-3)
T023800005=>T023800005-mc-val-cit-PAB-MMAE (ABL 100-NC003-5)
T023800006=>T023800006-mc-val-cit-PAB-MMAE (ABL 100-NC003-6)
T023800008=>T023800008-mc-val-cit-PAB-MMAE (ABL 100-BF012-1)

An HIC-HPLC analysis was performed to determine the Drug to polypeptide ratios (DAR). In short, Analytical HIC of conjugates was carried out using a TOSOH, TSKgel Butyl-NPR column (35×4.6 mm) connected to a Dionex Ultimate 3000RS HPLC system. A linear gradient from 100% buffer A (1.5 M ammonium sulfate in 50 mM sodium phosphate, pH 7.0) to 100% buffer B (20% isopropanol (v/v) in 50 mM sodium phosphate) over 30 min at a flow rate of 0.8 mL/min. The column temperature was maintained at 30° C. throughout the analysis and UV detection was carried out at 280 nm. For each analysis, 10 µg of sample was injected. Peaks were assigned drug to polypeptide ratios (DARs) based on shifts to higher retention time and by A248/A280 ratios. Average DARs were calculated by taking the sum of the individual DAR values multiplied by the fraction of the species (expressed as a decimal). Polypeptides used were ABL 100-NC003-1, ABL 100-NC003-3, ABL 100-NC003-5 and ABL 100-NC003-6.

The results are provided in Table 5

TABLE 5

|  | DAR-0 | DAR-1 | DAR-2 | purity % (SEC) | SDS-PAGE |
|---|---|---|---|---|---|
| ABL 100-NC003-1 | 1.3% | 98.7% | 0% | 97.7 | 96.7 |
| ABL 100-NC003-3 | 1.1% | 98.9% | 0% | 96.3 | 96.9 |
| ABL 100-NC003-5 | 1.7% | 98.3% | 0% | 98.6 | 96.8 |
| ABL 100-NC003-6 | 1.2% | 98.8% | 0% | 98.1 | 95.1 |
| ABL 100-BF012-1 | 0% | 100% | 0% | 97.6 | 97.6 |

An SDS-PAGE analysis was performed to determine the oxidation status of the polypeptides. In short, the SDS-PAGE analysis was carried out using NUPAG® 4-12% Bis-Tris gels (Invitrogen, Cat #NP0321BOX) under non-reducing conditions with MES buffer. For analysis, 1 µg of sample (based on protein) was loaded onto the gel per lane. Electrophoresis was carried out at 200 V for 35 min. The gel were stained with INSTANTBLUE™ (Expedeon, Cat #ISB1LUK) for protein detection and analysed using IMAGEQUANT® imaging equipment (GE Healthcare).

A summary of the results is also provided in Table 5. An exemplary result is provided as FIG. 7.

In order to further confirm and elaborate the results of the SDS-PAGE, an SE-HPLC analysis was performed to determine the percentage purity and aggregation. In short, SE-HPLC was carried out using a Waters ACQUITY® UPLC BEH200 SEC column (4.6 mm×30 cm, 1.7 µm), connected to an Agilent Infinity 1260 Bioinert system. The mobile phase was 0.1 M sodium phosphate buffer, pH 6.8, containing 15% (v/v) isopropanol. The flow rate was kept constant at 0.15 mL/min. The column was maintained at 25° C. throughout the analysis. The analysis was carried out in a 30 min isocratic elution with UV detection at 280 nm. For each analysis, 10 µg of sample was injected. The % purity and % aggregation present were calculated by comparing the peak areas of the main peaks and early eluting peaks respectively with total peak area.

The results are summarized in Table 5. An exemplary HIC analysis of the coupling result is depicted in FIG. 8.

This means that for all polypeptides the reaction results in an efficiency of over 98% of the polypeptides for conjugation to the ADC. Moreover, the reaction resulted in a DAR of 1, implying on the one hand that the ISVDs were intact, e.g. no internal thiols were used, and on the other hand a very controlled number of drugs per polypeptide. This results in a better safety profile, in contrast to the Gaussian distribution of drugs conjugated to conventional antibodies.

TABLE 6

| Name | amino acid sequence |
|---|---|
| 23800001 (SEQ ID NO: 27) | EVQLEESGGGSVQTGGSLRLTCAASGRTSRSYGMGWFRQAPGKEREFVSGISWRGDSTGYADSVKGRFTI SRDNAKNTVDLQMNSLKPEDTAIYYCAAAAGSAWYGTLYEYDYWGQGTQVTVSSGGGGSGGGGSGGGGSG GGGSEVQLVESGGGLVQPGNSLRLSCAASGFTFSSFGMSWVRQAPGKGLEWVSSISGSGSDTLYADSVKG RFTISRDNAKTTLYLQMNSLRPEDTAVYYCTIGGSLSRSSQGTLVTVSSGGC |

TABLE 6-continued

| Name | amino acid sequence |
|---|---|
| 23800003 (SEQ ID NO: 28) | EVQLEESGGGSVQTGGSLRLTCAASGRTSRSYGMGWFRQAPGKEREFVSGISWRGDSTGYADSVKGRFTI SRDNAKNTVDLQMNSLKPEDTAIYYCAAAAGSAWYGTLYEYDYWGQGTQVTVSSGGGGSGGGGSGGGGSG GGGSEVQLEESGGGSVQTGGSLRLTCAASGRTSRSYGMGWFRQAPGKEREFVSGISWRGDSTGYADSVKG RFTISRDNAKNTVDLQMNSLKPEDTAIYYCAAAAGSAWYGTLYEYDYWGQGTQVTVSSGGC |
| 23800005 (SEQ ID NO: 29) | EVQLEESGGGSVQTGGSLRLTCAASGRTSRSYGMGWFRQAPGKEREFVSGISWRGDSTGYADSVKGRFTI SRDNAKNTVDLQMNSLKPEDTAIYYCAAAAGSAWYGTLYEYDYWGQGTQVTVSSGGGGSGGGGSGGGGSG GGGSEVQLVESGGGLVQAGGSLRLSCAASGRTFSSYAMGWFRQAPGKEREFVVAINWSSGSTYYADSVKG RFTISRDNAKNTMYLQMNSLKPEDTAVYYCAAGYQINSGNYNFKDYEYDYWGQGTQVTVSSGGC |
| 23800006 (SEQ ID NO: 30) | EVQLEESGGGSVQTGGSLRLTCAASGRTSRSYGMGWFRQAPGKEREFVSGISWRGDSTGYADSVKGRFTI SRDNAKNTVDLQMNSLKPEDTAIYYCAAAAGSAWYGTLYEYDYWGQGTQVTVSSGGGGSGGGGSGGGGSG GGGSEVQLEESGGGSVQTGGSLRLTCAASGRTSRSYGMGWFRQAPGKEREFVSGISWRGDSTGYADSVKG RFTISRDNAKNTVDLQMNSLKPEDTAIYYCAAAAGSAWYGTLYEYDYWGQGTQVTVSSGGGGSGGGGSG GGSGGGGSEVQLVESGGGLVQPGNSLRLSCAASGFTFSSFGMSWVRQAPGKGLEWVSSISGSGSDTLYAD SVKGRFTISRDNAKTTLYLQMNSLRPEDTAVYYCTIGGSLSRSSQGTLVTVSSGGC |
| 23800008 (SEQ ID NO: 31) | EVQLEESGGGSVQTGGSLRLTCAASGRTSRSYGMGWFRQAPGKEREFVSGISWRGDSTGYADSVKGRFTI SRDNAKNTVDLQMNSLKPEDTAIYYCAAAAGSAWYGTLYEYDYWGQGTQVTVSSGGGGSGGGGSGGGGSG GGGSEVQLVESGGGLVQAGGSLRLSCAASGRTFSSYAMGWFRQAPGKEREFVVAINWSSGSTYYADSVKG RFTISRDNAKNTMYLQMNSLKPEDTAVYYCAAGYQINSGNYNFKDYEYDYWGQGTQVTVSSGGGGSGGGG SGGGGSGGGGSEVQLVESGGGLVQPGNSLRLSCAASGFTFSSFGMSWVRQAPGKGLEWVSSISGSGSDTL YADSVKGRFTISRDNAKTTLYLQMNSLRPEDTAVYYCTIGGSLSRSSQGTLVTVSSGGC |

5.1. In Vitro Cell Toxicity of Polypeptides Coupled to MMAE

The effect of MMAE-conjugated polypeptides on cell proliferation and/or cell toxicity was tested using the XCELLIGENCE® instrument (Analyser Model W380; SN: 281081212038, Roche). The instrument quantifies changes in electrical impedance as cells attach and spread in a culture dish, displaying them as a dimensionless parameter termed cell-index, which is directly proportional to the total area of tissue-culture well that is covered by cells (Duchateau et al. 2013. *Phys. Status Solidi* 10: 882-888 and Giaever and Keese 1991. *Proc. Natl. Acad. Sci. USA* 88: 7896-7900). The XCELLIGENCE® instrument (Analyser Model W380; SN: 281081212038) utilizes the E-plates 96 (ACEA Biosciences; cat #05 232 368 001; lot #20140138; plate 1: ID #079605; plate 2: ID #079606) as tissue-culture well plate for seeding cells. The constructs used were T023800001-A and T023800001-MMAE, T023800003-A and T023800003-MMAE, T023800005-A and T023800005-MMAE, and T023800006-A and T023800006-MMAE. Dose-dependent inhibitory effect on MDA-MB-468 (mammary gland/breast; derived from metastatic site: pleural effusion; ABL216) cell proliferation of the non-conjugated and MMAE-conjugated Nanobodies was assessed with the XCELLIGENCE® instrument using the following protocol.

In brief, the XCELLIGENCE® station was placed in a 37° C. incubator in presence of 5% $CO_2$. MDA-MB-468 cell are grown T175 flasks containing RPMI (Gibco, Cat Nr: 72400-021) supplemented with 1% P/S (Gibco, Cat Nr: 15140-122); 1% Na pyruvate (Gibco, Cat Nr: 11360-039) and 10% FBS (Sigma-Aldrich, Cat Nr: F7524). Cells are harvested by trypsinization, centrifugation and re-suspending them to indicated cell densities. 50 µl of cell medium was added to each well of E-plate 96 and a blank reading on the XCELLIGENCE® system was performed to measure background impedance in absence of cells. 6000 cells (50 µl) are transferred to each well of an E-plate 96 and incubated for 20 h to let the cells adhere. 100 µl of each polypeptide was administered in a 1:3 dilution series, starting from 500 nM (total volume per well is 200 µl). Impedance readings were programmed at 15 minute intervals. The experiments were stopped at time point 162 h (±7 d). The cell indices measured at time point 116 h after seeding for all tested concentrations were used for dose-response analysis.

Proliferation curves and dose-response curves are depicted respectively in FIG. 9 and FIG. 10. The obtained $IC_{50}$ values are given in Table 7.

TABLE 7

$IC_{50}$ and % inhibition observed for the non- and MMAE-conjugated polypeptides

| polypeptide | $IC_{50}$ (nM) | % Inhibition |
|---|---|---|
| T023800001-A | — | — |
| T023800001-MMAE | 28.7 | 99.8 |
| T023800003-A | — | — |
| T023800003-MMAE | 6.2 | 76.8 |
| T023800005-A | 34.9 | 44.9 |
| T023800005-MMAE | 1.2 | 91.9 |
| T023800006-A | — | — |
| T023800006-MMAE | 8 | 89.7 |

The non-conjugated polypeptides T023800001-A, T023800003-A, T023800005-A and T023800006-A exhibit no apparent effect on the proliferative properties of MDA-MB-468 cells, except the biparatopic T023800005-A which demonstrates a slight inhibitory effect on cell proliferation. In contrast, the M MAE-conjugated polypeptides T023800001-M AE, T023800003-MMAE, T023800005-MMAE and T023800006-M AE clearly show a dose-dependent inhibitory effect on cell proliferation with almost complete inhibition at highest dose, as shown in FIG. 9.

5.2 In Vivo Efficacy of Polypeptides Coupled to MMAE

The in-vivo efficacy study of anti-EGFR polypeptide drug conjugates was assessed in a subcutaneous xenograft mouse model.

Tumors were induced by subcutaneous injection of $1 \times 10^7$ FaDu cells into the right flank of healthy SWISS nude female mice of 6-8 weeks old. The FaDu cell line is a head and neck cancer cell line established from a punch biopsy of a hypopharyngal tumor removed from a 56-year old Caucasian/Hindu male patient. The treatment was started when tumors reach a mean volume between 100-200 $mm^3$.

The animals received a daily injection of T023800008-MMAE at 5 mg/kg every 4 days with a total of 6 injections (Q4D×6). A first control group received daily injections every 4 days with a total of 6 days of a non-EGFR binding, but MMAE conjugated polypeptide at equimolar dose. A second control group received a daily injection of vehicle every 4 days for a total of 6 injections. Each groups consisted of 12 animals.

The length and the width of the tumor were measured twice a week with calipers and the volume of the tumor was estimated according to the following formula:

The polypeptide-MMAE conjugate T023800008-MMAE showed a significant inhibitor of tumor growth compared to the 2 control groups (FIG. 11).

6 Generation of Bispecific Dimers

In this example protocols are provided enabling the generation of bispecific dimers, i.e. dimers in which polypeptide 1 is dissimilar from polypeptide 2.

6.1 Standard Protocol

In first instance the protocol of Example 1.3 above is followed, but in which one *Pichia* strain produces both, dissimilar polypeptides. The coupling of the polypeptides into a dimer is also performed by chemical conjugation in the *Pichia* spent media, in which the C-terminal cysteines in the C-terminal extension in each of said two polypeptides are oxidized to a disulfide derivative cystine via their thiol moieties at near neutral pH. In order to optimize the oxidation process, oxidizing copper ions are added ($Cu^{2+}$ in the form of $CuSO_4$) in essence as set out in WO2010/125187. The dimers are purified to homogeneity (ion-exchange chromatography) and subsequently analyzed via size exclusion chromatography. Samples are also verified by LC-MS. The standard protocol will generate the intended bispecific NB1-NB2 dimers. However, it is expected that a fraction will also contain monospecific dimers, e.g. NB1-NB1 and NB2-NB2.

6.2 Alternative Protocol

Nanobody heterodimers (bispecific dimers) can be generated using two distinct C-terminally Cysteine extended Nbs without the use of a crosslinker.

This can be achieved via non-covalent immobilization of the first Nanobody (=NbA) while making its free sulfhydryl available to the second Nanobody (=NbB) to form a C-terminal heterodimeric disulfide bond.

In a first Step NbA is reduced to obtain 100% monomeric material. Generic conditions for reducing typical Nanobody solutions [5-10 mg/ml] are 10 mM DTT in D-PBS overnight at 4° C. or during 1-2 h at Room temperature (RT). Preferably the optimal conditions are determined for each individual Nanobody so that its canonical disulfide bond remains intact.

In Step 2 the NbA monomeric fraction is bound under reducing conditions to a carrier. Such a carrier could be a chromatography resin which preferably only binds NbA and not NbB. NbA is immobilized at low density to avoid the formation of NbA-NbA dimers while immobilized. Such a spatial separation of individual NbAs could be achieved by loading the column using sub-optimal binding conditions (i.e. a too high flow rate for a typical affinity resin) or via expanding bed chromatography. Preferably the carrier only binds NbA. So ProteinA could be used if NbA (and preferably not NbB) is a Protein A binder. If both Nanobodies A and B bind the carrier then the carrier, after immobilizing NbA, should be saturated with a non-cysteine extended Nanobody before applying NbB.

In Step 3 an excess of the second Nanobody (NbB), also in reduced form (see above), is applied and is circulated over the column (optionally under slightly oxidizing conditions). NbB is passed over the carrier until the immobilised NbA is fully complexed with NbB via a disulfide bond. This can be followed by measuring the concentration drop of NbB to match a saturated NbA population. For this step conditions are optimized to limit the amount of NbB-NbB dimer formation. This population will not bind the carrier and can be recovered and used in future coupling reactions.

In Step 4 the NbA-NbB dimer preparation is recovered from the resin by typical elution conditions for that column (i.e. acidic conditions for Protein A) and further processed/formulated.

7 PK Study of Dimers and Drug-Conjugated Polypeptides

As indicated above, already due to the size differences, dimerization and conjugation of drugs to the polypeptides of the invention has a far larger influence than on conventional antibodies. Accordingly, the inventors set out to assess the effects of a payload conjugated to a Nanobody with a DAR=1 has on the PK properties.

In addition, the inventors set out to assess the PK properties of a dimer of the invention comprising 2 human serum albumin binding domains ("Alb"). As will be evident from the examples above, a dimer comprising two identical moieties (i.e. polypeptide 1=polypeptide 2) is easier and more cost effectively to generate and purify than a dimer with two dissimilar moieties. Human serum albumin binding domains are necessary in various instances for extending the half-life of the construct. However, having an additional human serum albumin binding domain should not have any negative effect on the PK profile of the construct.

7.1 Radiolabeling of Polypeptides

The PK properties were tested via radiolabeled polypeptides. In short, polypeptides were radiolabeled with $^{89}Zr$, NCS-Bz-Df via randomly conjugation on free —$NH_2$ (see FIG. 12). 22 nmol polypeptide (1.0 mg) was mixed with 0.9% NaCl until a final volume of 500 µL (final concentration 2 mg/mL). Next, the pH was set to 8.9-9.1 by adding 0.1 M $Na_2CO_3$. Finally, a solution of 66 nmol NCS-Bz-Df in DMSO (3 eq, 10 µl) was added and reacted for 30 min at 37° C. After 30 min the reaction mixture was purified by using a 50 mM NaOAc/200 mM Sucrose prewashed PD10 column. The product was collected in a fraction of 1.0 mL. The Df-PK-polypeptides were next radiolabeled with $^{89}Zr$ at pH~7 for 60 min at room temperature (reaction mixture contained: 100 µL 1 M Oxalic acid containing $^{89}Zr$, 45 µL 2 M $Na_2CO_3$, 500 µL 0.5 M Hepes buffer (pH 7.2) and 355 µL NCS-Df-polypeptide (~0.4 mg). Next, the reaction mixture was purified over a prewashed PD10 column with 50 mM NaOAc/200 mM Sucrose and the product collected in 1.5 mL.

TABLE 8

| | Labelling results polypeptides | | | | |
|---|---|---|---|---|---|
| Polypeptide | radiolabeling yield (MBq) | radiolabeling yield (%) | Spinfilter (%) | HPLC (%) | Lindmo binding (%) |
| $^{89}$Zr-T023800001 | 5,484 | 19.2 | 87.7 | 91.4 | 95.0 |
| $^{89}$Zr-T023800006A | 2,742 | 9.6 | 97.7 | 96.4 | 95.5 |
| $^{89}$Zr-T023800006-MMAE | 10,878 | 37.6 | 98.2 | 100 | 90.6 |

The radiolabeling results are summarized in Table 8. The radiolabeling yields varied between 9.6% and 37.6% (normally a radiolabeling yield of 70% is expected). Probably this low labeling yield has to do with the low polypeptide amount that was used during modification. HPLC and Spinfilter analysis showed that the radiochemical purity was satisfactory for $^{89}$Zr-T023800006A and $^{89}$Zr-T023800006-MMAE (>96%). $^{89}$Zr-T023800001 showed a purity <90.0% for spinfilter analysis, HPLC showed 8.6% free $^{89}$Zr. Normally a construct should have a radiolabeled purity of >90.0%. In this case, it was decided to use $^{89}$Zr-T023800001 anyway for the PK study, since the spinfilter purity of $^{89}$Zr-T023800001 is near 90% and HPLC analysis shows a >90% pure product. Lindmo binding was >90% for all polypeptides (data not shown).

Subsequently, the $^{89}$Zr-PK radiolabeled polypeptides were formulated to an activity of 0.22 MBq/mice, concentration 50 µg/mL with an injection volume of 130 µL.

In conclusion, the radiolabeling yields were not as efficient as expected. The radiochemical purity of $^{89}$Zr-T023800006A and $^{89}$Zr-T023800006-MMAE was good (>97% according to spinfilter and >96% according to HPLC). The Lindmo binding results were high, with >90%. $^{89}$Zr-T023800001 was not as pure as required with the spinfilter analysis. Eventually it was decided to still use $^{89}$Zr-T023800001. All polypeptides were formulated and injected successfully.

7.2 In Vivo PK Studies 3 mice were injected with radiolabeled ($^{89}$Zr) polypeptide and the cpm (counts per minute) values were detected at 9 time points: 5 min, 1 h, 3 h, 24 h, 48 h, 72 h, 140 h, 168 h and 192 h. These values were then used to calculate the % injected dose of polypeptide per g mouse (% ID/g). For each polypeptide, the results of the 3 mice were averaged.

The results are summarized in FIG. 13.

The results show unexpectedly that the biodistribution profile of bivalent polypeptides (T-023800006-A) is similar as the biodistribution profile of the drug-conjugated polypeptides (T-023800006-MMAE). Conjugating a polypeptide of the invention with a payload has no effect on the biodistribution profile. Without being bound to any theory, it was hypothesized that the tightly controlled conjugation process resulting in a DAR=1 is predictive for the PK properties (in this case, no variance compared to the non-conjugated polypeptides).

Also unexpectedly, the biodistribution profile of the cys-linked dimer of the invention (T-023800001) is similar to of a corresponding bivalent polypeptide (T-023800006-A). The presence of two human serum albumin binding units in the cys-linked dimer of the invention does not affect the distribution profile.

8 Improved Internalization by Dimers

The aim of this experiment was to assess whether a Cys-linked dimer DIM T023800001 (i.e. bivalent from a functional perspective) shows an increased internalization compared to its monomeric counterpart (T023800001-A) and traditionally linked-genetic fusion-bivalent format (T023800006-A). For this purpose, an internalization experiment was performed on NCI-H292 cells, which moderately express the EGF Receptor. The accumulation of internalized Nanobodies in life cells was measured via Flow CytoMetry (FCM) using a pHrodo™ labeled albumin (50 µg/ml) as detection tool. pHrodo® dye is a pH-sensitive Molecular Probe and almost non-fluorescent at neutral pH. In acidic environments such as in endosomes and lysosomes, it fluoresces brightly. Cells (30.000 cells/well) were transferred in a flat bottom 96-well plate and incubated for 5 hrs. at 3TC with different concentrations of the particular polypeptides and constructs together with the pHrodo™ labeled albumin (50 µg/ml). Cells were then washed, harvested, measured on FCM and analyzed.

The obtained dose-response curves are presented in FIG. 14 and correlated $EC_{50}$ values and top MFI top levels are listed in Table 9.

TABLE 9

Estimated $EC_{50}$ values and MFI Top levels

| | $EC_{50}$ (nM) | MFI Top |
|---|---|---|
| DIM T023800001 | 0.7 | 42102 |
| T023800001-A | >23 | Not reached |
| T023800006-A | >16 | Not reached |

Remarkably, in NCI-H292 cells, the overall internalization of DIM T023800001 appeared to be more potent and efficacious than the monomer T023800001-A and traditionally linked bivalent Nanobody T023800006-A. Moreover, this difference in internalization is less pronounced yet still significant in cells that express EGFR in extreme high levels such as MDA-MB-468 (data not shown).

The entire contents of all of the references (including literature references, issued patents, published patent applications, and co pending patent applications) cited throughout this application are hereby expressly incorporated by reference, in particular for the teaching that is referenced hereinabove.

The Figures and the Experimental Part/Examples are only given to further illustrate the invention and should not be interpreted or construed as limiting the scope of the invention and/or of the appended claims in any way, unless explicitly indicated otherwise herein.

The invention claimed is:

1. A method of killing a cancer cell having a Receptor Tyrosine Kinase on its surface, the method comprising contacting the cancer cell with a polypeptide-drug conjugate, wherein the polypeptide-drug conjugate comprises:
   (i) a dimer comprising: a first polypeptide comprising at least one immunoglobulin single variable domain (ISVD) and a C-terminal extension consisting of 2 to 10 amino acids and comprising a cysteine moiety, wherein the most C-terminal amino acid of the first polypeptide is not cysteine; and a second polypeptide comprising at least one immunoglobulin single variable domain (ISVD) and a C-terminal extension consisting of 2 to 10 amino acids and comprising a cysteine moiety, wherein the most C-terminal amino acid of the second polypeptide is not cysteine; and
   (ii) a cytotoxic drug conjugated to the dimer;
   wherein said first polypeptide and said second polypeptide are covalently linked via a disulfide bond between the cysteine moiety in the C-terminal extension of said first polypeptide and the cysteine moiety in the C-terminal extension of said second polypeptide; and said disulfide bond between the cysteine moiety in the C-terminal extension of said first polypeptide and the cysteine moiety in the C-terminal extension of said second polypeptide is the only intermolecular disulfide bond present in the dimer, and
   wherein at least said first polypeptide binds to the Receptor Tyrosine Kinase on the surface of the cancer cell, and upon binding is capable of being internalized by the cancer cell.

2. The method according to claim 1, wherein the C-terminal extension of the first polypeptide or the second polypeptide consists of 6, 5, 4, 3, or 2 amino acid residue(s).

3. The method according to claim 1, wherein said first polypeptide and said second polypeptide are identical.

4. The method according to claim 1, wherein said first polypeptide and said second polypeptide are different.

5. The method according to claim 1, wherein the cytotoxic drug is chosen from the group consisting of cytostatic agents; cytotoxic agents; chemotherapeutic agents; growth inhibitory agents; toxins, optionally an enzymatically active toxin of bacterial, fungal, plant, or animal origin, or fragments thereof; toxin moieties; and radioactive isotopes.

6. The method according to claim 1, wherein the Receptor Tyrosine Kinase is an epidermal growth factor receptor.

* * * * *